US012428652B2

(12) United States Patent
Kazuki et al.

(10) Patent No.: US 12,428,652 B2
(45) Date of Patent: Sep. 30, 2025

(54) MOUSE ARTIFICIAL CHROMOSOME VECTOR AND USE THEREOF

(71) Applicants: NATIONAL UNIVERSITY CORPORATION TOTTORI UNIVERSITY, Tottori (JP); Trans Chromosomics, Inc., Yonago (JP)

(72) Inventors: Yasuhiro Kazuki, Tottori (JP); Mitsuo Oshimura, Tottori (JP); Satoshi Abe, Tottori (JP)

(73) Assignees: NATIONAL UNIVERSITY CORPORATION TOTTORI UNIVERSITY, Tottori (JP); Trans Chromosomics, Inc., Yonago (JP)

( * ) Notice: Subject to any disclaimer, the term of this patent is extended or adjusted under 35 U.S.C. 154(b) by 1088 days.

(21) Appl. No.: 16/981,164

(22) PCT Filed: Mar. 15, 2019

(86) PCT No.: PCT/JP2019/010953
§ 371 (c)(1),
(2) Date: Sep. 15, 2020

(87) PCT Pub. No.: WO2019/177163
PCT Pub. Date: Sep. 19, 2019

(65) Prior Publication Data
US 2021/0095311 A1 Apr. 1, 2021

(30) Foreign Application Priority Data
Mar. 16, 2018 (JP) ................................ 2018-050178

(51) Int. Cl.
*C12N 15/85* (2006.01)
*A01K 67/0275* (2024.01)
*C07K 16/00* (2006.01)

(52) U.S. Cl.
CPC ...... *C12N 15/8509* (2013.01); *A01K 67/0275* (2013.01); *C07K 16/00* (2013.01); *A01K 2227/105* (2013.01); *A01K 2267/01* (2013.01); *C07K 2317/10* (2013.01); *C07K 2317/21* (2013.01); *C12N 2015/8518* (2013.01)

(58) Field of Classification Search
CPC .................................................. C12N 15/8509
See application file for complete search history.

(56) References Cited

U.S. PATENT DOCUMENTS

| 2006/0185025 A1 | 8/2006 | Oshimura et al. |
| 2010/0011454 A1 | 1/2010 | Kakeda et al. |
| 2011/0023138 A1 | 1/2011 | Oshimura et al. |
| 2012/0272342 A1 | 10/2012 | Oshimura et al. |
| 2015/0096063 A1* | 4/2015 | Oshimura .......... C12N 15/8509 800/9 |

FOREIGN PATENT DOCUMENTS

| CN | 101535474 A | 9/2009 |
| CN | 102791857 A | 11/2012 |
| EP | 2 522 725 A1 | 11/2012 |
| JP | 2007-295860 A | 11/2007 |
| JP | 2015-119643 A | 7/2015 |
| WO | WO 2004/031385 A1 | 4/2004 |
| WO | WO 2008/013067 A1 | 1/2008 |
| WO | WO 2009/063722 A1 | 5/2009 |
| WO | WO 2011/083870 A1 | 7/2011 |

OTHER PUBLICATIONS

Pletcher et al Genome Res. 10, 1463-1467 (Year: 2000).*
NCBI accession No. NC_000076.6 , p. 1 (Year: 2012).*
Gregory, S. G. et al. Nature 418, 743-750 (Year: 2002).*
Takehara et al Transgenic Res, 23:441-453 (Year: 2014).*
Shinohara et al Chromosome Research 8: 713-725 (Year: 2000).*
European Supplementary Search Report Issued Apr. 8, 2021 in European Patent Application No. 19767483.1, 6 pages.
Oshimura, M., et al., "New Vectors for Gene Delivery: Human and Mouse Artificial Chromosomes", In: "Encyclopedia of Life Sciences", Feb. 15, 2013, John Wiley & Sons, Ltd., XP055788345, pp. 1-12.
Satoh. D., et al., "Human and mouse artificial chromosome technologies for studies of pharmacokinetics and toxicokinetics", Drug Metabolism and Pharmacokinetics. vol. 33, No. 1, Feb. 1, 2018, XP055746028, pp. 17-30.
Extended European Search Report issued Apr. 8, 2021 in corresponding European Patent Application No. 19767483.1, 6 pages.
Anonymous: "Gm35974 predicted gene, 35974 [*Mus musculus* (house mouse)]", XP055788661, Sep. 25, 2020, 4 pages Retrieved from the Internet: URL:https://www.ncbi.nlm.nih.gov/gene?cmd=retrieve&list uids=102639732.
Tao Yu et al., "A mouse model of Down syndrome trisomic for all human chromosome 21 syntenic regions", Human Molecular Genetics, 2010, vol. 19, No. 14, doi: 10.1093/hmg/ddq 179, Advance Access published on May 4, 2010, pp. 2780-2791.
International Search Report issued on Jun. 11, 2019 in PCT/JP2019/010953 filed on Mar. 15, 2019, 3 pages.
Kuroiwa et al., "Manipulation of human minichromosomes to carry greater than megabase-sized chromosome inserts", Nature Biotechnology, 2000, vol. 18, pp. 1086-1090.

(Continued)

*Primary Examiner* — Anoop K Singh

(74) *Attorney, Agent, or Firm* — Oblon, McClelland, Maier &Neustadt, L.L.P.

(57) ABSTRACT

A mouse artificial chromosome vector is stable in rodent cells, tissues, and/or individuals, specifically a mouse artificial chromosome vector derived from a mouse chromosome selected from mouse chromosome 10 and mouse chromosome 16. A cell or a non-human animal may include the vector. The vector may be used for producing proteins and human antibodies.

12 Claims, 29 Drawing Sheets

Specification includes a Sequence Listing.

(56) References Cited

OTHER PUBLICATIONS

Katoh et al., "Construction of a novel human artificial chromosome vector for gene delivery", Biochemical and Biophysical Research Communications, 2004, vol. 321, pp. 280-290.
Hoshiya et al., "A highly Stable and Nonintegrated Human Artificial Chromosome (HAC) Containing the 2.4 Mb Entire Human Dystrophin Gene", Molecular Therapy, 2009, vol. 17, No. 2, pp. 309-317.
Takiguchi et al., "A Novel and Stable Mouse Artificial Chromosome Vector", ACS Synthetic Biology, 2012, vol. 3, pp. 903-914.

* cited by examiner

MOUSE ARTIFICIAL CHROMOSOME VECTOR AND USE THEREOF

TECHNICAL FIELD

The present invention relates to a novel mouse artificial chromosome vector capable of being stably retained in rodent cells, tissues, or individuals and of being transmitted to progeny. More specifically, the present invention relates to mouse artificial chromosomes each derived from mouse chromosome 10 and mouse chromosome 16.

The present invention also relates to a mammal-derived cell comprising the mouse artificial chromosome vector.

The present invention further relates to a non-human animal, such as a rodent, comprising the mouse artificial chromosome vector.

The present invention further relates to a method for producing useful proteins or human antibodies using the cell or the non-human animal.

BACKGROUND ART

An artificial chromosome vector can comprise DNA of a large size exceeding approximately 200 kb (e.g., a chromosome fragment of a mega-base size) introduced thereinto. Thus, such artificial chromosome vector is subjected to preparation of a non-human animal that can be used for production of human antibodies, test of drug metabolism, disease models, and other purposes. As such vector, human artificial chromosome (HAC) vectors, mouse artificial chromosome (MAC) vector, and the like have been known. Specifically, the HAC vectors derived from human chromosome 14 and human chromosome 21 are disclosed in Patent Literatures 1, 2, and 3 and Non-Patent Literatures 1, 2, and 3, and the MAC vector derived from mouse chromosome 11 is disclosed in Patent Literature 4.

However, mice with introduced HAC vector(s) have problems, such as a decrease in HAC vector retention rate, variations between tissues or individuals, and unstable progeny transmission frequency. As such, it is constantly necessary that the HAC vector retention rate and other conditions be taken into consideration. When functions or association with diseases of a particular gene region is/are studied, in addition, it is occasionally difficult to in detail and accurately analyze the expression dynamics and expression product of a target gene at cell or tissue level, thereby resulting in disturbing highly reproducible and homogeneous analyses. Furthermore, when a mouse cell is fused to a human cell, a human chromosome is known to be unstable in mouse cells. Thus, because human chromosomes comprising a HAC vector are not retained at a constant level in mouse cells, when a HAC vector is introduced into mouse cells, as well as when a transgenic mouse is prepared, advantages of an artificial chromosome vector cannot be sufficiently exerted.

In contrast, in case of mice with introduced MAC vector(s), problems including decrease in HAC vector retention rate are substantially resolved. However, the vector derived from mouse chromosome 11 is known merely as a MAC vector, and there are problems arising due to use of other vectors. Specifically, the trial-and-error is required to prepare a MAC vector because of the lack of information concerning the chromosome structure, and properties of vectors other than the known MAC vector are not yet known.

Under the above-mentioned circumstances, the present inventors had attempted to prepare two types of MAC vectors each derived from mouse chromosome 10 and mouse chromosome 16.

PRIOR ART LITERATURE

Patent Literature

Patent Literature 1: WO 2009/063722
Patent Literature 2: WO 2004/031385
Patent Literature 3: JP 2007-295860 A
Patent Literature 4: JP Patent No. 5,557,217

Non-Patent Literature

Non-Patent Literature 1: Kuroiwa et al, Nat. Biotech., 18:1086-1090, 2000
Non-Patent Literature 2: Katoh et al, BBRC, 321:280-290, 2004
Non-Patent Literature 3: Hoshiya et al, Mol. Ther., 17:309-17, 2009

SUMMARY OF INVENTION

Problem to be Solved by the Invention

When a MAC vector other than the known MAC vector is to be prepared, problems often arise. For example, there is little information concerning the sequence and the structure of a mouse chromosome, such information may be occasionally unknown, and such sequence information concerns a particular mouse lineage or individual. When a lineage is different, accordingly, sequences are often inconsistent. Genetic engineering aimed at prevention of incorporation of excess mouse genes into a vector requires trials and errors to a significant extent. In addition, differences in chromosome structure containing natural centromere would lead to a difference in position of a MAC vector in nuclei depending upon the origin of a chromosome, which may affect expression control of host genes, and moreover, the growth of stem cells derived from the spermary into which the mouse chromosome 11-derived MAC had been introduced was abnormal under conditions of the culture of the stem cells. As such, it is necessary to solve the above-mentioned problems. As with influence of mouse genes remaining on a MAC vector, in addition, influences of a MAC vector prepared from a mouse chromosome with different chromosome number on properties, such as stability and progeny transmission capacity, are substantially not known and are not clarified.

Ideally, a MAC vector should not cause fluctuation of gene expression in a host that introducing a MAC vector is not intended, and the vector should be stably maintained in rodent cells, tissues, or individuals and should be transmitted to progeny. As described above, however, a trial-and-error process would be required for preparation of such vector.

The present invention provides a novel MAC vector that can solve the problems described above.

Means for Solving Problem

As a summary, the present invention includes the following features.

(1) A mouse artificial chromosome vector comprising: a natural centromere derived from a mouse chromosome selected from the group consisting of mouse chromosome 10 and mouse chromosome 16; a mouse-chromosome-10-derived long-arm fragment formed by deleting a long-arm region distal from the gene Gm8155, which gene is a mouse chromosome 10 long-arm site proximal to the centromere, or a mouse-chromosome-6-derived long-arm fragment formed by deleting a long-arm region distal from the gene Gm35974, which gene is a mouse chromosome 16 long-arm site proximal to the centromere; and a telomere sequence, wherein the vector is stably retained in a rodent cell, tissue, or individual and is capable of transmission to progeny.

(2) The mouse artificial chromosome vector according to (1), comprising a mouse artificial chromosome contained in a deposited cell line DT40 (10MAC) T5-26 (NITE BP-02656).

(3) The mouse artificial chromosome vector according to (1), comprising a mouse artificial chromosome contained in a deposited cell line DT40 (16MAC) T1-14 (NITE BP-02657).

(4) The mouse artificial chromosome vector according to any of (1) to (3), wherein the rodent is a mouse or a rat.

(5) The mouse artificial chromosome vector according to any of (1) to (4), which further comprises one or more DNA sequence insertion sites.

(6) The mouse artificial chromosome vector according to (5), wherein the DNA sequence insertion site comprises at least one sequence selected from the group consisting of a loxP sequence, an FRT sequence, φC31attB and φC31attP sequences, R4attB and R4attP sequences, TP901-1attB and TP901-1attP sequences, and Bxb1attB and Bxb1attP sequences.

(7) The mouse artificial chromosome vector according to any of (1) to (6), further comprising a reporter gene(s), a selection marker gene(s), or both thereof.

(8) The mouse artificial chromosome vector according to any of (1) to (7), further comprising an exogenous DNA sequence(s).

(9) The mouse artificial chromosome vector according to (8), wherein the exogenous DNA sequence(s) is/are a human DNA sequence(s).

(10) The mouse artificial chromosome vector according to (9), wherein the exogenous DNA sequence(s) is/are a DNA sequence(s) of a gene(s) or gene locus (or loci) of the human-chromosome-derived long arm or short arm.

(11) The mouse artificial chromosome vector according to (9) or (10), wherein the exogenous DNA sequence(s) is/are a DNA sequence(s) of a human immunoglobulin heavy chain gene or gene locus, a human immunoglobulin light chain gene or gene locus, or both of heavy chain and light chain genes or gene loci thereof.

(12) The mouse artificial chromosome vector according to any of (8) to (10), wherein the exogenous DNA sequence(s) is/are selected from the group consisting of: gene or DNA sequences encoding polypeptides such as cytokines, hormones, growth factors, nutritional factors, hematopoietic factors, coagulation or hemolysis factors, G protein-coupled receptors, and enzymes; or gene or DNA sequences for use in treatment of diseases such as tumors, muscular dystrophy, hemophilia, neurodegenerative diseases, autoimmune diseases, allergic diseases, and genetic diseases; and gene or DNA sequences in the immune system, such as T cell receptors (TCRs) and human leukocyte antigens (HLAs).

(13) A mammal-derived cell comprising the mouse artificial chromosome vector according to any of (1) to (12).

(14) The cell according to (13), wherein the mammal-derived cell is selected from the group consisting of somatic cells, stem cells, and precursor cells.

(15) The cell according to (13) or (14), wherein the mammal-derived cell is a rodent-derived cell.

(16) A non-human animal comprising the mouse artificial chromosome vector according to any of (1) to (12).

(17) The non-human animal according to (16), which is a rodent animal.

(18) The non-human animal according to (17), wherein the rodent animal is a mouse or a rat.

(19) The non-human animal according to any of (16) to (18), which is capable of producing human antibodies.

(20) The non-human animal according to any of (16) to (19), wherein an endogenous gene(s) corresponding to an exogenous DNA(s) contained in the mouse artificial chromosome vector is/are disrupted, or expression of the endogenous gene(s) is lowered.

(21) A method for producing a protein comprising: culturing the cell according to any of (13) to (15) comprising the mouse artificial chromosome vector comprising an exogenous DNA sequence(s); and collecting the protein produced that is encoded by the DNA.

(22) A method for producing a human antibody or antibodies comprising: using the non-human animal according to (19) comprising the mouse artificial chromosome vector comprising human antibody heavy chain and light chain genes or gene loci to produce the human antibody or antibodies; and collecting the human antibody or antibodies.

(23) The method according to (22), wherein the human antibody light chain gene or gene locus are the human antibody λ and κ light chain gene or gene locus.

The description of the present application includes the contents disclosed in Japanese Patent Application No. 2018-050178 from which the present application claims priority.

Effect of the Invention

The present invention provides novel mouse artificial chromosome vectors that are stable in rodent tissues and are derived from mouse chromosome 10 and mouse chromosome 16. Use of such vectors enables production of rodents, such as mice and rats, capable of producing human antibodies and production of human antibodies using such rodents.

EMBODIMENTS OF THE INVENTION

Figure 1:
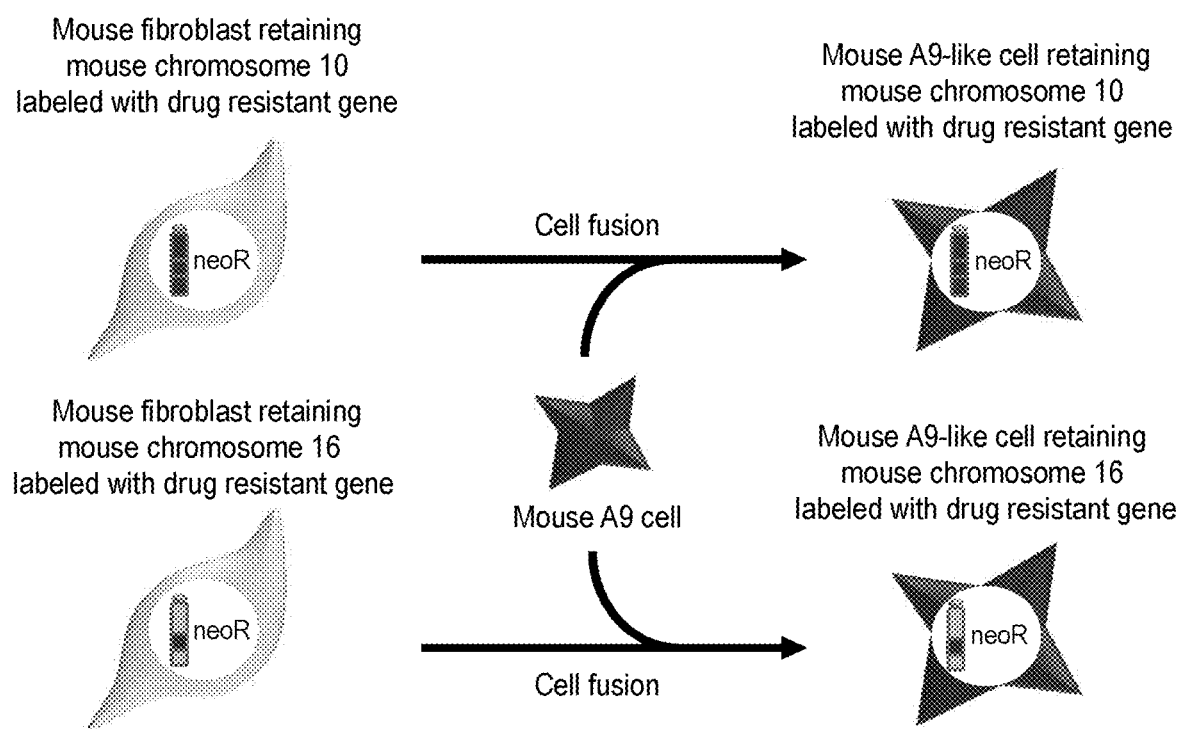
FIG. 1 shows preparation of A9-like cells that retain mouse chromosomes by subjecting a mouse embryonic fibroblast retaining mouse chromosome 10 or 16 labeled with a drug resistant gene to fusion to a mouse A9 cell.

The present invention will be further described in more detail.

As described above, the present invention provides a mouse artificial chromosome vector comprising: a natural centromere derived from a mouse chromosome selected from the group consisting of mouse chromosome 10 and mouse chromosome 16; a mouse-chromosome-10-derived long-arm fragment formed by deleting a long-arm region distal from the gene Gm8155 (NCBI: NC_000076.6), which is a mouse chromosome 10 long-arm site proximal to the centromere, or a mouse-chromosome-16-derived long-arm fragment formed by deleting a long-arm region distal from the gene Gm35974 (NCBI: NC_000082.6), which is a mouse chromosome 16 long-arm site proximal to the centromere; and a telomere sequence, wherein the vector is stably retained in a rodent cell, tissue, or individual and is capable of transmission to progeny.

As used herein, the term "natural centromere derived from a mouse chromosome" refers to the entire centromere (or the intact centromere) of mouse chromosome 10 or mouse chromosome 16. Thus, the centromere does not include a structure having centromere functions, which is obtained spontaneously or synthetically by using a portion of the centromere sequence of a mouse chromosome, as well as the centromere of a chromosome derived from other animals.

As used herein, the term "mouse artificial chromosome" or "mouse artificial chromosome vector" refers to an artificial chromosome constructed by a top-down approach, but it does not mean an artificial chromosome constructed by a bottom-up approach. The top-down approach refers to an approach in which a gene region is deleted from a natural chromosome by chromosomal modification, and a natural centromere is used to constitute a part of an artificial chromosome vector. The bottom-up approach refers to an approach in which a portion of a centromere sequence is obtained as a cloned DNA, which is then transfected into a mammalian cell to construct an artificial chromosome having centromere functions. This method is not employed herein.

As used herein, the "long-arm fragment derived from mouse chromosome 10 (or 16) formed by deleting a long-arm region distal from the gene Gm8155 (or Gm35974), which is a chromosome long-arm site of mouse chromosome 10 (or 16) proximal to the centromere" refers to a long-arm fragment on the centromere side, obtained by deleting a long arm distal region that is an upstream region of the gene Gm8155 (or the gene Gm35974) at a long arm site proximal to the centromere so as to substantially remove endogenous genes in the mouse chromosome, for the following reasons. That is, it is desirable to eliminate effects of endogenous genes as much as possible, so as to stably keep the vector of the present invention in cells or tissues of a rodent individual such as mouse or rat, and so as not to prevent the development of a rodent individual or the transmission to progeny. Here, the term "substantially removed" means that at least 99.5%, preferably at least 99.7%, more preferably 99.8%, and most preferably 99.9% to 100% of the total endogenous genes (or the number of genes) are removed from the mouse chromosome 10 or mouse chromosome 16. Further, the term "upstream region" refers to the 5'-terminal region of the said gene, preferably a region from the transcription initiation site to the terminal end of the 5'-untranslated region.

When the mouse artificial chromosomes are stably retained in a cell, tissue, or individual of a rodent such as a mouse or rat, the term "retention rate" used herein refers to a rate of cells having an artificial chromosome in cultured cells or in tissue or cells of a rodent.

The term "stably retained" as used herein means that it is difficult to cause deletion of the chromosome vector during cell division, i.e. that the chromosome vector is stably retained in cells even after cell division, thus the chromosome vector is efficiently transmitted to daughter cells or offspring mice.

In the case of an artificial chromosome vector derived from a fragment of mouse chromosome 10, the above-mentioned long-arm fragment consists of a long-arm fragment formed by deleting a region distal from, for example, the marker gene Gm8155 of the chromosome 10, although the fragment is not limited thereto. In the case of an artificial chromosome vector derived from a fragment of mouse chromosome 16, the long-arm fragment consists of a long-arm fragment formed by deleting a region distal from the marker gene Gm35974 of the chromosome 16. Alternatively, the long arm fragment comprises, as the basic structure, the mouse artificial chromosome contained in the deposited cell line DT40 (10MAC) T5-26 (Accession Number: NITE BP-02656) or deposited cell line DT40 (16MAC) T1-14 (Accession Number: NITE BP-02657). Such basic structure may further comprise a DNA sequence insertion site(s), such as loxP or FRT, at which an exogenous DNA or gene or gene locus is to be inserted.

The vector of the present invention may comprise a site at which an exogenous DNA or gene sequence is to be inserted. By incorporating an exogenous DNA or gene or gene locus of interest at such a site, it becomes possible to express the exogenous DNA or gene or gene locus when the vector is introduced into any cell, thus it is possible to use for various applications, including production of proteins, screening of therapeutic drugs, test of drug metabolism, analysis of DNA functions, gene therapy, and creation of useful non-human animals.

As used herein, the term "DNA" is used for any kind of DNA nucleic acid, including a gene or gene locus, cDNA, or chemically modified DNA, unless otherwise specified.

As used herein, the term "exogenous gene" or "exogenous DNA" means a gene or DNA of interest that is inserted at a gene insertion site of the vector and is carried in the vector, i.e., a gene or DNA or sequence thereof that is originally absent in cells of interest and is intended to be expressed in the cells.

The term "DNA sequence insertion site" used herein refers to a site of an artificial chromosome into which a DNA (e.g., a gene or a gene locus) sequence of interest may be inserted, such as a recognition site for a site-directed recombinase. Examples of such recognition sites include, but are not limited to, loxP (a Cre recombinase recognition site), FRT (an Flp recombinase recognition site), φC31attB and φC31attP (φC31 recombinase recognition sites), R4attB and R4attP (R4 recombinase recognition sites), TP901-1attB and TP901-1attP (TP901-1 recombinase recognition sites), and Bxb1attB and Bxb1attP (Bxb1 recombinase recognition sites).

The term "site-directed recombinase" used herein refers to an enzyme that induces recombination with a target DNA sequence specifically at the recognition site of the enzyme. Examples thereof include Cre integrase (also referred to as "Cre recombinase"), Flp recombinase, φC31 integrase, R4 integrase, TP901-1 integrase, and Bxb1 integrase.

The vector of the present invention is used to modify mouse chromosomes and to prepare a vector using the mouse-derived natural centromere in an intact state.

As useful properties of the vector of the present invention, the vector retention rate increases in cells or tissues of rodents, such as mice, rats, and hamsters, the vector is stably retained in cells, and a gene (or genes) of interest is/are carried in cells for a longer period. As such, the amount of a transgene does not vary among rodent individuals or tissues, and the transgene can be expressed for an extended period. In addition, efficiency of transmission to progeny and development of rodent individuals via pluripotent cells (e.g., ES cells or iPS cells) can be improved. The retention rate is approximately 90% or more in any tissue tested (e.g., tissues derived from the liver, intestine, kidney, spleen, lung, heart, skeletal muscle, brain, or bone marrow), and the mouse artificial chromosome of the present invention can also proliferate efficiently and can carry a plurality of (or multiple) copies in a cell.

Sequence information of mouse chromosomes 10 and 16 is available from DDBJ/EMBL/GenBank, chromosome databases at Santa Cruz Biotechnology, Inc., and other organizations.

The term "long arm" of a chromosome used herein refers to a chromosome region comprising a region of genes from the centromere side in a mouse chromosome. Meanwhile, the mouse chromosome has substantially no short arm.

The term "distal" region used herein refers to a region distal from the centromere (i.e., a region of the telomere side). On the other hand, a region near the centromere (i.e., a region of the centromere side) is referred to as the "proximal" region. The long-arm distal region is closer to the telomere than a specific cleavage site of the long arm, and the long-arm proximal region is closer to the centromere than a specific cleavage site of the long arm. This specific cleavage site is a position at which at least 99.5%, preferably at least 99.7%, more preferably 99.8%, and most preferably 99.9 to 100% of all endogenous genes (or the number of all endogenous genes) that are present in the long arm of mouse chromosome 10 or mouse chromosome 16 are deleted.

The term "telomere sequence" used herein refers to a natural telomere sequence derived from the same or different species or an artificial telomere sequence. In the case of the same species, the animal is of the same species with the mouse from which a chromosome fragment of an artificial chromosome vector is derived. In contrast, the different species is a mammal other than the mouse (including a human). Also, the artificial telomere sequence is an artificially prepared sequence having a telomere function, such as a (TTAGGG)n sequence (in which "n" indicates the number of repetitions). A telomere sequence can be introduced into an artificial chromosome by telomere truncation (i.e., substitution of a telomere sequence) as disclosed in, for example, WO 00/10383. The telomere truncation can be employed to shorten a chromosome during preparation of the artificial chromosome of the present invention.

The term "non-human animal" used herein includes mammalian animals excluding a human. For example, the mammalian animals includes, but are not limited to, primates such as human, monkey, and chimpanzee, rodents such as mouse, rat, hamster, and guinea pig, and ungulates such as cow, pig, sheep, and goat.

The term "embryonic stem cell" or "ES cell" used herein refers to a semi-immortalized pluripotent stem cell that is established from an inner cell mass of a blastocyst of a fertilized egg derived from a mammal (M. J. Evans and M. H. Kaufman, 1981, Nature 292: 154-156; J. A. Thomson et al., 1999, Science 282: 1145-1147; J. A. Thomson et al., 1995, Proc. Natl. Acad. Sci. U.S.A., 92: 7844-7848; J. A. Thomson et al., 1996, Biol. Reprod., 55: 254-259; J. A. Thomson and V. S. Marshall, 1998, Curr. Top. Dev. Biol. 38: 133-165). Cells having properties equivalent to those of such cells and artificially induced by reprogramming of somatic cells are "induced pluripotent stem cells" or "iPS cells" (K. Takahashi and S. Yamanaka, 2006, Cell 126: 663-676; K. Takahashi et al., 2007, Cell 131: 861-872; J. Yu et al., 2007, Science 318:1917-1920).

<Preparation and Use of Mouse Artificial Chromosome Vector>

Hereafter, production of the mouse artificial chromosome vector of the present invention and use of the same will be described. Specifically, the procedures are described in the working examples and the drawings below.

(1) Preparation of Mouse Artificial Chromosome Vector

The artificial chromosome vector of the present invention may be prepared by a method comprising the following steps of:
 (a) obtaining a cell comprising a mouse chromosome;
 (b) deleting a long-arm distal region of the mouse chromosome so as to exclude a majority of endogenous genes (the number of endogenous genes; i.e., 99.5% to 100%); and
 (c) inserting one or more DNA sequence insertion sites into a long-arm proximal region. The order of the steps (b) and (c) may be interchangeable.

Step (a):

In order to prepare the artificial chromosome vector of the present invention, a cell comprising a mouse chromosome is first to be produced. For example, a mouse embryonic fibroblast (mChr11-neo), which is a mouse fibroblast comprising a mouse chromosome labeled with a drug resistance gene (e.g., a G418-resistant neo gene), is subjected to cell fusion to a mouse A9 (BSr), which is a mouse A9 cell (ATCC VA20110-2209) comprising a blasticidin S-resistant BSr gene introduced thereinto. Next, the mouse A9 hybrid cell comprising a mouse chromosome labeled with a drug resistance gene; i.e. the mouse A9× mouse embryonic fibroblast (BSr; mChr-neo), is used to transfer the chromosome into a cell having a high homologous recombination rate. Thus, the cell comprising a mouse chromosome can be prepared. The mouse fibroblast is available based on procedures described in literatures. For example, the mouse fibroblast can be established from ICR or C57B6 mice commercially available from CLEA Japan, Inc. An example of an available cell having a high homologous recombination rate is a chicken DT40 cell (Dieken et al., Nature Genetics, 12, 1 74-182, 1996). Furthermore, the above-described transfer can be performed using known chromosome transfer techniques, such as microcell fusion (Koi et al., Jpn. J. Cancer Res., 80, 413-418, 1973).

Step (b):

In a cell having a single mouse-derived chromosome, a long-arm distal region of the mouse chromosome is deleted. It is important to delete (or remove or cleave out) a majority of endogenous genes present in the long arm and then to construct an artificial chromosome comprising the mouse centromere. That is, it is important to determine a cleavage site so as to delete (or remove or cleave out) a region containing at least 99.5%, preferably at least 99.7%, more preferably at least 99.8%, and most preferably 99.9 to 100% of all endogenous genes present in the long arm. Thus, a cell, tissue, or individual, which comprises the artificial chromosome introduced thereinto and is derived from a rodent (preferably a mouse or rat) can stably retain the artificial chromosome at a high retention rate, and it can be used for precise analysis of a gene (or genes) of interest and for material production. The above-described endogenous genes can be deleted by, for example, telomere truncation described in WO 00/10383. Specifically, a targeting vector comprising an artificial telomere sequence is constructed and is used to obtain a clone into which an (artificial) telomere sequence has been inserted at a target position on the chromosome by homologous recombination in a cell comprising a mouse chromosome. Thus, a deletion mutant can be obtained by telomere truncation. That is, the target position (or site) is a cleavage position of a long-arm distal region to be deleted. The artificial telomere sequence is inserted into this position by substitution via homologous recombination, so that the long-arm distal region is deleted. This position can be appropriately determined depending on a target sequence design when constructing a targeting vector. In the examples below, for example, a target sequence is designed based on the DNA sequence of the mouse chromosome 10 long arm NC_000076.6 (GenBank Accession Number) and the DNA sequence of the mouse chromosome 16 long arm NC_000082.6 (GenBank Accession Number), so that the telomere truncation occurs at a position closer to the telomere than the target sequence. As a result, a fragment of mouse chromosome 10 or mouse chromosome 16 resulting from deletion of a majority of endogenous genes can be obtained.

Step (c):

As a DNA sequence insertion site, a recognition site for a site-directed recombinase can be preferably inserted. Specifically, the phenomenon such that a certain enzyme recognizes a specific recognition site and causes DNA recombination specifically at the recognition site is known. The mouse artificial chromosome vector of the present invention can use a system having such an enzyme and its recognition site to insert or incorporate a gene or DNA sequence of interest. Examples of such system include, but are not limited to, a system having bacteriophage P1-derived Cre enzyme and its recognition site, i.e., the loxP sequence (a Cre/loxP system; B. Sauer in Methods of Enzymology, 1993, 225, 890-900), a system having budding yeast-derived Flp enzyme and its recognition site, i.e., FRT (Flp Recombination Target) sequence (a Flp/FRT system), a system having *Streptomyces* phage-derived φC31 integrase and its recognition site, i.e., φC31 attB/attP sequence, a system having R4 integrase and its recognition site, i.e., R4 attB/attP sequence, a system having TP901-1 integrase and its recognition site, TP901-1 attB/attP sequence, and a system having Bxb1 integrase and its recognition site, i.e., Bxb1 attB/attP sequence, provided that the system can function as a DNA sequence insertion site.

In order to insert a recognition site for such a site-directed recombinase, known methods, such as homologous recombination, can be employed. The position and the number of insertion can be appropriately determined in a long-arm proximal region and a short-arm proximal region.

According to the present invention, one of certain recognition sites or different recognition sites can be inserted. The design of a recognition site enables identification of an insertion site for an exogenous gene or exogenous DNA, so that the insertion site is fixed and no unexpected positional effects are thus exerted. In the case of mouse artificial chromosomes as illustrated in Examples below, a gene inserted into a loxP sequence that is a recognition site for a site-directed recombinase on the mouse chromosome can be expressed in a tissue-specific manner.

Preferably, a reporter gene may be inserted into the mouse artificial chromosome vector of the present invention having a DNA sequence insertion site in advance while maintaining an insertion site for a target gene or DNA sequence. Examples of reporter genes include, but are not particularly limited to, a fluorescent protein gene (e.g., a green fluorescent protein (GFP or EGFP) gene or a yellow fluorescent protein (YFP) gene), a tag-protein-encoding DNA, a β-galactosidase gene, and a luminescent gene (e.g., a luciferase gene), with GFP or EGFP being preferable.

The mouse artificial chromosome vector of the present invention may further comprise a selection marker gene. A selection marker is effective when selecting a cell transformed with the vector. As a selection marker gene, for example, either or both of a positive selection marker gene and a negative selection marker gene may be used. Examples of positive selection marker genes include drug-resistant genes such as a neomycin-resistant gene (Neo or NeoR), an ampicillin-resistant gene, a blasticidin S (BS)-resistant gene, a puromycin-resistant gene (Puro), a geneticin (G418)-resistant gene, and a hygromycin-resistant gene (Hyg). In addition, examples of negative selection marker genes include a herpes simplex thymidine kinase (HSV-TK) gene and a diphtheria toxin A fragment (DT-A) gene. In general, HSV-TK is used in combination with ganciclovir or acyclovir.

Homologous recombination can be preferably used as a technique for inserting a reporter gene or a target exogenous gene or DNA into the mouse artificial chromosome vector of the present invention. Homologous recombination can be performed using a targeting vector, which is obtained by ligating a DNA cassette to be inserted between sequences (5' arm and 3' arm) homologous to nucleotide sequences of 5' and 3' regions (each having approximately 1 to 6 kb, preferably approximately 2 to 4 kb) at an insertion position of the mouse chromosome. Examples of vectors that can be used for this purpose include plasmid vectors, phage vectors, cosmid vectors, and viral vectors, with the plasmid vectors being preferable. Examples of basic plasmids for targeting vector construction include, but are not limited to, V907 and V913 (Lexicon Genetics). The basic vector may comprise one sequence or element or two or more sequences or elements, such as a promoter, an enhancer, a selection marker gene, or a replication origin, that are generally inserted when vectors are constructed. Examples of promoters may include phosphoglycerate kinase (PGK) promoter, chicken beta actin (CAG) promoter, Cytomegalovirus (CMV) promoter, and elongation factor 1α (EF1α) promoter.

The mouse artificial chromosome vector prepared by the method described above comprises a mouse-derived chromosome fragment (which comprises a natural centromere, a long-arm fragment formed by deleting at least 99%, and preferably at least 99.5% of endogenous genes, and a short arm (if present)), and an artificial telomere sequence. The above centromere constitutes the entire mouse chromosome centromere structure, which is used to prepare the artificial chromosome.

Examples of the mouse artificial chromosome vector of the present invention include the mouse artificial chromosome vectors prepared in Examples below. Such artificial chromosomes are a vector produced by deleting a long-arm distal region of mouse chromosome 10 that is a region upstream of the gene Gm8155, and a vector produced by deleting a long-arm distal region of mouse chromosome 16 that is a region upstream of the gene Gm35974. These vectors each comprise, as the basic structure, the mouse artificial chromosome contained in the deposited cell line DT40 (10MAC) T5-26 (Accession Number: NITE BP-02656) and the deposited cell line DT40 (16MAC) T1-14 (Accession Number: NITE BP-02657). Because of such basic structure, for example, a DNA sequence insertion site(s), a selection marker gene(s), or an exogenous gene(s) (or DNA(s)) as described below may be inserted into the DNA structure of the basic structure.

The above mouse artificial chromosome vector preferably comprises one or more DNA sequence insertion sites, such as a recognition site for site-directed recombinase (e.g., a loxP sequence, which is a Cre enzyme recognition site). Examples of recognition sites for the site-directed recombinase include, but are not limited to, loxP sequences of GFP-PGKneo-loxP-3' HPRT type, 5' HPRT-loxP-hyg type, PGKneo-loxP-3' HPRT type, and GFP-5' HPRT-loxP-PGKhyg type. In the above, "GFP" represents a green fluorescent protein gene, "PGKneo" represents a phosphoglycerate kinase promoter/neomycin-resistant gene cassette, "HPRT" represents a hypoxanthine-guanine phosphoribosyltransferase gene, and "hyg" represents a hygromycin-resistant gene.

The above-described mouse artificial chromosome vector may further comprise a reporter gene(s) or a selection marker gene(s) (e.g., a positive selection marker gene(s) or a negative selection marker gene(s)).

The mouse artificial chromosome vector may further comprise an exogenous gene(s) or DNA sequence(s).

Examples of the exogenous gene or DNA include, but are not limited to, human genes or DNAs, including DNAs consisting of genes or gene loci of the human chromosome long arm or short arm (see (2) below).

The advantages of the mouse artificial chromosome vector of the present invention include advantages of conventional artificial chromosome vectors as follows: 1) the vector is not inserted into a host chromosome but is independently maintained, so that a host gene is not disrupted; 2) the vector is stably retained at a certain copy number (which may be a plurality of (or multiple) copies) and is exposed to the physiological expression regulation of a host cell, so that the overexpression or quenching of expression of an inserted gene is not caused; 3) a size of DNA that can be introduced is not limited, so that an expression regulatory region-containing gene or a plurality of genes/isoforms can be introduced; a vector retention rate in a rodent cell or individual is increased, compared with that of conventional artificial chromosomes; a transgene can be stably expressed for a long period of time and a rate of transmission of the vector to offspring (or progeny) is improved, so that efficiency for transgenic mouse production is improved; and 4) because of less variation among tissues after introduction of the vector, that is, a retention rate is approximately 90% or higher in any tissue.

(2) Introduction of Exogenous Gene or DNA

An exogenous gene or DNA can be introduced into the mouse artificial chromosome vector of the present invention.

The size of the exogenous gene or DNA sequence is not particularly limited, and it may be 20 kb or less or may exceed 20 kb, such as 50 kb or more, 100 kb or more, 200 kb or more, 500 kb or more, 700 kb or more, 1 Mb or more, 10 Mb or more, 20 Mb or more, 30 Mb or more, 40 Mb or more, or 50 Mb or more. The vector of the present invention can carry an exogenous DNA (a chromosome fragment) of 1 Mb or more, which is difficult to be carried by artificial chromosome vectors such as BAC, PAC, and YAC vectors.

Moreover, the vector of the present invention can stably retain a large-size exogenous gene or DNA of 200 kb or more, such as 1 Mb or more, at a high retention rate in rodent cells, tissues, or individuals.

An embodiment of the present invention provides a vector that enables a rodent cell, tissue, or individual to stably maintain a large-size exogenous gene or DNA of 200 kb or more at a retention rate of 90% or more therein. Another embodiment of the present invention provides a method for preparing such vector.

The exogenous gene or DNA includes, but is not limited to, nucleic acids derived from organisms other than rodents such as mouse and rat. It may be genes or DNAs derived from any organism, tissue, or cell, preferably genes or DNAs derived from mammals, more preferably genes or DNAs derived from human. Examples of the genes or DNAs include, but are not limited to, genes or DNAs encoding polypeptides such as cytokines, hormones, growth factors, neurotrophic factors, hematopoietic factors, immunoglobulins, G protein-coupled receptors, and enzymes, genes or DNAs used for treatment of various diseases such as tumor, muscular dystrophy, hemophilia, neurodegenerative diseases (e.g., Alzheimer's disease, Huntington's disease, and Parkinson's disease), autoimmune diseases, allergic diseases, genetic diseases, infectious diseases, obstructive arteriosclerosis, cystic fibrosis, and adenosine deaminase (ADA) deficiency, genes or DNAs involved in the immune system such as T cell receptors (TCR) and human leukocyte antigens (HLA), genes or DNAs encoding (human) drug-metabolizing enzymes, genes or DNAs involved in (human) drug metabolism, human chromosome long-arm and short-arm DNAs, and (human) genomic libraries.

Examples of the cytokines include interferons (e.g., IF-α, IF-β, and IF-γ), interleukins (e.g., IL-1, IL-2, IL-4, IL-6, IL-11, and IL-12), tumor necrosis factors (e.g., TNF-α and TNF-β), and TGF-β family proteins (e.g., bone morphogenic protein (BMP)).

Examples of the hormones include growth hormones, human chorionic gonadotropin (hCG), human placental lactogen (hPL), human pituitary gonadotropic hormone, thyroid-stimulating hormone (TSH), luteinizing hormone-releasing factor, insulin, glucagon, somatostatin, and prolactin.

Examples of the growth factors or neurotrophic factors include insulin-like growth factor, brain-derived neurotrophic factor (BDNF), albumin-fused ciliary neurotrophic factor, platelet-derived neurotrophic factor (PDNF), transforming growth factor, nerve growth factor (NGF), and TNF growth factor.

Examples of the coagulation or hemolysis factors include Factor VII, Factor VIII, Factor X, and t-PA.

Examples of the hematopoietic factors include erythropoietin, (granulocyte) colony-stimulating factor, and thrombopoietin.

Examples of the G protein-coupled receptors include adrenergic receptor, muscarinic acetylcholine receptor, adenosine receptor, GABA receptor (type B), angiotensin receptor, cholecystokinin receptor, dopamine receptor, glucagon receptor, histamine receptor, odorant receptor, opioid receptor, secretin receptor, somatostatin receptor, gastrin receptor, and P2Y receptor.

Examples of the enzymes include asparaginase, superoxide dismutase, uricase, streptokinase, dopamine synthase, and adenosine deaminase.

Examples of the genes used for treatment of various diseases such as tumor, muscular dystrophy, neurodegenerative diseases (e.g., Alzheimer's disease, Huntington's disease, and Parkinson's disease), autoimmune diseases, allergic diseases, and genetic diseases include dystrophin gene, IL-12 gene, TNF-α gene, tumor suppressor genes, dopamine synthase gene, and genetically deficient enzyme genes (e.g., adrenal enzyme genes, such as cytochrome enzyme (P450) gene, 3β-hydroxysteroid dehydrogenase gene, and 21 hydroxylase (P450 c21) gene).

Examples of immune system genes include genes or DNAs encoding proteins involved in the immune system, such as T cell receptors (TCRs), human leukocyte antigens (HLAs), Fcγ receptors (FCGRs), killer cell Ig-like receptors (KIRs), and leukocyte Ig-like receptors (LILRs).

The drug-metabolizing enzymes are involved in the metabolic reactions to degrade or excrete xenobiotics such as drugs or toxins. Examples of the enzymes include enzymes involved in the phase I reaction (e.g., oxidation, reduction, and hydrolysis) and the phase 11 reaction (conjugation). Examples of the enzymes involved in the phase I reaction include known enzymes such as cytochrome P450 ("CYP"), specifically, CYP1A, CYP1B, CYP2A, CYP2B, CYP2C, CYP2D, CYP2E, CYP2J, CYP3A, CYP4A, CYP4B, and subfamilies thereof, and CESs. With regard to the CYP subfamily, examples of the CYP3A subfamily include CYP3A4, CYP3A43, CYP3A5, and CYP3A7. Examples of the CYP2C subfamily include CYP2C8, CYP2C9, CYP2C18, and CYP2C19. Examples of the enzymes involved in the phase II reaction (conjugation) include UGT1 and UGT2.

Examples of the drug metabolism-related genes include genes encoding transporters and genes encoding nuclear receptors. Examples of the genes encoding transporters include MDR1, MDR2, MRP2, OAT, OATP, OCT, and BCRP. Examples of the genes encoding nuclear receptors include PXR, AhR, CAR, and PPARα.

As described above, a drug-metabolism-related exogenous DNA sequence that may be introduced into the vector of the present invention can comprise at least one gene sequence or at least two gene sequences selected from the group consisting of genes encoding enzymes involved in the phase I reaction, genes encoding enzymes involved in the phase II reaction, genes encoding transporters, and genes encoding nuclear receptors.

Genes or DNAs encoding immunoglobulins are preferably human antibody genes or gene loci. Specific examples thereof include human immunoglobulin heavy chain gene or gene locus, human immunoglobulin light chain gene or gene locus, and DNAs of the heavy chain and light chain genes or gene loci. The light chain gene(s) or gene locus or loci is/are the λ light chain gene or gene locus and/or the κ light chain gene or gene locus.

The term "human antibody gene or gene locus" used herein refers to the human antibody heavy chain gene or gene locus derived from human chromosome 14, the human antibody light chain κ gene or gene locus derived from human chromosome 2, and/or the human antibody light chain λ gene or gene locus derived from human chromosome 22, unless otherwise specified. Specifically, the human antibody gene or gene locus is represented by the nucleotide sequence as shown in, for example, the immunoglobulin heavy gene locus (human) NC_000014.9 (nucleotide numbers 105586437 . . . 106879844) or (nucleotide numbers 105264221 . . . 107043718)) of human chromosome 14, the immunoglobulin kappa gene locus (human) NC_000002.12 (nucleotide numbers 88857361 . . . 90235368) or (nucleotide numbers 88560086 . . . 90265666) of human chromosome 2, or the immunoglobulin lambda gene locus (human) NC_000022.11 ((nucleotide numbers 22026076 . . . 22922913) or (nucleotide numbers 21620362 . . . 23823654) of human chromosome 22. The nucleotide length of the human antibody heavy chain gene or gene locus is approximately 1.3 Mb, that of the human antibody light chain κ gene or gene locus is approximately 1.4 Mb, and that of the human antibody light chain λ gene or gene locus is approximately 0.9 Mb.

The mouse antibody heavy chain gene or gene locus is present on mouse chromosome 12, the mouse antibody light chain κ gene or gene locus is present on mouse chromosome 6, and the mouse antibody light chain λ gene or gene locus is present on mouse chromosome 16. Specifically, the mouse antibody heavy chain gene or gene locus is represented by, for example, the nucleotide sequence of Chromosome 12, NC_000078.6 (113258768 . . . 116009954, complement), the mouse antibody light chain κ gene or gene locus is represented by the nucleotide sequence of Chromosome 6, NC_000072.6 (67555636 . . . 70726754), and the mouse antibody light chain λ gene or gene locus is represented by the nucleotide sequence of Chromosome 16, NC_000082.6 (19026858 . . . 19260844, complement).

The rat antibody heavy chain gene or gene locus is present on rat chromosome 6, the rat antibody light chain κ gene or gene locus is present on rat chromosome 4, and the rat antibody light chain λ gene or gene locus is present on rat chromosome 11. The nucleotide sequences of these genes or gene loci are available from, for example, U.S. NCBI (e.g., GenBank) and known literature.

In the present invention, the mouse artificial chromosome vector comprising the human antibody genes is: a mouse artificial chromosome vector comprising the human antibody heavy chain gene or gene locus derived from human chromosome 14 and the human antibody light chain κ gene or gene locus derived from human chromosome 2; a mouse artificial chromosome vector comprising the human antibody heavy chain gene or gene locus derived from human chromosome 14 and the human antibody light chain λ gene or gene locus derived from human chromosome 22; or a mouse artificial chromosome vector comprising all of the human antibody heavy chain gene or gene locus derived from human chromosome 14, the human antibody light chain κ gene or gene locus derived from human chromosome 2, and the human antibody light chain λ gene or gene locus derived from human chromosome 22. Such vectors can be prepared by chromosome engineering techniques described herein.

The non-human animal of the present invention is: an animal that comprises a mouse artificial chromosome vector comprising the human antibody heavy chain gene or gene locus derived from human chromosome 14 and the human antibody light chain κ gene or gene locus derived from human chromosome 2 and a mouse artificial chromosome vector comprising the human antibody heavy chain gene or gene locus derived from human chromosome 14 and the human antibody light chain λ gene or gene locus derived from human chromosome 22; or an animal that comprises a mouse artificial chromosome vector comprising the human antibody heavy chain gene or gene locus derived from human chromosome 14, the human antibody light chain κ gene or gene locus derived from human chromosome 2, and the human antibody light chain λ gene or gene locus derived from human chromosome 22. Thus, the non-human animal enables production of a human antibody reacting with an antigenic substance when such antigenic substance is administered thereto.

As used herein, the term "human antibody" may be of any class and subclass of human immunoglobulin (Ig).

Examples of classes include IgG, IgA, IgM, IgD, and IgE, and examples of subclasses include IgG1, IgG2, IgG3, IgG4, IgA1, and IgA2. These classes and subclasses can be classified in accordance with differences in heavy chains. IgG chains are referred to as γ chains, IgG1 to IgG4 chains are referred to as γ1, γ2, γ3, and γ4 chains, respectively, and IgA, IgM, IgD, and IgE chains are referred to as α chains (α1 and α2), μ chain, δ chain, and ε chain, respectively. It is known that each antibody light chain comprises a κ chain and a λ chain and that, when reconstitution of the κ chain gene is not successfully completed during rearrangement of the immunoglobulin gene, the λ chain gene is reconstituted. The human antibody heavy chain gene locus comprises, in the 5' to 3' direction, a V (variable) region gene comprising VH1, VH2 . . . VHm (in which m is, for example, 38 to 46), a D (diversity) region gene comprising DH1, DH2 . . . DHn (in which n is, for example, 23), a J (joining) region gene comprising JH1, JH2 . . . JHr (in which r is 6), and a C (constant) region gene comprising Cμ, Cδ, Cγ3, Cγ1, Cα1, Cγ2, Cγ4, Cε, and Cα2. An antibody that is produced by rearrangement of the human immunoglobulin genes in the immune system is a human antibody.

A human antibody molecule is composed of 2 human antibody heavy chains and 2 human antibody light chains, wherein each heavy chain is bound to each light chain by 2 disulfide bonds, and 2 heavy chains are bound to each other by 2 disulfide bonds between constant (C) regions. In each variable (V) region of an antibody molecule, there are 3 complementarity-determining regions (CDRs) with particularly high degrees of mutations referred to as CDR1, CDR2, and CDR3 from the N terminus. Antibody-antigen binding properties vary depending on differences in sequences of the CDRs. It is known that antibody diversity arises from reconstitution of the immunoglobulin gene.

At least one insulator sequence may be present at a proximal region or both sides of the insertion site of an exogenous gene or DNA in the mouse artificial chromosome vector of the present invention. The insulator sequence exerts an enhancer blocking effect (i.e., adjacent genes do not affect each other) or a chromosome boundary effect (i.e., a region promoting gene expression is separated and distinguished from a region inhibiting the gene expression). Examples of such a sequence include human β-globin HS1 to HS5 and chicken β-globin HS4.

The exogenous gene or DNA can be introduced by using the above-described site-directed recombinase system, which is inserted as the DNA sequence insertion site. For example, a targeting vector comprising a loxP sequence which is the recognition site for Cre enzyme and an exogenous gene or DNA or a chromosome fragment comprising a loxP sequence which is the recognition site for Cre enzyme and an exogenous gene or DNA is constructed. The Cre enzyme is then expressed in a cell comprising the mouse artificial chromosome vector of the present invention to induce site-directed recombination at the loxP sequence with the targeting vector or the chromosome fragment. Thus, the exogenous gene or DNA can be introduced.

The mouse artificial chromosome vector of the present invention may comprise circular DNA comprising a recognition site(s) (e.g., a loxP sequence, an FRT sequence, etc.) that is for a site-directed recombinase(s) to be inserted thereinto. DNA cloned using a known vector such as a plasmid vector for *Escherichia coli* host or circular YAC for yeast host may be inserted. A preferable loxP sequence is a wild type sequence derived from P1 phage, and the insertion reaction of the circular insert into the loxP sequence on the artificial chromosome vector using the Cre enzyme is reversible. Once the circular insert is inserted, two loxP sequences are left on the artificial chromosome vector, and, because of this, when the Cre enzyme is expressed again, a reversible reaction that cleaves out the circular insert might occur, whereby further modification of the artificial chromosome vector, such as secondary insertion of the insert, becomes difficult. However, when a mutant loxP sequence with nucleotide substitution, or a combination of attB/attP sequences that are recognition sites for φC31 integrase, is/are used, a system into which a plurality of circular inserts are sequentially inserted can be constructed without causing the reversible reaction.

(3) Transfer of Mouse Artificial Chromosome Vector into Cell and Production of Non-Human Animal The mouse artificial chromosome vector of the present invention or the mouse artificial chromosome vector comprising an exogenous gene or DNA of the present invention can be transferred or introduced into any cell. Examples of methods therefor include microcell fusion, lipofection, a calcium phosphate method, microinjection, and electroporation, with microcell fusion being preferable.

The microcell fusion technique is a method for transferring the mouse artificial chromosome vector of the present invention into a target cell by microcell fusion between a cell comprising the mouse artificial chromosome vector of the present invention and capable of micronucleus formation (e.g., mouse A9 cell) and another target cell. The cell capable of micronucleus formation is treated with a polyploid inducer (e.g., colcemid or colchicine) to form a multinucleated cell having micronuclei. Then, the cell is subjected to cytochalasin treatment to form microcells and then to fusion to a target cell.

Examples of cells into which the vector can be introduced include animal cells, preferably mammalian cells including human cells, such as germline cells (e.g., oocytes and spermatocytes), stem cells (e.g., embryonic stem (ES) cells, germline stem (GS) cells, somatic stem cells), somatic cells, embryonal cells, adult cells, normal cells, disease cells, primary cultured cells, subcultured cells, and established cell lines. Examples of the stem cells include pluripotent stem cells (e.g., ES cells, embryonic germline (EG) cells, embryonic carcinoma (EC) cells, mGS cells, and human mesenchymal stem cells), induced pluripotent stem (iPS) cells, and nuclear transfer clone embryo-derived embryonic stem (ntES) cells. The preferred cells are selected from the group consisting of somatic cells derived from mammals (preferably rodents including mice), non-human germline cells, stem cells, and precursor cells. When the cell is derived from a mammal such as a rodent, the vector of the present invention is more stably retained in the cell or tissue of the mammal (e.g., a rodent such as a mouse) into which the vector of the present invention has been introduced. That is, vector drop-out from the cell is significantly decreased, or the drop-out would not take place.

Examples of cells include hepatocytes, enterocytes, renal cells, splenocytes, lung cells, cardiac cells, skeletal muscle cells, brain cells, bone marrow cells, lymphocytes, megakaryocytes, spermatocytes, and oocytes.

Examples of tissues include liver, intestine, kidney, thymic gland, spleen, lung, heart, muscle (e.g., skeletal muscle), brain, bone marrow, testis, and ovary tissues.

ES cells can be established and maintained as follows. That is, an inner cell mass is first removed from the blastocyst of a fertilized egg of an animal of interest, and the inner cell mass is then cultured using a mitomycin C-treated mouse embryonic fibroblast as a feeder. Thus, ES cells can be established and maintained (M. J. Evans and M. H. Kaufman, 1981, Nature 292, 154-156).

Induced pluripotent stem (iPS) cell colonies are generated in about 3 to 5 weeks by introducing specific reprogramming factors (DNAs or proteins) into a somatic cell (including a somatic stem cell) and subjecting the cell to culture and subculture in an appropriate medium. Examples of known combinations of reprogramming factors include: a combination of Oct3/4, Sox2, Klf4, and c-Myc; a combination of Oct3/4, Sox2, and Klf4; a combination of Oct4, Sox2, Nanog, and Lin28; and a combination of Oct3/4, Sox2, Klf4, c-Myc, Nanog, and Lin28 (K. Takahashi and S. Yamanaka, Cell 126, 663-676, 2006; WO 2007/069666; M. Nakagawa et al., Nat. Biotechnol., 26, 101-106, 2008; K. Takahashi et al., Cell 131, 861-872, 2007; J. Yu et al., Science 318, 1917-1920, 2007; J. Liao et al., Cell Res. 18, 600-603, 2008). For example, culture is conducted using a mitomycin C-treated mouse embryonic fibroblast cell line (e.g., STO) as a feeder cell, and culturing a somatic cell into which the vector has been introduced (approximately $10^4$ to $10^5$ cells/cm$^2$) at about 37° C. using an ES cell culture medium on the feeder cell layer. The feeder cell is not always necessary (Takahashi, K. et al., Cell 131, 861-872, 2007). Examples of the basic medium include Dulbecco's Modified Eagle's Medium (DMEM), Ham's F-12 medium, and a mixture thereof. As the ES cell culture medium, for example, a mouse ES cell culture medium or a primate ES cell culture medium (Reprocell Inc.) can be used.

ES cells and iPS cells are known to contribute to the germline transmission. Accordingly, a non-human animal (or a transgenic animal (excluding a human)) can be produced by a method comprising: introducing the mouse artificial chromosome vector of the present invention comprising the target gene or DNA into the ES cells or iPS cells; injecting the cells into the blastocyst of an embryo derived from the same mammalian species as that from which the cells are derived; transplanting the embryo into the uterus of a foster mother; and allowing the foster mother to give birth to offsprings. In addition, a male and a female of the resulting transgenic animals are subjected to crossbreeding with each other, so that homozygous animals and their offsprings can be further produced.

An exogenous gene or DNA, such as a human antibody gene, a gene for treatment of a disease, and a drug metabolism-related gene, is introduced into pluripotent cells such as ES cells and iPS cells or the above other cells via the mouse artificial chromosome vector of the present invention. Thus, a cell or non-human animal that can produce a human antibody is produced. In addition, a cell that can produce a therapeutic protein can be produced. Furthermore, a non-human animal model for a disease such as a drug metabolism-related disease can also be produced.

In some cases, it is preferable that such a non-human animal have a disrupted endogenous gene or decreased expression of the endogenous gene corresponding to the exogenous gene included in the mouse artificial chromosome vector. Gene targeting can be employed as the disruption technique. The RNAi or miRNA technique can be employed to decrease endogenous gene expression. Examples of such an exogenous gene include a drug metabolism-related gene and a human antibody gene. A non-human animal whose endogenous gene has been disrupted can be produced by crossbreeding between a non-human chimeric animal having the mouse artificial chromosome vector containing the exogenous gene or its offspring and a chimeric animal having a deletion of the entire cluster of the corresponding endogenous gene or its offspring to yield an animal having a heterozygous deletion of the endogenous gene, and by further crossbreeding between the heterozygous animals.

The cell or transgenic non-human animal having a mouse artificial chromosome vector can be produced by the above-described techniques. Specific examples of the non-human animal include a rodent, such as mouse or rat, comprising the mouse artificial chromosome vector.

Specifically, the present invention provides a cell or non-human animal comprising the mouse artificial chromosome vector.

In addition, the cell, tissue, or organ obtained from the non-human animal of the present invention can be used to produce a cell line that produces a protein expressed by the exogenous gene.

(4) Human Antibody-Producing Non-Human Animal

As described above, the non-human animal of the present invention is: an animal that comprises a mouse artificial chromosome vector comprising the human antibody heavy chain gene or gene locus derived from human chromosome 14 and the human antibody light chain κ gene or gene locus derived from human chromosome 2 and a mouse artificial chromosome vector comprising the human antibody heavy chain gene or gene locus derived from human chromosome 14 and the human antibody light chain λ gene or gene locus derived from human chromosome 2; or an animal that comprises a mouse artificial chromosome vector comprising the human antibody heavy chain gene or gene locus derived from human chromosome 14, the human antibody light chain κ gene or gene locus derived from human chromosome 2, and the human antibody light chain λ gene or gene locus derived from human chromosome 22.

Figure 17:
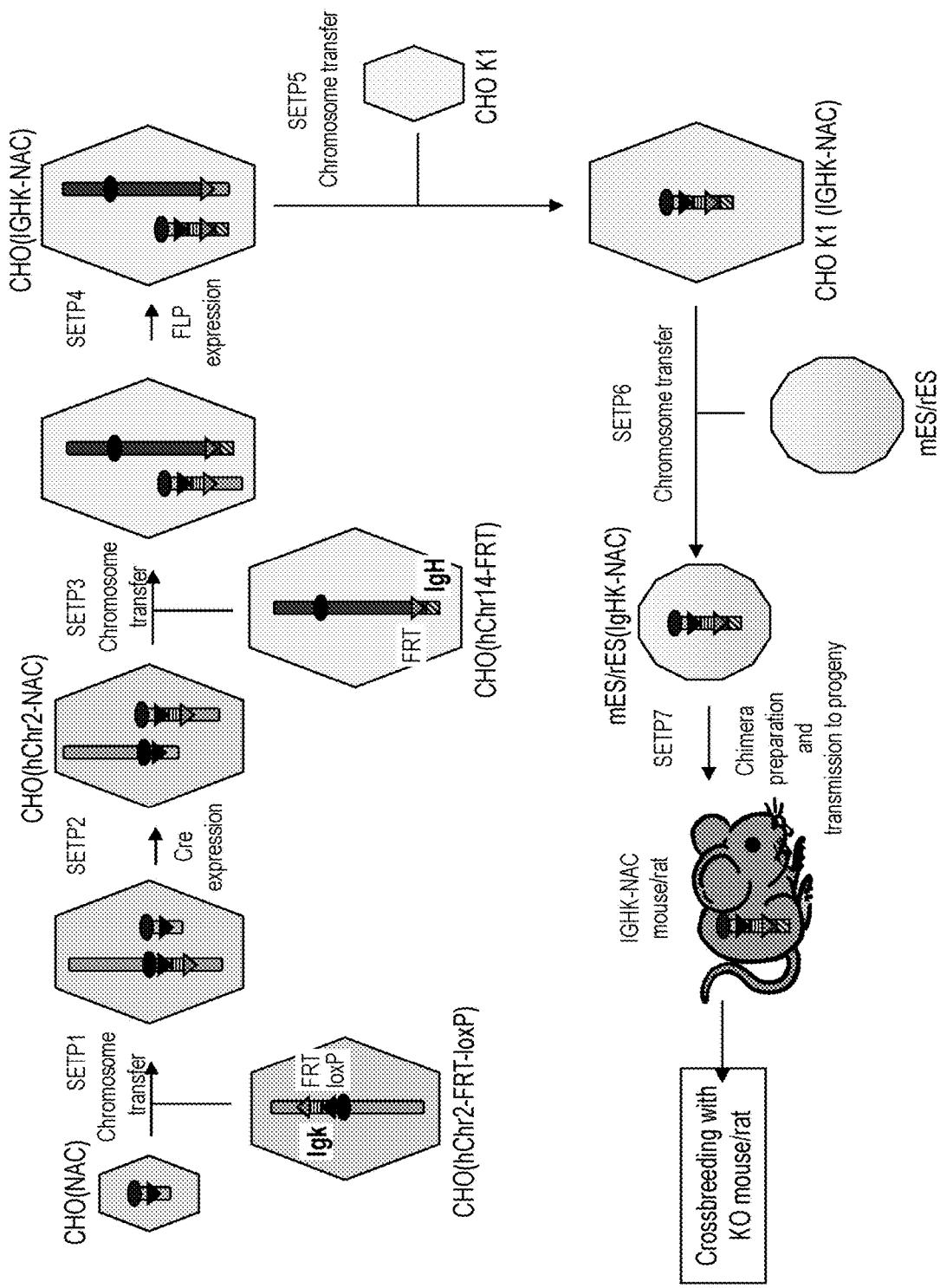
FIG. 17 schematically shows construction of IGHK-NAC and preparation of a human antibody-producing mouse or rat comprising IGHK-NAC.
Figure 21:
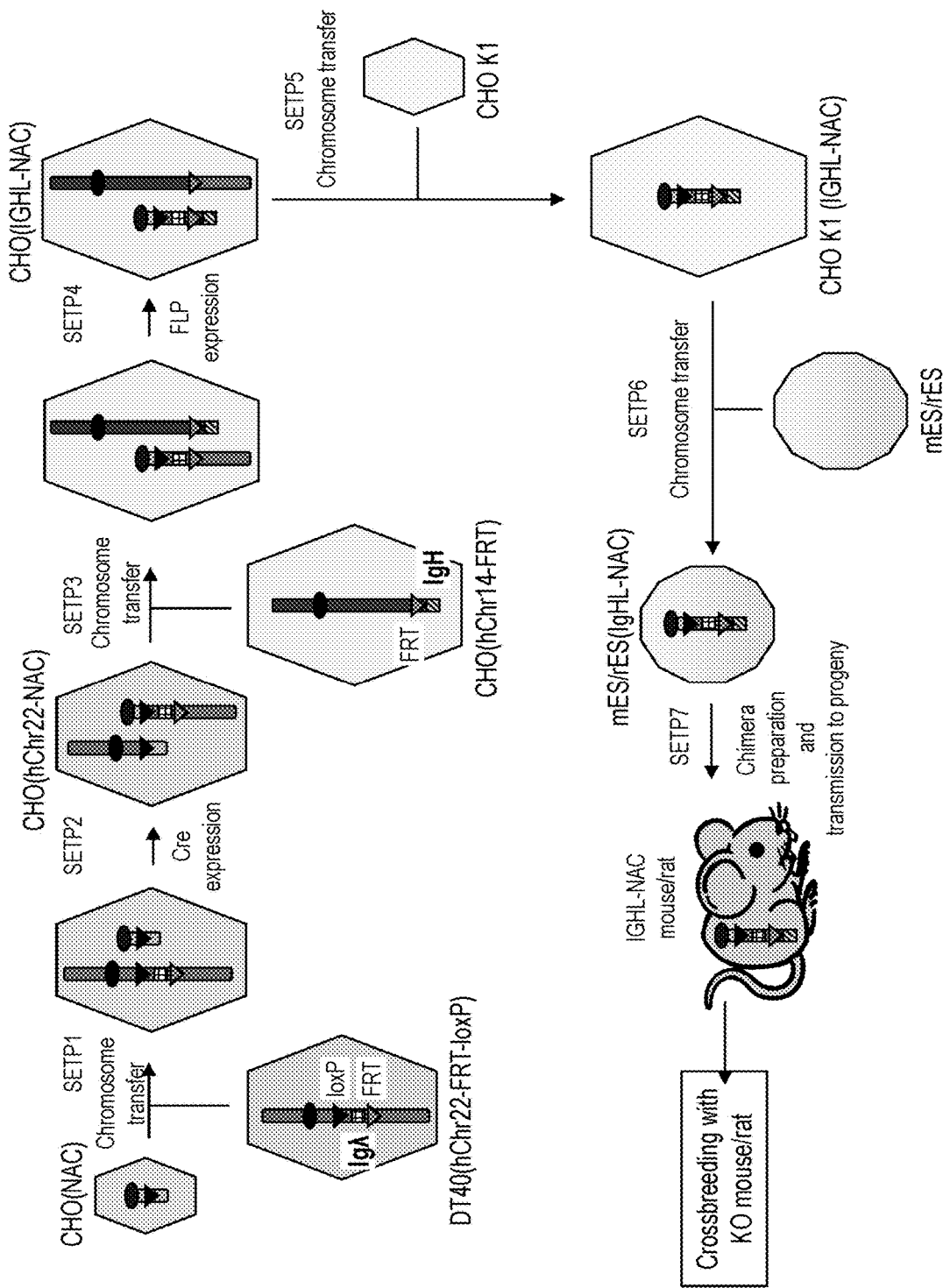
FIG. 21 schematically shows construction of IGHL-NAC and preparation of a human antibody-producing mouse or rat comprising IGHL-NAC.

Specifically, the non-human animal of the present invention (a mouse and a rat) capable of producing a human antibody can be prepared in accordance with the procedures shown in, for example, FIG. 17 and FIG. 21.

Hereafter, examples of the production of non-human animals using mouse artificial chromosomes are described.

Each of an animal cell comprising the human antibody light chain κ gene or gene locus derived from human chromosome 2 (e.g., DT40) and an animal cell comprising the human antibody light chain λ gene or gene locus derived from human chromosome 22 (e.g., DT40), both being modified by introduction of recognition sites for site-directed recombinases (e.g., loxP and FRT), is transferred into a rodent cell (e.g., CHO) comprising the mouse artificial chromosome (MACs) by cell fusion, and expression of a site-directed recombinase (e.g., Cre) is induced to prepare a rodent cell comprising a MAC comprising the human antibody light chain κ gene or gene locus and a rodent cell comprising a MAC comprising the human antibody light chain λ gene or gene locus.

The recognition site for a site-directed recombinase (e.g., FRT) is introduced into an area in the vicinity of the human antibody heavy chain gene or gene locus on human chromosome 14 retained in an animal cell (e.g., DT40), and the animal cell retaining the modified human antibody heavy chain gene or gene locus is transferred into a rodent cell (e.g., CHO) retaining MAC by cell fusion. Thus, a rodent cell comprising a MAC comprising the human antibody heavy chain gene or gene locus is prepared.

Each of the rodent cell comprising a MAC comprising the human antibody light chain κ gene or gene locus and the rodent cell comprising a MAC comprising the human antibody light chain λ gene or gene locus is subjected to fusion to the rodent cell comprising the human antibody heavy chain gene or gene locus to thereby transfer the MAC comprising the human antibody light chain κ gene or gene locus or the MAC comprising the human antibody light chain λ gene or gene locus into the rodent cell comprising the human antibody heavy chain gene or gene locus. Expression of a site-directed recombinase (e.g., FLP) is then induced to prepare the rodent cell comprising a MAC comprising the human antibody heavy chain gene or gene locus derived from human chromosome 14 and the human antibody light chain κ gene or gene locus derived from human chromosome 2 and the rodent cell comprising a MAC comprising the human antibody heavy chain gene or gene locus derived from human chromosome 14 and the human antibody light chain λ gene or gene locus derived from human chromosome 22.

Each of the rodent cell comprising a MAC comprising the human antibody heavy chain gene or gene locus derived from human chromosome 14 and the human antibody light chain κ gene or gene locus derived from human chromosome 2 and the rodent cell comprising a MAC comprising the human antibody heavy chain gene or gene locus derived from human chromosome 14 and the human antibody light chain λ gene or gene locus derived from human chromosome 22 is subjected to fusion to a pluripotent stem cell (e.g., an ES or iPS cell) of a non-human animal (e.g., a mouse or rat) by the microcell fusion technique to thereby produce a non-human animal pluripotent stem cell that comprises a MAC comprising the human antibody heavy chain gene or gene locus derived from human chromosome 14 and the human antibody light chain κ gene or gene locus derived from human chromosome 2 and a non-human animal pluripotent stem cell that comprises a MAC comprising the human antibody heavy chain gene or gene locus derived from human chromosome 14 and the human antibody light chain λ gene or gene locus derived from human chromosome 22.

Each of the non-human animal pluripotent stem cell that comprises a MAC comprising the human antibody heavy chain gene or gene locus derived from human chromosome 14 and the human antibody light chain κ gene or gene locus derived from human chromosome 2 and the non-human animal pluripotent stem cell that comprises a MAC comprising the human antibody heavy chain gene or gene locus derived from human chromosome 14 and the human antibody light chain λ gene or gene locus derived from human chromosome 22 is transferred into an early embryo of a non-human animal (e.g., 8-cell-stage embryo or blastocyst stage embryo) to thereby produce chimeric animals comprising each of the above-described MACs and then offspring animals thereof. In addition, offspring animals are subjected to crossbreeding to each other to prepare offspring animals comprising the relevant MACs.

Using the technique as described above, a non-human animal that comprises a mouse artificial chromosome vector comprising the human antibody heavy chain gene or gene locus, the human antibody light chain κ gene or gene locus, and the human antibody light chain λ gene or gene locus can be produced.

The non-human animal that comprises a MAC comprising the human antibody heavy chain gene or gene locus derived from human chromosome 14 and the human antibody light chain κ gene or gene locus derived from human chromosome 2 or the non-human animal that comprises a MAC comprising the human antibody heavy chain gene or gene locus derived from human chromosome 14 and the human antibody light chain λ gene or gene locus derived from human chromosome 22 is subjected to crossbreeding with a non-human animal of the same species in which endogenous antibody genes or gene loci corresponding to the human antibody heavy chain gene or gene locus and the human antibody light chain κ and λ genes or gene loci have been knocked out to thereby produce: a non-human animal that comprises a MAC comprising the human antibody heavy chain gene or gene locus derived from human chromosome 14 and the human antibody light chain κ gene or gene locus derived from human chromosome 2 and in which the endogenous antibody genes or gene loci corresponding to the human antibody heavy chain gene or gene locus and the human antibody light chain κ and λ genes or gene loci have been knocked out; or a non-human animal that comprises a MAC comprising the human antibody heavy chain gene or gene locus derived from human chromosome 14 and the human antibody light chain λ gene or gene locus derived from human chromosome 22 and in which the endogenous antibody genes or gene loci corresponding to the human antibody heavy chain gene or gene locus and the human antibody light chain κ and λ genes or gene loci have been knocked out.

Alternatively, the non-human animal that comprises a MAC comprising the human antibody heavy chain gene or gene locus derived from human chromosome 14 and the human antibody light chain κ gene or gene locus derived from human chromosome 2 and the non-human animal that comprises a MAC comprising the human antibody heavy chain gene or gene locus derived from human chromosome 14 and the human antibody light chain λ gene or gene locus derived from human chromosome 22 are subjected to crossbreeding with a non-human animal of the same species in which endogenous antibody genes or gene loci corresponding to the human antibody heavy chain gene or gene locus and the human antibody light chain κ and λ genes or gene loci have been knocked out to thereby produce a non-human animal that comprises a MAC comprising the human antibody heavy chain gene or gene locus derived from human chromosome 14 and the human antibody light chain κ gene or gene locus derived from human chromosome 2 and comprises a MAC comprising the human antibody heavy chain gene or gene locus derived from human chromosome 14 and the human antibody light chain λ gene or gene locus derived from human chromosome 22 and in which the endogenous antibody genes or gene loci corresponding to the human antibody heavy chain gene or gene locus and the human antibody light chain κ and λ genes or gene loci have been knocked out.

Alternatively, the non-human animal that comprises a mouse artificial chromosome vector comprising the human antibody heavy chain gene or gene locus, the human antibody light chain κ gene or gene locus, and the human antibody light chain λ gene or gene locus is subjected to crossbreeding with a non-human animal of the same species in which endogenous antibody genes or gene loci corresponding to the human antibody heavy chain gene or gene locus and the human antibody light chain κ and λ genes or gene loci have been knocked out to thereby produce a non-human animal retaining MAC and in which the endogenous antibody genes or gene loci of the animal have been knocked out.

(5) Method for Producing Useful Protein

The present invention further provides a method for producing a protein comprising: culturing cells comprising the mouse artificial chromosome vector comprising an exogenous DNA sequence in an expressible manner; and collecting a protein encoded by the DNA.

Examples of the protein include the industrially useful proteins and polypeptides in the fields of medicine, diagnosis, and agriculture. DNAs encoding these proteins or polypeptides are each inserted into the mouse artificial chromosome vector so that the DNA can be expressed in the presence of a promoter (and an enhancer if needed). Appropriate cells are then transformed or transfected with the DNA. The resulting cells are cultured, the DNAs are expressed to produce the proteins or polypeptides, and the proteins or polypeptides are then collected from the cells or medium.

Examples of the cells that can be used include eukaryotic cells, e.g., insect cells such as Sf cells, bird cells, yeast cells, and plant cells, in addition to mammalian cells.

Culture conditions including a medium are selected depending on cell types, and known culture conditions can be employed. Examples of the media for animal cells include MEM medium, DMEM, Ham's F12 medium, Eagle's MEM medium, Iscove's EME medium, RPMI 1640 medium, and a mixture thereof.

A protein or polypeptide may be collected (or isolated) by performing conventional techniques: for example, chromatography techniques, such as gel filtration chromatography, ion exchange chromatography, affinity chromatography, HPLC, and FPLC; salting-out; ammonium sulfate precipitation; organic solvent precipitation; ultrafiltration; crystallization; etc. Such techniques may be performed alone or in combination.

(6) Method for Producing Human Antibody

The present invention further provides a method for producing a human antibody comprising using the non-human animal of (4) above comprising the mouse artificial chromosome vector comprising a human antibody gene(s) to produce the human antibody and collecting the human antibody.

Examples of human antibody genes include genes encoding any class of human IgG, IgM, IgA, IgD, and IgE or any subclass of human IgG1, IgG2, IgG3, IgG4, IgA1, and IgA2. Preferable human antibody genes are the class IgG or subclasses thereof.

A human antibody consists of two heavy (H) chains having an identical sequence and two light (L) chains having an identical sequence. Both H and L chains comprise a variable region and a constant region. The variable region of the human H or L chain has three complementarity determining regions (CDR1, CDR2, and CDR3 in that order from N-terminal side to C-terminal side) and four framework regions (FR1, FR2, FR3, and FR4 in that order from N-terminal side to C-terminal side). Three individual CDR sequences of the human H or L chain determine the specificity of an antibody.

A human IgG antibody comprises a µ chain of the heavy chain and a λ or κ chain of the light chain. These antibody chain genes are present on human chromosome 14, chromosome 22, and chromosome 2, respectively. As a human antibody gene used in the present invention, a human chromosome fragment containing each antibody gene locus is used to integrate each gene locus into the same or different mouse artificial chromosome. Antibody gene sequences are available from, for example, databases of NCBI (U.S.A.). This series of procedures are an improved version of the techniques disclosed in, for example, JP 2005-230020 A.

A non-human animal that can produce an intact human antibody can be produced by crossbreeding between a non-human animal comprising a mouse artificial chromosome vector comprising a human µ-chain gene locus and the non-human animal of the same species comprising a mouse artificial chromosome vector comprising human λ- and/or κ-chain gene loci to produce a non-human chimeric animal having both H- and L-chain gene loci and offspring thereof.

The resulting non-human animal (e.g., a rodent such as a mouse or rat) that can produce an intact human antibody is immunized with a specific antigenic peptide or polypeptide. The human antibody is then isolated from the blood of the animal. Thus, the human antibody can be produced.

Alternatively, a non-human animal is immunized with a specific antigen, the spleen is extracted therefrom, and the spleen cells are allowed to fuse to myeloma cells to obtain monoclonal antibody-producing hybridomas.

(7) Method for Screening for Therapeutic Substance

The present invention further provides a method for screening for a substance effective in treating a disease comprising administering a candidate drug to a disease animal model, which is the above non-human animal, and evaluating therapeutic effects of the drug.

The non-human animal disease-model is an artificially produced animal having a disease caused by abnormalities such as abnormal biological functions due to deficiency, mutation or the like of a certain protein, abnormal drug metabolism, and abnormal chromosomes. Examples of the non-human animal model having an abnormal chromosome include, but are not limited to, animals having trisomy of human chromosome 18 or 21.

These non-human animals can be produced by the method comprising: constructing a gene or a chromosome fragment having the above abnormality; incorporating the gene or chromosome fragment into the mouse artificial chromosome vector of the present invention; introducing the vector into ES cells or iPS cells; injecting the obtained cells into the blastocyst of a fertilized egg; transplanting the cells into the uterus of a foster mother; and allowing the foster mother to give birth to offsprings.

A substance effective in treating the above disease can be screened by administering a candidate drug to the non-human animal produced above and then evaluating therapeutic effects of the drug.

Examples of the candidate drug include, but are not limited to, low-molecular-weight compounds, polymers, (glyco)proteins, peptides, (phospho or glyco)lipids, sugars, and nucleic acids.

(8) Method for Testing Pharmacological Effect, Metabolism, or Toxicity of Drug or Food In an embodiment of the present invention, the invention also provides a method for testing a pharmacological effect, metabolism, and/or toxicity of a drug or food comprising: administering a drug or food to the above non-human animal or a cell, organ, or tissue thereof, wherein the animal, cell, organ, or tissue comprises the mouse artificial chromosome vector comprising a human drug metabolism-related gene; and determining a pharmacological effect, metabolism, and/ or toxicity of the drug or food.

The present invention further provides a method for testing toxicity of a drug or food comprising: coculturing a drug and/or food and a culture cell or bacterium with a microsome or a microsome fraction S9 as obtained from the above non-human animal, wherein the animal comprises the mouse artificial chromosome vector comprising a human drug-metabolism-related gene; and determining an (adverse) influence (e.g., a mutation) on the culture cell or bacterium by the drug or food.

The human drug metabolism-related gene is as exemplified above. Also, a method for producing a non-human animal is as described above.

In the above-described method using the above non-human animal comprising the mouse artificial chromosome vector comprising a human drug metabolism-related gene, for example, the animal's conditions are observed and influences on organs or chromosomes are tested. Thus, a pharmacological effect, metabolism, or toxicity of the drug or food can be determined.

In another method of the present invention, a microsome or microsome fraction S9 (i.e., the 9000×g fraction containing a large number of enzymes that catalyze hydrolysis, reduction, oxidation, or conjugation) obtained from a non-human animal is cultured with a culture cell (in particular, animal cell, preferably mammalian cell) or bacterial cell (preferably *salmonella*) in the presence of a drug and/or food. Toxicity of the drug or food on the cells can be detected by the Ames test or a micronucleus test. According to the Ames test, the toxicity is determined based on mutations of *salmonella*. According to the micronucleus test, the toxicity is determined based on abnormalities of chromosomes in a cell nucleus. These tests have been well known and can be employed in the methods of the present invention.

EXAMPLES

Hereafter, the present invention will be described in greater detail with reference to the examples, although the scope of the invention is not limited thereto.

[Example 1] Preparation of Mouse Chromosome-Retaining DT40 Cells for Chromosome Modification Aimed at Construction of Mouse Artificial Chromosome Vector In order to construct a mouse artificial chromosome vector, a mouse chromosome is transferred into chicken DT40 cells exhibiting high homologous recombination frequency via mouse A9 cells having a high microcell formation rate.
[A] Establishment of Hybrid Cells of A9 Cells and Mouse Fibroblast (Bsd; mChr-Neo)

Figure 2:
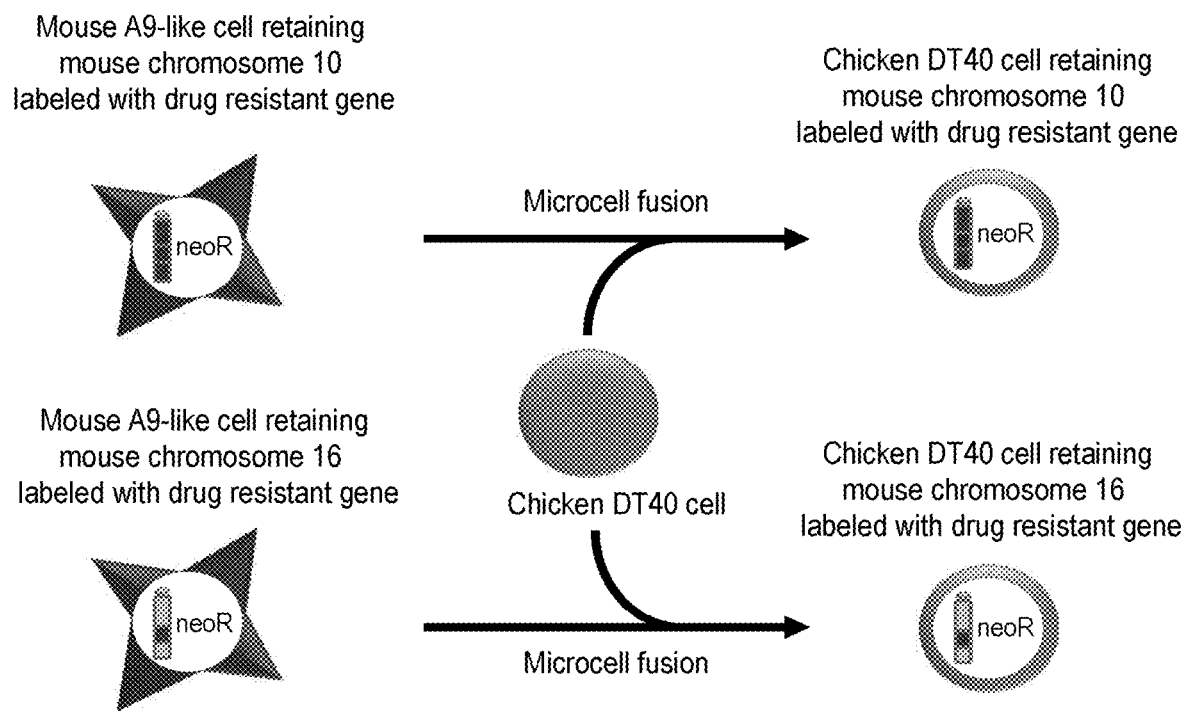
FIG. 2 shows transferring each mouse chromosome to chicken DT40 cells via microcell fusion from the A9-like cell comprising mouse chromosome 10 or 16 labeled with a drug resistant gene.

Mouse embryonic fibroblasts (mChr10-Neo and mChr16-Neo), which are mouse fibroblasts containing mouse chromosomes 10 and 16 labeled with a drug resistant gene (neo resistant gene), is fused to mouse A9 (Bsd) obtained by inserting a Bsd gene, i.e., a blasticidin S resistant gene, into known mouse A9 cells to establish mouse A9×mouse embryonic fibroblast hybrids (Bsd; mChr10-Neo and Bsd; mChr16-Neo), i.e., mouse A9 hybrid cells retaining a mouse chromosome labeled with a drug resistant gene (FIG. 1). To introduce the mouse chromosome labeled with a drug resistant gene into chicken DT40 cells having high homologous recombination frequency by microcell fusion, a mouse chromosome labeled with a drug resistant gene is introduced into the mouse A9 cell known to have a high microcell formation rate by cell fusion.
[A.1] Cell Fusion and Isolation of Dual Drug Resistant Clone Cell surfaces of mouse embryonic fibroblasts (mChr10-Neo and mChr16-Neo) comprising the G418 resistant neo gene inserted into the mouse chromosome and a mouse A9 (bsd) cell comprising the blasticidin S resistant (Bsd) gene inserted thereinto were washed with PBS (−). The cells were then dispersed with the addition of trypsin, suspended in culture medium (10% FBS, DMEM), and simultaneously inoculated at $1\times10^6$ cells into a culture flask (25 cm$^2$), followed by culture for 1 day. Cell surfaces were washed twice with PBS(−), treated with 3 ml of a PEG (1:1.4) solution (the preparation of the solution is: 5 g PEG1000 (Cat: 165-09085, Wako) was dissolved in 6 ml serum-free DMEM, followed by addition of 1 ml dimethyl sulfoxide, and the mixture was sterilized by filtration) for 1 minute, and further treated with 3 ml of a PEG (1:3) solution (the preparation of the solution is: 5 g PEG1000 (Cat: 165-09085, Wako) was dissolved in 15 ml serum-free DMEM, followed by being sterilized by filtration) for 1 minute. After the PEG solution was aspirated off, the cells were washed 3 times with serum-free DMEM, and culture was conducted for 1 day using common culture medium (10% FBS, DMEM). Cell surfaces were washed with PBS (−), dispersed with the addition of trypsin, followed by being suspended in a dual selection culture medium (10% FBS, DMEM) containing G418 and blasticidin S, which cells were then inoculated into plastic culture dishes, followed by selection culture for 2 to 3 weeks. A total of 9 resistant colonies of mChr10-Neo obtained as a result of cell fusion conducted 4 times were isolated and grown, and a total of 10 resistant colonies of mChr16-Neo obtained as a result of cell fusion conducted 4 times were isolated and grown, and randomly selected clones were employed in subsequent procedures (clone names: mouse A9× mouse embryonic fibroblast hybrids (bsd; mChr10-neo and bsd; mChr16-neo)).
[B] Introduction of Mouse Chromosome Labeled with Drug Resistant Gene into DT40 Cell A mouse chromosome labeled with a drug resistant gene was transferred to chicken DT40 cells from a mouse A9× mouse embryonic fibroblast hybrid (bsd; mChr10-neo and bsd; mChr16-neo) comprising a mouse chromosome labeled with a drug resistant gene (FIG. 2). In order to efficiently perform telomere truncation (i.e., site specific cleavage of a chromosome via insertion of an artificial telomere, which is a (TTAGGG)n sequence with a size of approximately 1 kb) and insertion of a loxP sequence as a DNA sequence insertion site into a mouse chromosome via homologous recombination, a mouse chromosome labeled with a drug resistant gene was introduced into DT40 cells having high homologous recombination frequency via microcell fusion.
[B.1] Microcell Fusion and Isolation of Drug Resistant Clone For efficient chromosome modification, the mouse chromosome was transferred from an A9× mouse embryonic fibroblast hybrid (bsd; mChr10-neo and bsd; mChr16-neo), which is an A9 hybrid cell clone, to a chicken-derived DT40 cell having high homologous recombination frequency. When the A9× mouse embryonic fibroblast hybrid (bsd; mChr10-neo and bsd; mChr16-neo) donor cells cultured in 24 flasks reached 70% confluency in each flask, colcemid treatment (colcemid 0.05 µg/ml, 20% FCS, DMEM) was performed for 48 hours at 37° C. in the presence of 5% $CO_2$ conditions. After the completion of the colcemid treatment, the medium inside the flask was aspirated off, and the flask was filled up to 90% with cytochalasin B. The flask was placed in a container dedicated to a large-size high-speed centrifuge (BECKMAN), warm water (34° C.) was added to the level at which the flask was not covered, and centrifugation was performed (Rortor ID10.500, 8,000 rpm, 1 h, 34° C.). After the completion of centrifugation, cytochalasin B was recovered, and pellets in each flask were collected in 15-ml tubes each containing 2 ml of serum-free culture medium DMEM. After slow filtration using 8 µm, 5 µm, and 3 µm filters in the successive order, each tube was centrifuged (2,000 rpm, 5 minutes, at R.T). The supernatant was aspirated off, and pellets from each tube were combined, recovered and suspended in 5 ml of serum-free culture medium DMEM, and then centrifuged (2,000 rpm, 5 minutes).

Because DT40 cells as recipient cells are floating cells, the cells need to be in the adherent state once. In order to allow DT40 to adhere to wells of a 6-well plate (Nunc), incubation was conducted in each well overnight at 37° C. with 1.5 ml of poly-L-lysine (SIGMA) adjusted to 50 g/ml to coat the wells. After the poly-L-lysine was removed, the plate was washed with PBS (−), and DT40 cells were gently inoculated at approximately 1×10⁷ cells into 2 ml of serum-free culture medium (DMEM) on a plate. The plate was mounted on a centrifuge (Beckman) and centrifuged at 37° C. and 1200 rpm for 3 minutes, whereby the DT40 cells were adhered to the plate.

Purified microcells were re-suspended in 2 ml serum-free culture medium containing PHA-P (SIGMA) and gently inoculated onto the adhered DT40 from which the serum-free culture medium (DMEM) had been removed. The plate was centrifuged at 37° C. and 1,200 rpm for 3 minutes. The supernatant was removed, and cell fusion was performed for exactly 1 minute with 1 ml of a PEG1000 (Wako) solution (prepared by completely dissolving 5 g PEG1000 in serum-free DMEM and adding 1 ml dimethyl sulfoxide thereto, followed by sterilization via filtration). Washing was performed 4 times with 4 ml serum-free culture medium (DMEM), and the adhered DT40 cells were brought back to a floating state via pipetting using 3 ml common DT40 culture solution. Thereafter, the cells were seeded on two 24-well plates at 37° C. and incubated overnight. G418 was added at a concentration of 1,500 µg/ml, and the cells were then subjected to selection culture for 3 to 4 weeks. A total of 10 resistant colonies of the A9× mouse embryonic fibroblast hybrid (bsd; mChr10-neo)#4 and 2 resistant colonies of the A9× mouse embryonic fibroblast hybrid (bsd; mChr16-neo)#2 obtained by microcell fusion were isolated, amplified, and subjected to the following analysis (clone names: DT40 (mChr10-neo) and DT40 (mChr16-neo)).

[B.2] Selection of Drug Resistant Clone
[B.2.1] FISH Analysis

DT40 (mChr10-neo) and DT40 (mChr16-neo) clones obtained above were subjected to FISH analysis using mouse Cot-1 DNA as a probe in accordance with the report of Shinohara et al. (Human Molecular Genetics, 10: 1163-1175, 2001). As a result, the number of mouse chromosomes per normal karyotype (2n) was one (1) copy in 90% of DT40 (mChr10-neo)1 and 93% of DT40 (mChr16-neo)3, respectively. Thus, these clones were employed in the subsequent steps.

[Example 2] Construction of Mouse Artificial Chromosome Via Modification of Mouse Chromosome 10 (10MAC)

Upon construction of a mouse artificial chromosome vector, it is necessary to delete as many endogenous genes as possible. A majority of the long arm of mouse chromosome 10 including endogenous genes is deleted via telomere truncation in chicken DT40 cells exhibiting high homologous recombination efficiency.

Figure 3:
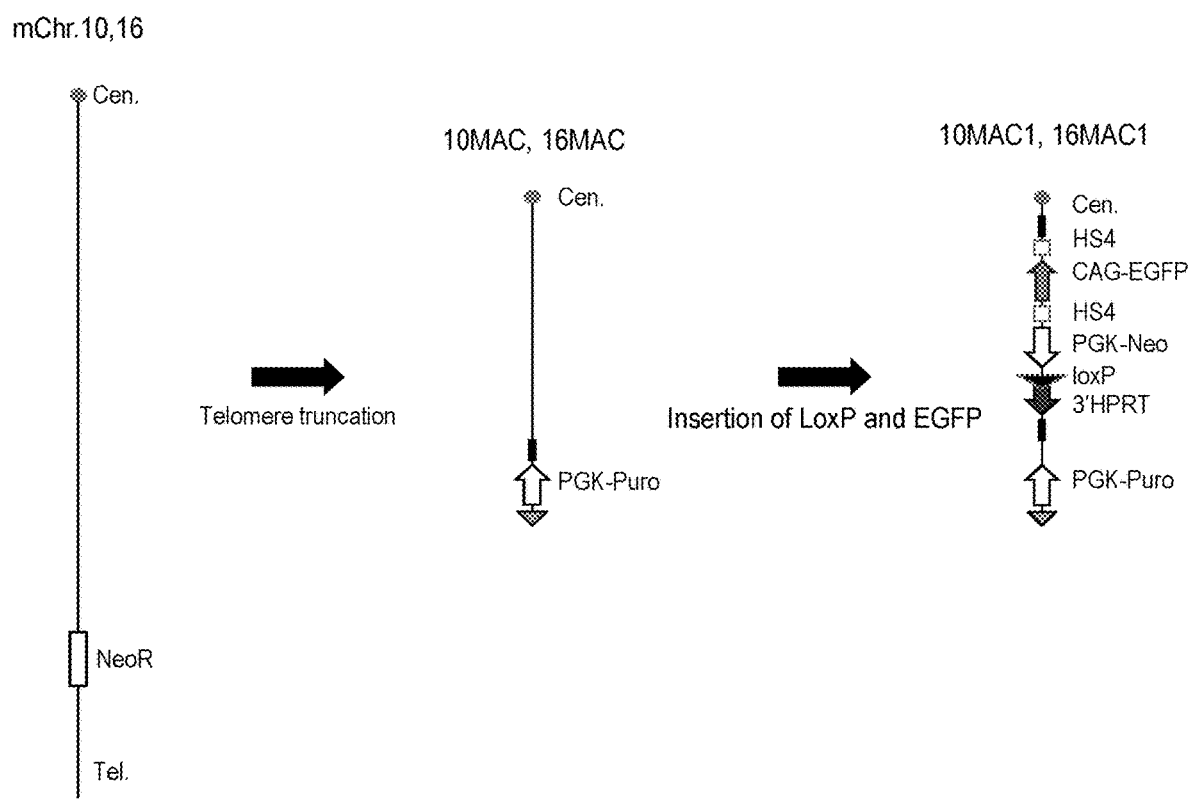
FIG. 3 schematically shows a step of constructing a mouse artificial chromosome (MAC) from each of naturally-occurring mouse chromosomes 10 and 16 via telomere truncation and a step of inserting a cassette comprising loxP, the EGFP gene, and the like into the MAC. In the figure, Cen. represents a centromere, Tel. represents a telomere, HS4 represents an insulator, CAG and PGK each represent a promoter, EGFP represents a gene encoding a fluorescent protein, NeoR, Puro, and Neo each represents a drug resistant gene, and HPRT represents a hypoxanthine-guanine phosphoribosyltransferase gene.

[A] Site-Directed Cleavage of a Region Distant from the Centromere from a Region Proximal to the Centromere of Mouse Chromosome 10 in Chicken DT40 Cells by Telomere Truncation An influence imposed on an experiment system is reduced as the number of endogenous genes other than target genes to be introduced into the mouse artificial chromosome vector becomes smaller. Among endogenous genes, in addition, it is necessary to refrain from retaining genes that would influence the development of mouse individuals due to change in gene expression levels (e.g., imprinting genes). Thus, a majority of the mouse long arm is deleted (FIG. 3).

[A.1] Preparation of Telomere Truncation Vector

As a basic vector for short arm proximal region-specific cleavage, a pBS-TEL/puro construct (Kuroiwa et al., Nature Biotech., 2002) was used.

Self-annealed synthetic oligo (Sigma) was inserted into the EcoRI site of pBS-TEL/puro. The sequence of the synthetic oligo is shown below.

```
EcoRI-AscI-EcoRI:
                                  (SEQ ID NO: 1)
5'-AATTCGGCGCGCCG-3'
```

Based on the long-arm proximal nucleotide sequence of the mouse chromosome 10 obtained from GenBank database (NC_000076.6), a target sequence for homologous recombination was designed. PCR was performed to amplify the target sequence for homologous recombination using genomic DNA extracted from DT40 (mChr10-neo) 1 as a template. The sequences of the primers used for PCR are shown below.

```
AscI_m10T F2:
                                  (SEQ ID NO: 2)
5'-TCGAGGCGCGCCAGCCTTCTAGGGAACAGGAGATGTTCAA-3'

BamHI_m10T R3:
                                  (SEQ ID NO: 3)
5'-TCGAGGATCCGCCTTGAGTGGGGTTCTAGTCATCTTTC-3'
```

Figure 4:
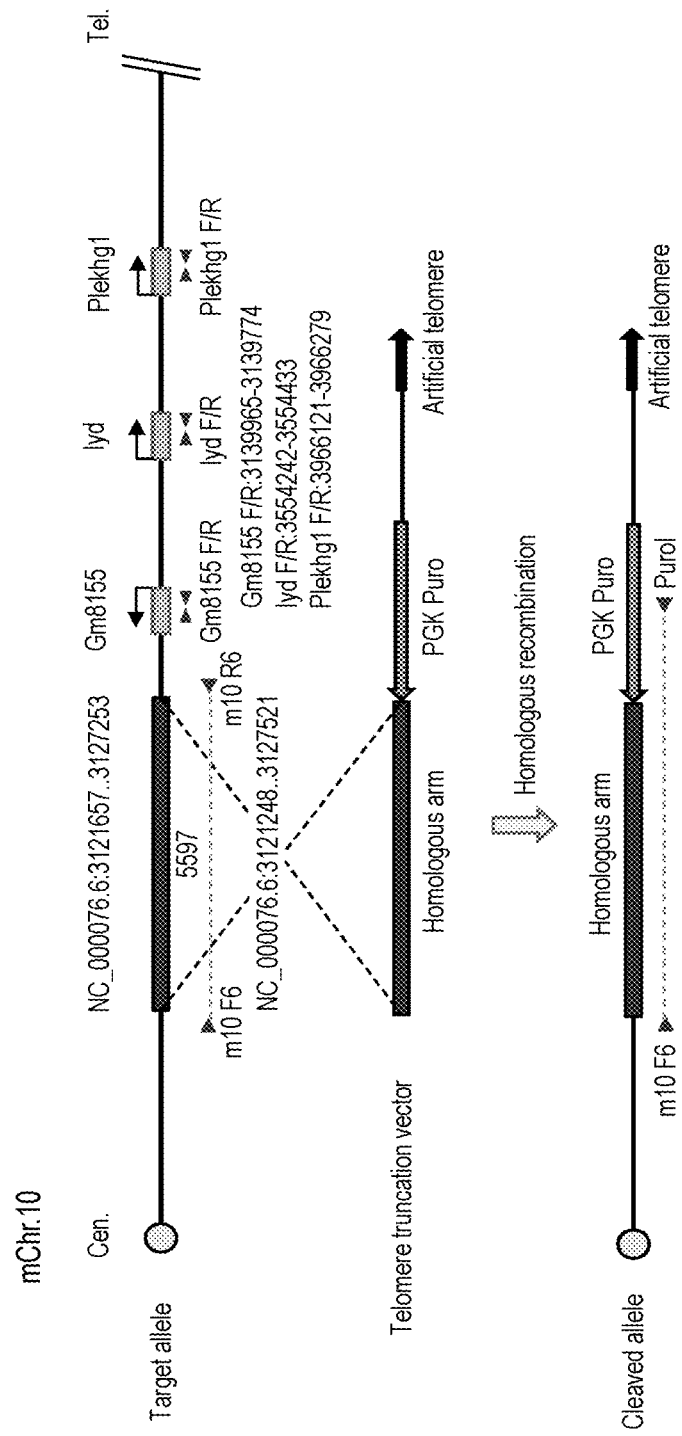
FIG. 4 schematically shows telomere truncation of mouse chromosome 10.

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 6 minutes. The PCR product was digested with AscI and BamHI (NEB), separated by agarose gel, purified, and cloned into pBS-TEL/puro digested with AscI and BamHI (vector name: pBS-TEL/puro_10MAC). The targeting vector, the target sequence, and the chromosome allele obtained by homologous recombination are shown in FIG. 4.

[A.2] Selection of Homologous Recombinant

A vector that performs site-directed cleavage of a region distant from the centromere from a region proximal to the centromere of mouse chromosome 10 was transfected using pBS-TEL/puro_10MAC described above, followed by isolation of puromycin resistant clones, and homologous recombinants were selected.

PCR was performed using DNAs extracted from the obtained clones as template to confirm that site-directed cleavage had occurred. The primer sequences are shown below.

```
m10 F6:
                                  (SEQ ID NO: 4)
5'-AACTACCCAGTTCTGCATTTGGTGTGAG-3' m10 R6:
                                  (SEQ ID NO: 5)
5'ATCAGTCATCAGTACCCCCAACCTCTCT-3' m10 F6 (described above)

PuroI:
                                  (SEQ ID NO: 6)
5'-GAGCTGCAAGAACTCTTCCTCACG-3'
```

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 8 minutes.

```
Plekhg1 F:
                                    (SEQ ID NO: 7)
5'-TGGATGGGTTTCAATGCCACT-3'

Plekhg1 R:
                                    (SEQ ID NO: 8)
5'-GGCATTCTCCCCTGTTGTGG-3'

Gm8155 F:
                                    (SEQ ID NO: 9)
5'-ACCCCTCGAACCCCTATTGC-3'

Gm8155 R:
                                   (SEQ ID NO: 10)
5'-CACGCCATCGGTGATGGATA-3'

Iyd F:
                                   (SEQ ID NO: 11)
5'-TGGGATGACCCCCACTTCTTT-3'

Iyd R:
                                   (SEQ ID NO: 12)
5'-TTTTGGCCTCTTGCCCCATA-3'
```

PCR was performed using GeneAmp 9600 (PerkinElmer, Inc.) as a thermal cycler, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: thermal denaturation at 95° C. for 10 minutes was followed by 35 cycles of 94° C. for 30 seconds, 60° C. for 30 seconds, and 72° C. for 30 seconds.

As a result, 3 clones in which the mouse chromosome 10 region had been cleaved were confirmed (clone name: DT40 (10MAC)). The targeting vector, the target sequence, and the chromosome allele generated by homologous recombination are shown in FIG. 4.

[A.3] Selection of Drug Resistant Clone by Two-Color FISH Analysis

Figure 5:
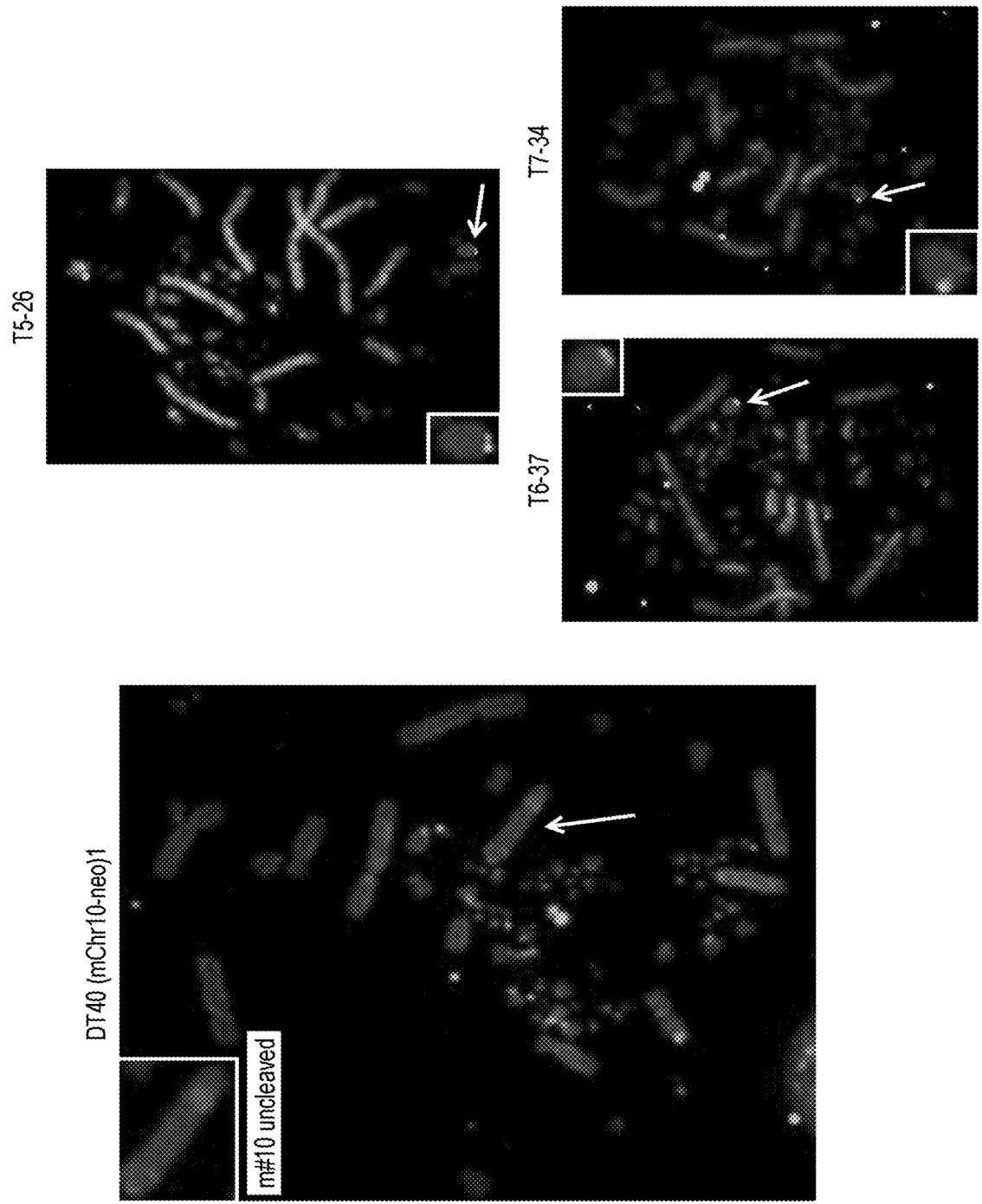
FIG. 5 shows images obtained by FISH analysis indicating mouse chromosome 10 before the long arm portion is deleted therefrom and mouse chromosome 10 after the long arm portion is deleted therefrom (10MAC; T5-26, T6-37, and T7-34).

The 3 clones of DT40 (10MAC) obtained above were subjected to FISH analysis using mouse cot-1 DNA and the PGKPuro plasmid as probes in accordance with the report of Shinohara et al. (Human Molecular Genetics, 10: 1163-1175, 2001). As a result, it was confirmed that the long arm of mouse chromosome 10 had been cleaved near the centromere in all the 3 clones (FIG. 5). In the subsequent steps, clones T5-26 and T6-37 were used.

[Example 3] Construction of Mouse Artificial Chromosome Vector 10MAC1

As a DNA insertion sequence, a GFP-PGKneo-loxP-3' HPRT type of loxP sequence was inserted into the mouse artificial chromosome 10MAC to construct the mouse artificial chromosome vector 10MAC1. The resulting 10MAC1 was introduced into hprt-deficient CHO cells.

[A] Construction of Mouse Artificial Chromosome Vector 10MAC1 Via Insertion of GFP-PGKneo-loxP-3' HPRT Type of loxP Sequence into Mouse Artificial Chromosome 10MAC A gene introduction loxP site and a GFP expression unit capable of observing the presence thereof were introduced into the mouse artificial chromosome 10MAC.

[A.1] Preparation of GFP-PGKneo-loxP-3' HPRT Type-loxP Targeting Vector

As a basic plasmid used for inserting the loxP sequence into DT40 (10MAC), V913 (Lexicon genetics) was used. The DNA sequence of mouse chromosome 10 as a loxP insertion site was obtained from the GenBank database (NC_000076.6). DNA extracted from a drug resistant clone was used as a template, and the sequences of primers to amplify the 2 target sequences for homologous recombination are shown below.

```
KpnI_m10 LA F:
                                   (SEQ ID NO: 13)
5'-TCGAGGTACCTCTAAGTCAGGGAAAGATCCCCTTCTTG-3'

XhoI_m10 LA R:
                                   (SEQ ID NO: 14)
5'-TCGACTCGAGGACCATGAAGATGGTCCAACTAAAGCAA-3'

SalI_m10 RA F:
                                   (SEQ ID NO: 15)
5'-TCGAGTCGACCACTGCTCTTTCTTTAGTTACATGCAGCCC-3'

NotI_m10 RA R:
                                   (SEQ ID NO: 16)
5'-TCGAGCGGCCGCATTCTTGCCAAGCTACTCTTCCGAGCTA-3'
```

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds, 68° C. for 3 minutes, and 68° C. for 5 minutes.

Figure 6:
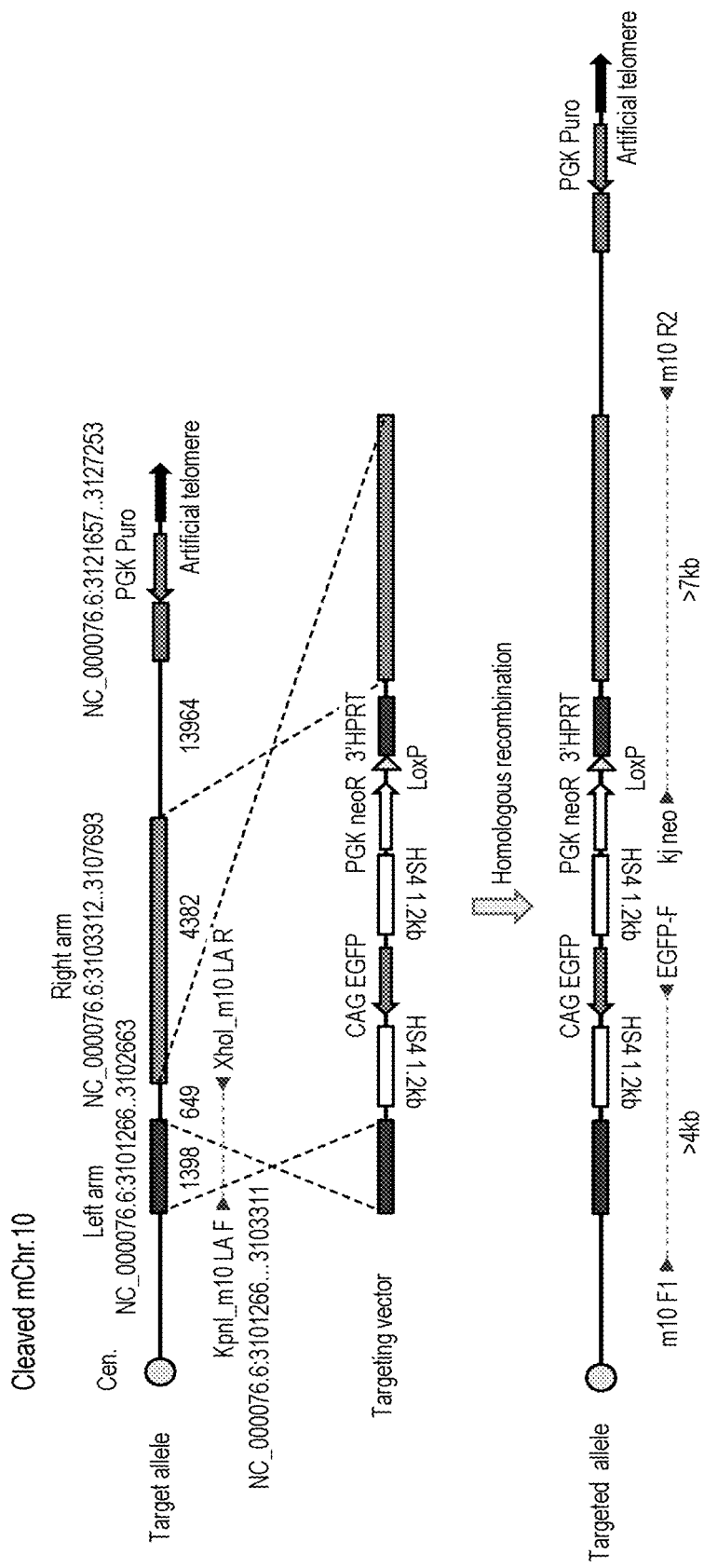
FIG. 6 schematically shows introduction of loxP and the EGFP expression unit into mouse chromosome 10 (10MAC).

The PCR products were each digested with KpnI (NEB) and XhoI (NEB) and SalI (NEB) and NotI (NEB), respectively, separated by agarose gel, purified, and cloned into the KpnI/XhoI or SalI/NotI site of V913 (vector name: V913-m10LARA). Concerning 3' HPRT-loxP, the oligo-synthesized loxP sequence was cloned into the XbaI site of V820 (Lexicon genetics). 3' HPRT-loxP comprising exons 3 to 9 of the HPRT gene was cloned into EcoRI and AscI of V907 (Lexicon genetics) (vector name: X3.1). Further, the PGK-neo sequence cleaved with KpnI and NotI was cloned into the KpnI site and the EcoRI site of X3.1 (vector name: X4.1). PGKneo-loxP-3' HPRT cleaved from X4.1 with KpnI and AscI was cloned into the KpnI site and the AscI site of V913 (vector name: pVNLH). HS4-CAG-EGFP-HS digested with NotI and SalI and then blunt-ended (provided by Dr. Okabe, Osaka University and Dr. Felsenfeld, NIH) was cloned into the EcoRV site of pVNLH (vector name: pVGNLH). The GFP-PGKneo-loxP-3' HPRT cassette cleaved from pVGNLH with SalI and AscI was cloned into the XhoI site and the AscI site of V913-m10LARA (vector name: p10MAC1). The targeting vector, the target sequence, and the chromosome allele resulting from homologous recombination are shown in FIG. 6.

[A.2] Transfection and Isolation of G418 Resistant Clone

Chicken DT40 cells were cultured in RPMI 1640 medium (Gibco) supplemented with 10% fetal bovine serum (referred to as "FBS" hereinbelow, Gibco), 1% chicken serum (Gibco), and 10-4 M 2-mercaptoethanol (Sigma). Approximately $10^7$ DT40 (10MAC) T5-26 and T6-37 cells were washed once with supplement-free RPMI 1640 medium, suspended in 0.5 ml of supplement-free RPMI 1640 medium, supplemented with 25 µg of the targeting vector p10MAC1 linearized with the restriction enzyme NotI (TAKARA), transferred to a cuvette (Bio-Rad Laboratories, Inc.) for electroporation, and allowed to stand at room temperature for 10 minutes. The cuvette was mounted on Gene Pulser (Bio-Rad Laboratories, Inc.) and voltage was applied under the conditions of 550 V and 25 µF. The resultant was allowed to stand at room temperature for 10 minutes and then cultured for 24 hours. The medium was exchanged with a medium containing G418 (1.5 mg/ml), dispensed into two 96-well culture plates, and then subjected to selection culture for about 2 weeks. A total of 24 resistant colonies of T5-26 and 20 resistant colonies of T6-37 obtained as a result of transfection conducted 2 times were isolated, amplified, and subjected to the subsequent analysis (clone name: DT40 (10MAC1)).

[A.3] Selection of Homologous Recombinant

[A.3.1] PCR Analysis

PCR was performed using the following primers in order to select a recombinant using genomic DNA extracted from the G418 resistant cell line as a template, and whether or not recombination had occurred in a site-directed manner on mouse chromosome 10 was examined. The primer sequences are shown below.

```
m10 F1:
                                        (SEQ ID NO: 17)
5'-TGAGAAATACCGAATGGCAGAGAAACAC-3'

EGFP-F(L):
                                        (SEQ ID NO: 18)
5'-CCTGAAGTTCATCTGCACCA-3' kj neo:
                                        (SEQ ID NO: 19)
5'-CATCGCCTTCTATCGCCTTCTTGACG-3' m10 R2:
                                        (SEQ ID NO: 20)
5'-GAGAGGAGGGAAGCTTGATGAGAAAATG-3'
```

KpnI m10 LA F (described above)
XhoI m10 LA R (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 5 minutes, 8 minutes, and 2.5 minutes.

The results indicate that target recombination had occurred in 8 and 3 clones of DT40 (10MAC) T5-26 and T6-37, respectively.

[A.3.2] Two-Color FISH Analysis

Figure 7:
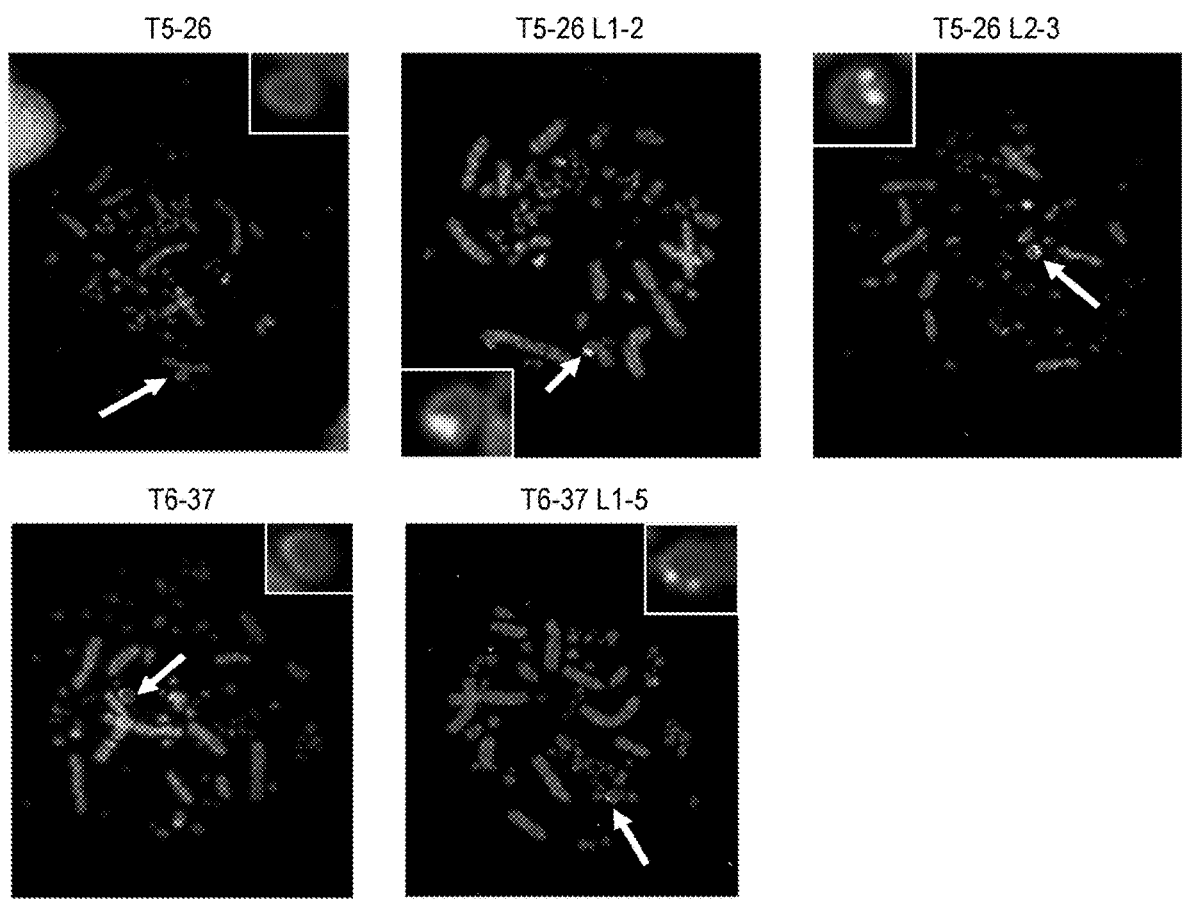
FIG. 7 shows images obtained by FISH analysis conducted before loxP and the EGFP expression unit were introduced into mouse chromosome 10 (10MAC) and after loxP and the EGFP expression unit were introduced into mouse chromosome 10 (10MAC1). In the figure, T5-26 and T6-37 are images obtained before loxP and the EGFP expression unit were introduced and T5-26L1-2, T5-26L2-3, and T6-37L1-5 are images obtained after loxP and the EGFP expression unit were introduced. Arrows indicate 10MAC and 10MAC1, respectively.

DT40 (10MAC1) obtained above was subjected to two-color FISH analysis in accordance with the method of Matsubara et al. (FISH test protocol, Shujunsha Co., Ltd., 1994). FISH analysis was performed using mouse cot-1 DNA and the GFP-PGKneo-loxP-3' HPRT (pVGNLH) cassette as probes. As a result, a FITC signal derived from the probe was detected near the centromere of the mouse chromosome 10 fragment targeted with the loxP sequence, and a signal that was not observed for the mouse chromosome 10 fragment (e.g., DT40 (10MAC)) before targeted with a negative control was detected. It was thus visually confirmed that site-directed recombination had occurred (FIG. 7). On the basis of the results above, it was concluded that DT40 cell clones comprising the mouse artificial chromosome vector 10MAC1 were obtained. In the subsequent step, 3 clones: i.e., DT40 (10MAC1) T5-26 L1-2, T5-26 L2-3, and T6-37 L1-5, were used.

[B] Introduction of 10MAC1 from DT40 Cell Containing the Mouse Artificial Chromosome Vector 10MAC1 into CHO Cell In order to introduce the mouse artificial chromosome vector 10MAC1 into mouse ES cells via CHO cells or to stably insert a target gene (or target genes), such as the CYP3A cluster or human antibody gene, via loxP as a DNA sequence insertion site of the mouse artificial chromosome vector 10MAC1 within CHO cells, 10MAC1 was introduced into CHO cells.

[B.1] Microcell Fusion and Isolation of Drug Resistant Clone

Microcell fusion was performed using DT40 (10MAC1) as donor cells and CHO (HPRT), i.e., the CHO hprt-deficient cell (Accession Number: JCRB0218; the Health Science Research Resources Bank), in the same manner as described above. The G418 resistant colonies obtained by microcell fusion were isolated, amplified, and subjected to the subsequent analysis (clone name: CHO (HPRT$^-$; 10MAC1)).

[B.2] Selection of Drug Resistant Clone

[B.2.1] PCR Analysis

PCR was performed using the following primers in order to select a recombinant using genomic DNA extracted from the G418 resistant cell line as a template, and whether or not the mouse artificial chromosome vector 10MAC1 had been introduced into CHO cells was examined. The primer sequences are shown below.

m10 F6 (described above)
PuroI (described above)
m10F1 (described above)
EGFP-F(L) (described above)
kj neo (described above)
m10 R2 (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 8 minutes and 2.5 minutes. PCR-positive clones were subjected to the subsequent analysis.

[B.2.2] Mono-Color FISH Analysis

Figure 8:
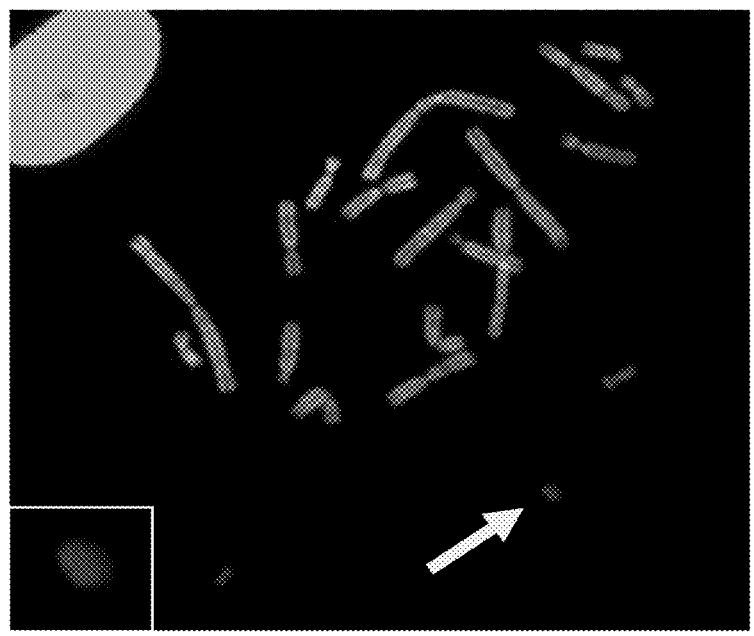
FIG. 8 shows an image obtained by FISH analysis of a CHO cell retaining 10MAC1. In the figure, an arrow indicates 10MAC1.

The CHO (HPRT$^-$; 10MAC1) clones obtained above were subjected to FISH analysis using mouse cot-1 DNA as a probe in accordance with the report of Shinohara et al. (Human Molecular Genetics, 10: 1163-1175, 2001). As a result, it was confirmed that the mouse artificial chromosome vector 10MAC1 had been introduced into CHO cells. A clone was found to retain 10MAC1 independently and stably in CHO (FIG. 8).

[C] Confirmation of Insertion of Recombination into 10MAC1

Whether or not LoxP-3' HPRT, which is a recombinant sequence of 10MAC1, would function was examined.

[C.1] Insertion of Cyclic DNA into MAC1 Using Cre/loxP System

CHO (HPRT–; 10MAC1) cells were cultured to reach confluency in a 6-cm dish. A Cre expression plasmid (vector name: pBS185) and a 5' HPRT-LoxP plasmid were introduced together using Lipofectamine 2000 in accordance with the manufacturer's instructions. Thereafter, the cells were subjected to subculture in ten 10-cm cell culture dishes, and drug selection with HAT was performed after further 24 hours. The 24 drug resistant clones obtained were subjected to the subsequent analysis.

[C.2] Analysis of Drug Resistant Clone

Upon site-directed recombination as expected and insertion of cyclic DNA retaining 5' HPRT-LoxP, the HPRT gene was reconstructed in 10MAC1, and HAT resistance was acquired. DNA was extracted from the drug resistant clone and PCR was performed to detect a joint of such recombination. The primers used are shown below.

```
TRANS L1:
                                          (SEQ ID NO: 21)
5'-TGGAGGCCATAAACAAGAAGAC-3'

TRANS R1:
                                          (SEQ ID NO: 22)
5'-CCCCTTGACCCAGAAATTCCA-3'
```

PCR was performed using these primers, LA taq (Takara), and buffers and dNTPs (dATP, dCTP, dGTP, and dTTP) included in the kit under the recommended conditions. Temperature and cycle conditions were as follows: thermal denaturation at 98° C. for 1 minute was followed by 30 cycles of 94° C. for 10 seconds, 60° C. for 30 seconds, and 72° C. for 3 minutes. As a result, all the 24 drug resistant clones were found to be PCR-positive. The results demonstrate that cyclic DNA had been inserted into such drug resistant clones via site-directed recombination with high efficiency.

[Example 4] Construction of Mouse Artificial Chromosome Via Modification of Mouse Chromosome 16 (16MAC)

Upon construction of a mouse artificial chromosome vector, it is necessary to delete as many endogenous genes as possible. Via telomere truncation, a long arm of mouse chromosome 16 including endogenous genes is deleted from a chicken DT40 cell exhibiting high homologous recombination efficiency.

[A] Site-Directed Cleavage of a Region Distant from the Cemtromere from a Region Proximal to the Centromere of Mouse Chromosome 16 in Chicken DT40 Cells by Telomere Truncation An influence imposed on an experiment system is reduced as the number of endogenous genes other than the target genes to be introduced into the mouse artificial chromosome vector becomes smaller. Among endogenous genes, in addition, it is necessary to refrain from retaining genes that would influence the development of mouse individuals due to a change in gene expression levels (e.g., imprinting genes). Thus, a majority of the mouse long arm was deleted (FIG. 3).

[A.1] Preparation of Telomere Truncation Vector

As a basic vector for short arm proximal region-specific cleavage, a pBS-TEL/puro construct (Kuroiwa et al., Nature Biotech., 2002) was used.

Based on the long-arm proximal nucleotide sequence of the mouse chromosome 16 obtained from GenBank database, a target sequence for homologous recombination was designed. PCR was performed to amplify the target sequence for homologous recombination using genomic DNA extracted from DT40 (mChr16-neo) 3 as a template. The sequences of the primers used for PCR are shown below.

```
BamHI_m16T F2:
                                          (SEQ ID NO: 23)
5'-TCGAGGATCCGGGAGTAATTTTCAATCCTTGAGGCAGA-3'

BglII_m16T R2:
                                          (SEQ ID NO: 24)
5'-TCGAAGATCTCATCAGTGTACACCACAATCCCATCTGT-3'
```

Figure 9:
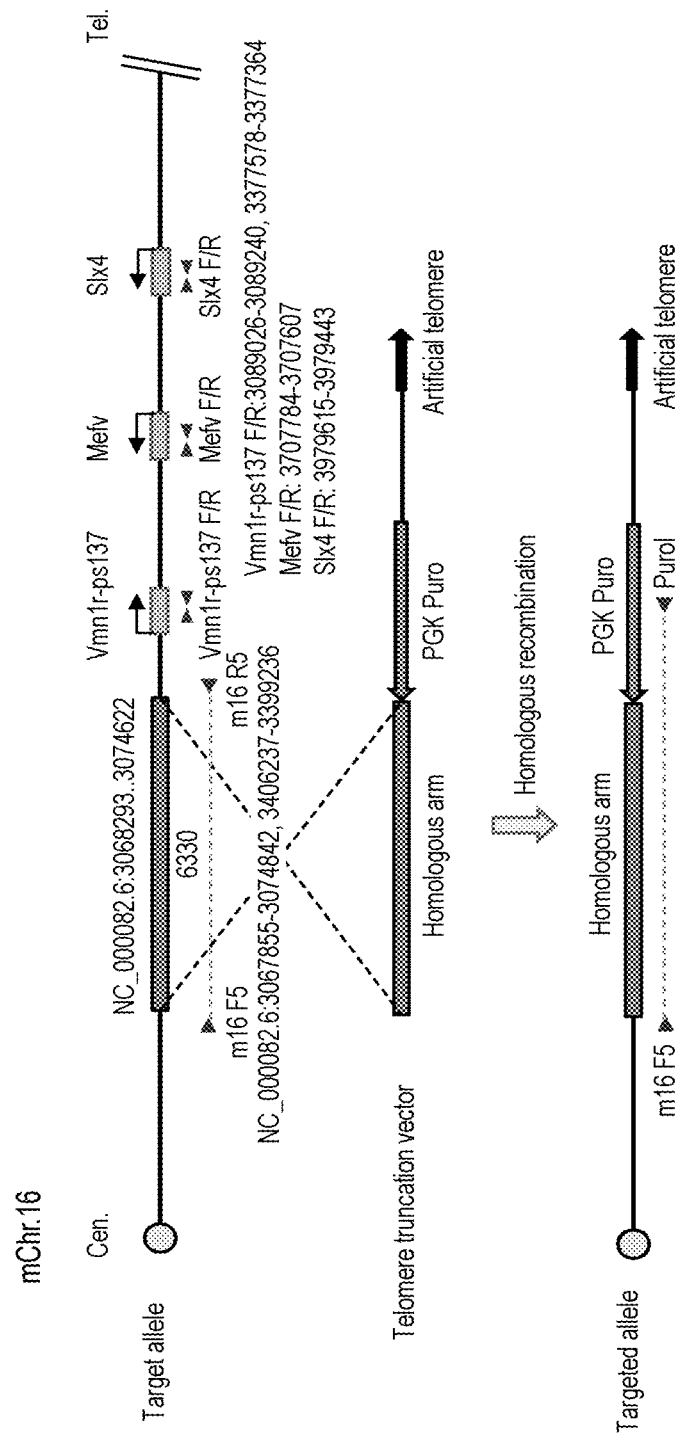
FIG. 9 schematically shows telomere truncation of mouse chromosome 16.

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 7 minutes. The PCR product was digested with BamHI and BglII (NEB), separated by agarose gel, purified, and cloned into BamHI-digested pBS-TEL/puro (vector name: pBS-TEL/puro_16MAC). The targeting vector, the target sequence, and the chromosome allele obtained by homologous recombination are shown in FIG. 9.

[A.2] Selection of Homologous Recombinant

A vector that performs site-directed cleavage of a region distant from a region proximal to mouse chromosome 16 was transfected using pBS-TEL/puro_16MAC described above, puromycin resistant clones were isolated, and homologous recombinants were selected.

PCR was performed using DNAs extracted from the clones as template to confirm whether or not site-directed cleavage had occurred. The primer sequences are shown below. m16 F5: 5'-cctcttcttgacggttaccacattttgc-3' (SEQ ID NO: 25) PuroI (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 9 minutes.

```
Vmn1r-ps137 F:
                                          (SEQ ID NO: 26)
5'-TGAATTGGTCCCTCCTGCTCA-3'

Vmn1r-ps137 R:
                                          (SEQ ID NO: 27)
5'-CAGGCCATGAGACCCAGACA-3'

Mefv F:
                                          (SEQ ID NO: 28)
5'-TCCTCGGAGAATGGCTCCTG-3'

Mefv R:
                                          (SEQ ID NO: 29)
5'-GGCAGGTTGATGGGAACTGG-3'

Slx4 F:
                                          (SEQ ID NO: 30)
5'-AACCAGGGTCCCCATCCTGT-3'

Slx4 R:
                                          (SEQ ID NO: 31)
5'-TGGGCTGGTTTCAATGCTGA-3'
```

-continued

Gm4106 F:
(SEQ ID NO: 32)
5'-GTGTGGCCATGGCTGGAGTA-3'

Gm4106 R:
(SEQ ID NO: 33)
5'-TGTTCCTCTGCTGCCACTCG-3'

Gm35974 F:
(SEQ ID NO: 34)
5'-ACCCAGCCACTCCCACCATA-3'

Gm35974 R:
(SEQ ID NO: 35)
5'-AAGGGCATGGCTATCCCACA-3'

PCR was performed using GeneAmp 9600 (PerkinElmer, Inc.) as a thermal cycler, Ampli Taq Gold (Applied Biosystems) as Taq polymerase, and buffers and dNTPs (dATP, dCTP, dGTP, and dTTP) included in the kit under the recommended conditions. Temperature and cycle conditions were as follows: thermal denaturation at 95° C. for 10 minutes was followed by 35 cycles of 94° C. for 30 seconds, 60° C. for 30 seconds, and 72° C. for 30 seconds.

Figure 10:
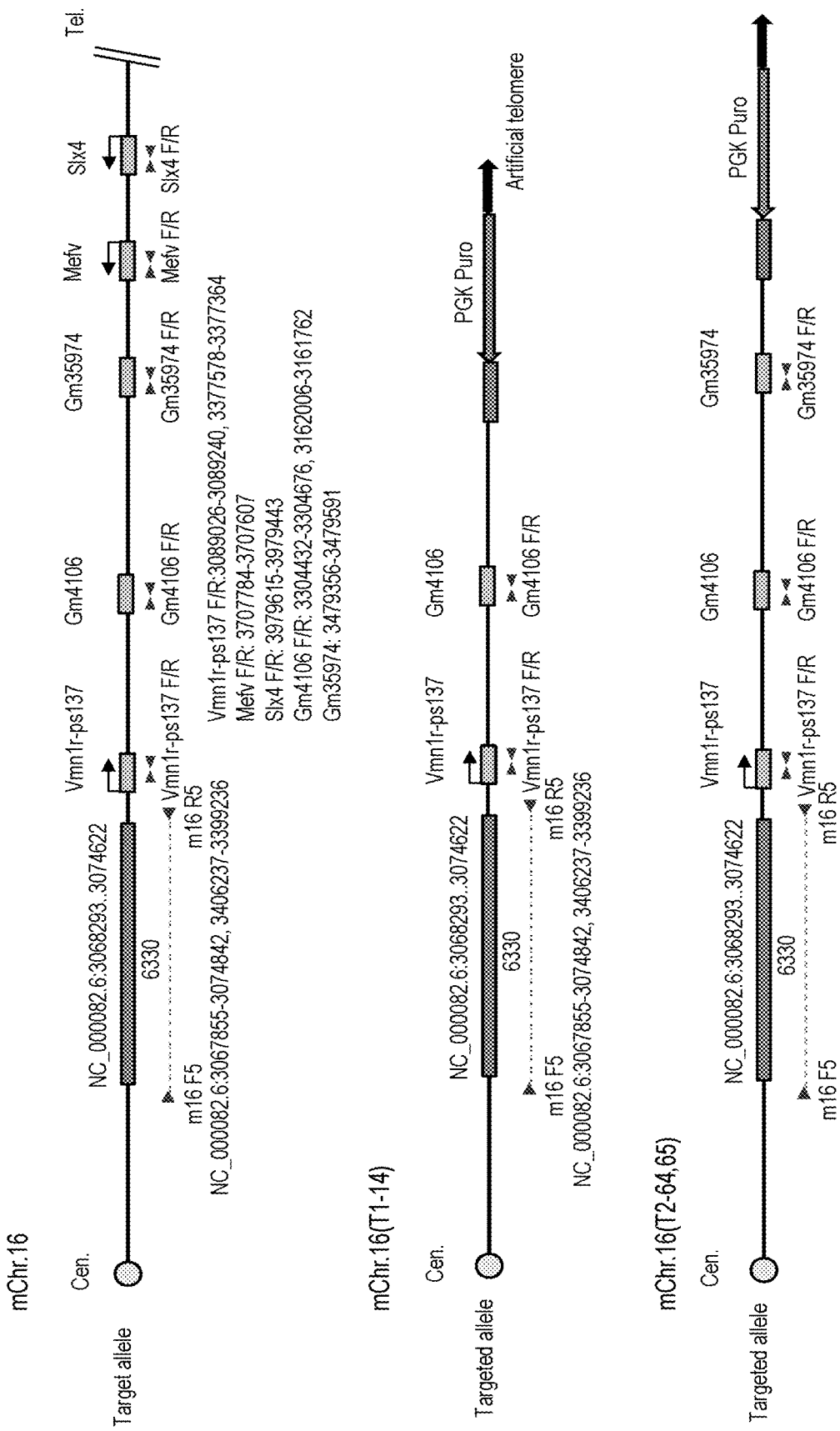
FIG. 10 shows two patterns of alleles from which a majority of the long arm obtained via telomere truncation of mouse chromosome 16 has been deleted. In the figure, one pattern is of T1-14 and the other pattern is of T2-64 and T2-65.

As a result, 3 clones indicating cleavage of the mouse chromosome 10 region were detected (clone name: DT40 (16MAC)). The cleavage sites in these clones were found to be different, suggesting the presence of 2 patterns of alleles. FIG. 10 shows 2 patterns of putative alleles after cleavage.

[A.3] Selection of Drug Resistant Clone by Mono-Color FISH Analysis

Figure 11:
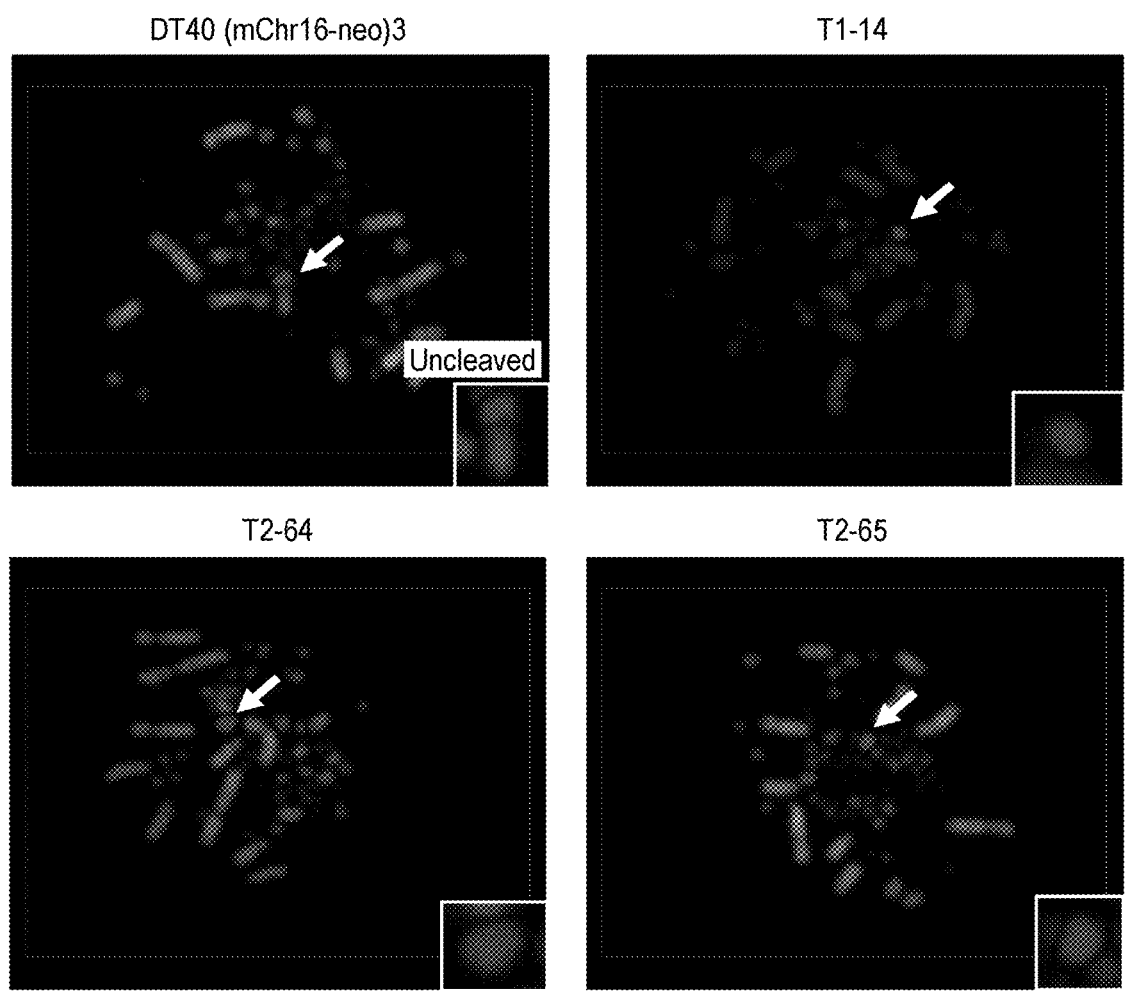
FIG. 11 shows images obtained by FISH analysis indicating mouse chromosome 16 before the long arm portion is deleted therefrom and mouse chromosome 16 after the long arm portion is deleted therefrom (16MAC; T1-14, T2-64, and T2-65). An arrow indicate mouse chromosome 16, each 16MAC.

The 3 DT40 (16MAC) clones obtained above were subjected to FISH analysis using mouse cot-1 DNA as a probe in accordance with the report of Shinohara et al. (Human Molecular Genetics, 10: 1163-1175, 2001). As a result, it was confirmed that the long arm of mouse chromosome 16 had been cleaved near the centromere in all the 3 clones (FIG. 11).

[Example 5] Construction of Mouse Artificial Chromosome Vector 16MAC1

As a DNA insertion sequence, a GFP-PGKneo-loxP-3' HPRT type loxP sequence was inserted into the mouse artificial chromosome 16MAC to construct the mouse artificial chromosome vector 16MAC1. The resulting 16MAC1 was introduced into an hprt-deficient CHO cell.

[A] Insertion of GFP-PGKneo-loxP-3' HPRT Type loxP Sequence into Mouse Artificial Chromosome Vector 16MAC

[A.1] Preparation of GFP-PGKneo-loxP-3' HPRT Type loxP Targeting Vector

Vectors targeting different sequences of 2 types of 16MACs with different sites of cleavage were constructed.

As a type 1 vector, a targeting vector targeting the homologous sequence used for telomere truncation was constructed.

As a basic plasmid used for inserting the loxP sequence into DT40 (16MAC), V913 (Lexicon genetics) was used. The DNA sequence of mouse chromosome 16 as a loxP insertion site was obtained from the GenBank database (NC_000082.6). Genomic DNA was extracted as a template from a drug resistant clone, and the sequences of primers used to amplify the 2 target sequences for homologous recombination are shown below.

KpnI_m16 HAtLA F:
(SEQ ID NO: 36)
5'-TCGAGGTACCGGGAGTAATTTTCAATCCTTGAGGCAGA-3'

XhoI_m16 HAtLA R:
(SEQ ID NO: 37)
5'-TCGACTCGAGTGGCACTGACCCCTTAATTACGTACAGA-3'

SalI_m16 HAtRA F:
(SEQ ID NO: 38)
5'-TCGAGTCGACAAAGATTTGCATCCTTGGCCATGACTC-3'

NotI_m16 HAtRA R:
(SEQ ID NO: 39)
5'-TCGAGCGGCCGCCATCAGTGTACACCACAATCCCATCTGT-3'

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 4 minutes.

Figure 12:
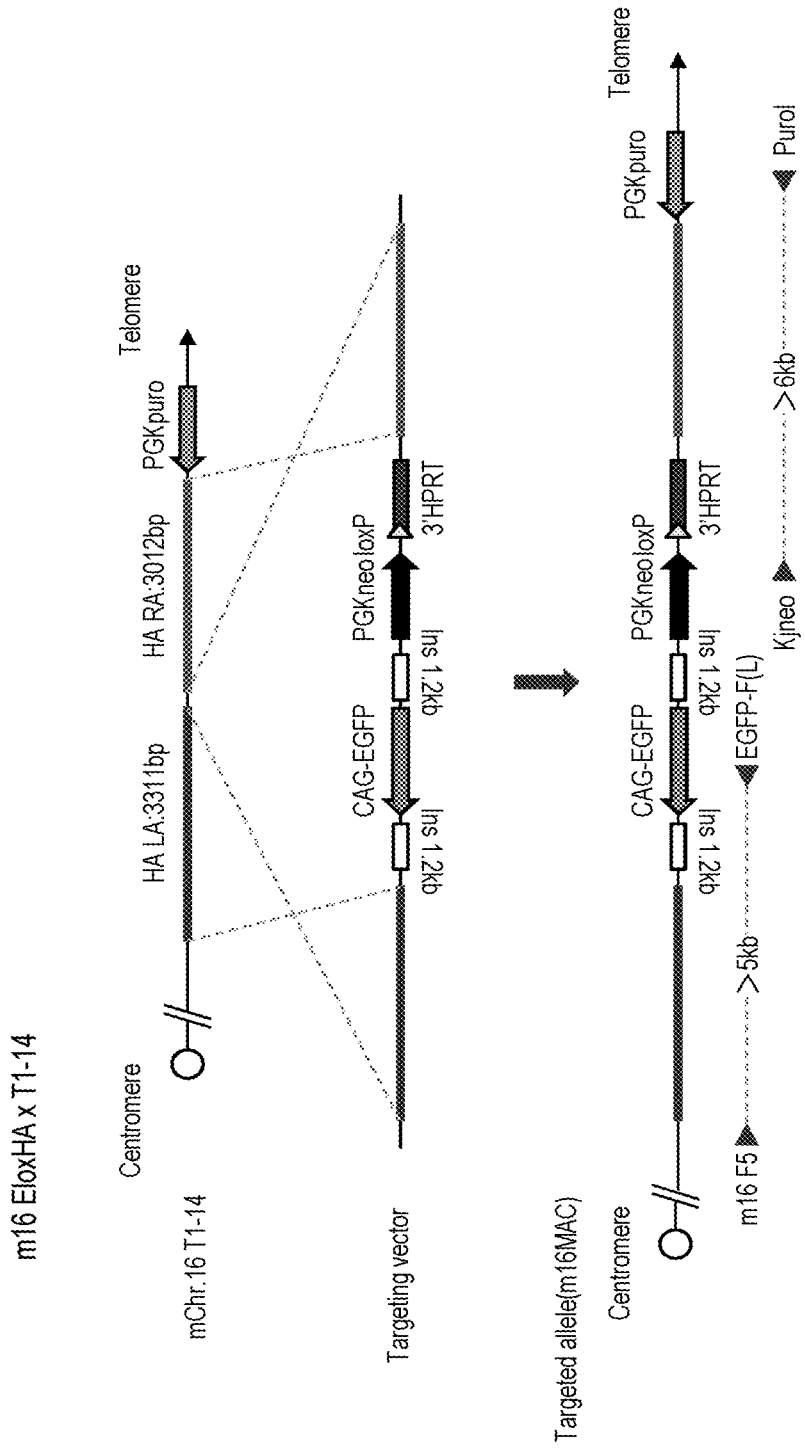
FIG. 12 schematically shows introduction of loxP and the EGFP expression unit into mouse chromosome 16 after the long arm portion was deleted therefrom (pattern 1).

The PCR products were each digested with KpnI (NEB) and XhoI (NEB) and SalI (NEB) and NotI (NEB), respectively, separated by agarose gel, purified, and cloned into the KpnI/XhoI or SalI/NotI site of V913 (vector name: V913-m16HA). Concerning 3' HPRT-loxP, the oligo-synthesized loxP sequence was cloned into the XbaI site of V820 (Lexicon genetics). 3' HPRT-loxP comprising exons 3 to 9 of the HPRT gene was cloned into EcoRI and AscI of V907 (Lexicon genetics) (vector name: X3.1). Further, the PGK-neo sequence cleaved with KpnI and NotI was cloned into the KpnI site and the EcoRI site of X3.1 (vector name: X4.1). PGKneo-loxP-3' HPRT cleaved from X4.1 with KpnI and AscI was cloned into the KpnI site and the AscI site of V913 (vector name: pVNLH). HS4-CAG-EGFP-HS4 digested with NotI and SalI and then blunt-ended (provided by Dr. Okabe, Osaka University and Dr. Felsenfeld, NIH) was cloned into the EcoRV site of pVNLH (vector name: pVGNLH). The GFP-PGKneo-loxP-3' HPRT cassette cleaved from pVGNLH with SalI and AscI was cloned into the XhoI site and the AscI site of V913-m10LARA (vector name: p16HAMAC1). The targeting vector, the target sequence, and the chromosome allele resulting from homologous recombination are shown in FIG. 12.

As a type 2 vector, a targeting vector targeting the remaining proximal sequence of mouse chromosome 16 was constructed.

As a basic plasmid used for inserting the loxP sequence into DT40 (16MAC), V913 (Lexicon genetics) was used. The DNA sequence of mouse chromosome 16 as a loxP insertion site was obtained from the GenBank database (NC_000082.6). Genomic DNA was extracted as a template from a drug resistant clone, and the sequence of primers used to amplify the 2 target sequence for homologous recombination are shown below.

KpnI_m16 GmLA F:
(SEQ ID NO: 40)
5'-TCGAGGTACCAAGAACAAGCTTCAGAACACAGCCAGAC-3'

XhoI_m16 GmLA R:
(SEQ ID NO: 41)
5'-TCGACTCGAGAACTTGTCACACAGATCCTACTGGAGGTG-3'

-continued

SalI_m16 GmRA F:
(SEQ ID NO: 42)
5'-TCGAGTCGACCCACAGACTGAAGCAATTGACCTCAAAAG-3'

NotI_m16 GmRA R:
(SEQ ID NO: 43)
5'-TCGAGCGGCCGCAAAGCAGTTATCCGCTATTTGGGACCTT-3'

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 4 minutes.

Figure 13:
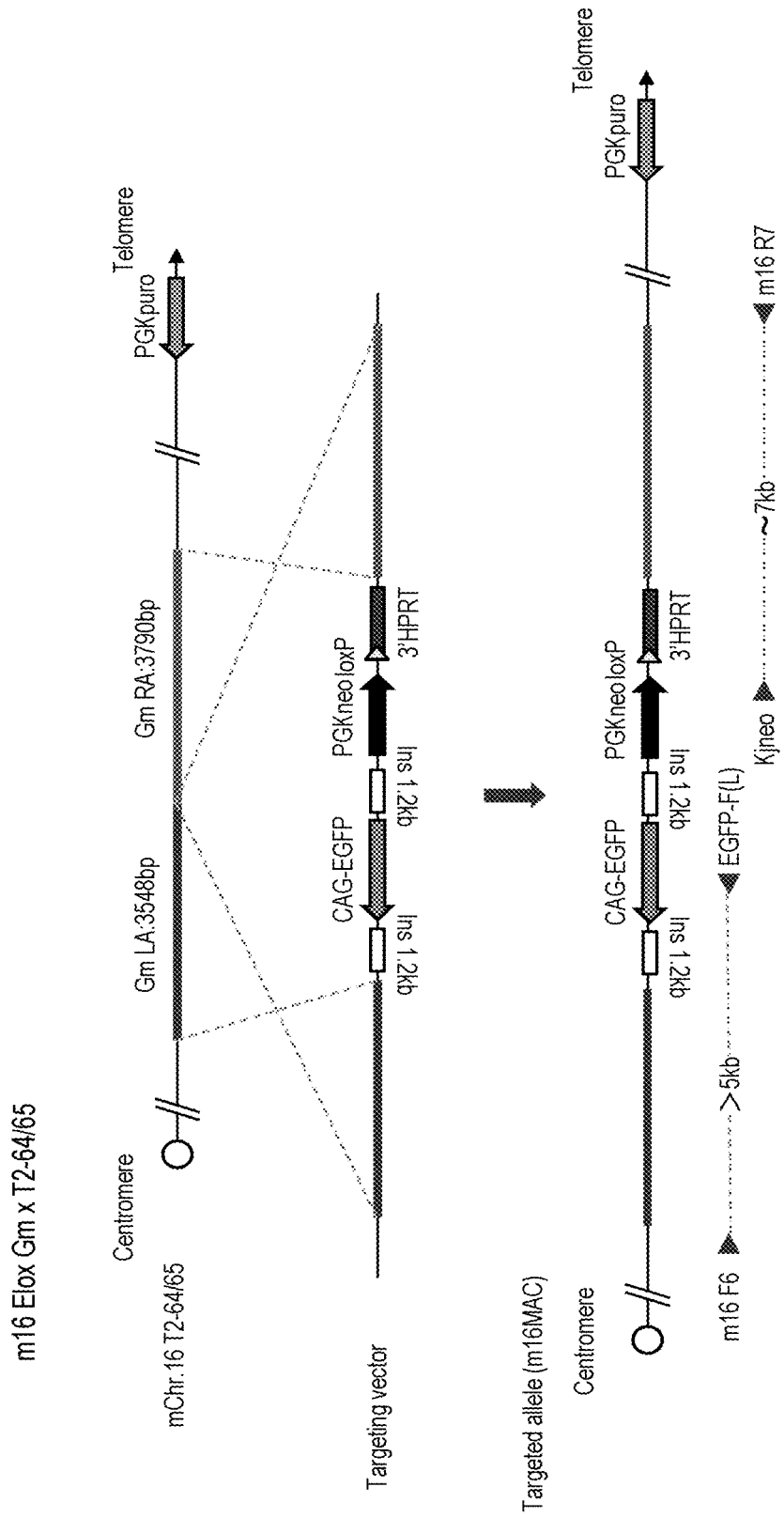
FIG. 13 schematically shows introduction of loxP and the EGFP expression unit into mouse chromosome 16 after the long arm portion was deleted therefrom (pattern 2).

The PCR products were each digested with KpnI (NEB) and XhoI (NEB) and SalI (NEB) and NotI (NEB), respectively, separated by agarose gel, purified, and cloned into the KpnI/XhoI or SalI/NotI site of V913 (vector name: V913-m16Gm). Concerning 3' HPRT-loxP, the oligo-synthesized loxP sequence was cloned into the XbaI site of V820 (Lexicon genetics). 3' HPRT-loxP comprising exons 3 to 9 of the HPRT gene was cloned into EcoRI and AscI of V907 (Lexicon genetics) (vector name: X3.1). Further, the PGK-neo sequence cleaved with KpnI and NotI was cloned into the KpnI site and the EcoRI site of X3.1 (vector name: X4.1). PGKneo-loxP-3' HPRT cleaved from X4.1 with KpnI and AscI was cloned into the KpnI site and the AscI site of V913 (vector name: pVNLH). HS4-CAG-EGFP-HS4 digested with NotI and SalI and then blunt-ended (provided by Dr. Okabe, Osaka University and Dr. Felsenfeld, NIH) was cloned into the EcoRV site of pVNLH (vector name: pVGNLH). The GFP-PGKneo-loxP-3' HPRT cassette cleaved from pVGNLH with SalI and AscI was cloned into the XhoI site and the AscI site of V913-m10LARA (vector name: p16GmMAC1). The targeting vector, the target sequence, and the chromosome allele resulting from homologous recombination are shown in FIG. 13.

[A.2] Transfection and Isolation of G418 Resistant Clone

Chicken DT40 cells were cultured in RPMI 1640 medium (Gibco) supplemented with 10% fetal bovine serum (referred to as "FBS" hereinbelow, Gibco), 1% chicken serum (Gibco), and 10-4 M 2-mercaptoethanol (Sigma). Approximately $10^7$ DT40 (16MAC) T1-14, T2-64, and T2-65 cells were washed once with supplement-free RPMI 1640 medium, suspended in 0.5 ml of supplement-free RPMI 1640 medium, supplemented with 25 µg of the targeting vector p10MAC1 linearized with the restriction enzyme NotI (TAKARA), transferred to a cuvette (Bio-Rad Laboratories, Inc.) for electroporation, and allowed to stand at room temperature for 10 minutes. The cuvette was mounted on Gene Pulser (Bio-Rad Laboratories, Inc.), and voltage was applied under the conditions of 550 V and 25 µF. The resultant was allowed to stand at room temperature for 10 minutes and then cultured for 24 hours. The medium was exchanged with a medium containing G418 (1.5 mg/ml), dispensed into two 96-well culture plates, and then subjected to selection culture for about 2 weeks. Twelve resistant colonies of the p16HAMAC1 vector and 12 resistant colonies of the p16GmMAC1 vector obtained as a result of transfection conducted 1 time were isolated, amplified, and subjected to the subsequent analysis (clone name: DT40 (16MAC1HA and 16MAC1Gm)).

[A.3] Selection of Homologous Recombinant

[A.3.1] PCR Analysis

PCR was performed using the following primers in order to select a recombinant using genomic DNA extracted from the G418 resistant cell line as a template, and whether or not recombination had occurred in a site-directed manner on mouse chromosome 16 was examined. The primer sequences are shown below.

Pattern 1 (p16MAC1HA):
m16 F5 (described above)
EGFP-F(L) (described above)
kjneo (described above)
Puro1 (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 7.5 minutes.

The results indicate that target recombination had occurred in 5 clones derived from DT40 (16MAC) T1-14 (clone name: DT40 (16MAC1HA)).

Pattern 2 (p16GmMAC1):
m16 F6:
(SEQ ID NO: 44)
5'-CATGCACATTTGCTTACACACAGAGGTT-3'

EGFP-F(L) (described above)

kjneo (described above)

m16 R7:
(SEQ ID NO: 45)
5'-ATCTGGGCACTGGGGTACAACTGTTAAT-3'

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 7.5 minutes.

The results indicate that target recombination had occurred in 11 and 9 clones derived from DT40 (16MAC) T2-64 and T2-65 (clone name: DT40 (16MACGm)).

[A.3.2] Two-Color FISH Analysis

Figure 14:
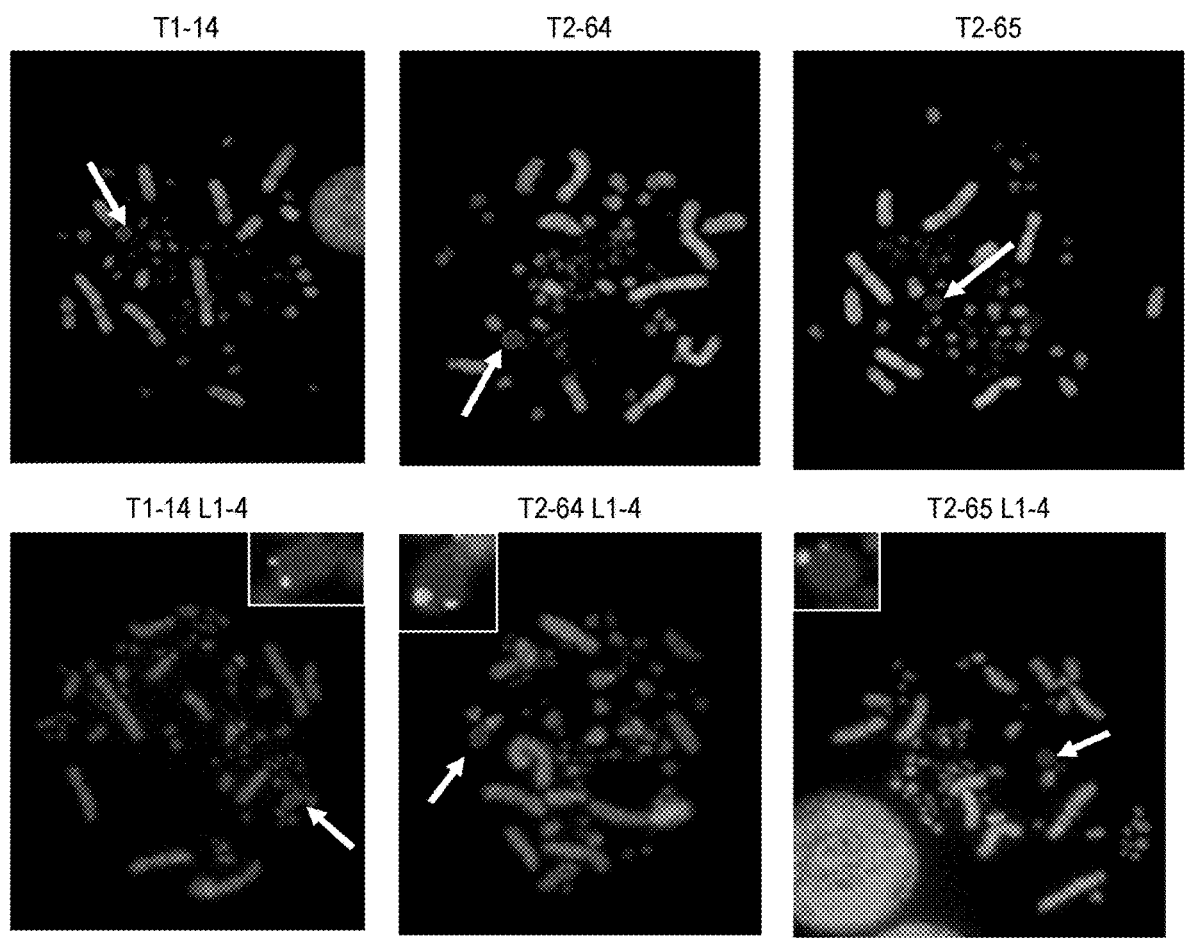
FIG. 14 shows images obtained by FISH analysis conducted before loxP and the EGFP expression unit were introduced into mouse chromosome 16 (16MAC) (16MAC: T1-14, T2-64, and T2-65) and after loxP and the EGFP expression unit were introduced into mouse chromosome 16 (16MAC1HA: T1-14 L1-4; 16MAC1Gm: T2-64 L1-4 and T2-65 L1-4). Arrows indicate 16MAC, 16MAC1HA, and 16MAC1Gm, respectively.

DT40s (16MAC1HA and 16MAC1Gm) obtained above were subjected to two-color FISH analysis in accordance with the method of Matsubara et al. (FISH test protocol, Shujunsha Co., Ltd., 1994). FISH analysis was performed using mouse cot-1 DNA and the GFP-PGKneo-loxP-3' HPRT (pVGNLH) cassette as probes. As a result, a FITC signal derived from the probe was detected near the centromere of the mouse chromosome 10 fragment targeted with the loxP sequence, and a signal that was not observed for the mouse chromosome 16 fragments (e.g., DT40 (16MAC) T1-14, T2-64, and T2-65) before targeted with a negative control was detected. It was thus visually confirmed that site-directed recombination had occurred (FIG. 14). On the basis of the results above, it was concluded that DT40 cell clones comprising the mouse artificial chromosome vectors 16MAC1HA and 16MAC1Gm were obtained.

[B] Introduction of 16MAC1HA and 16MAC1Gm from DT40 Cells Containing the Mouse Artificial Chromosome Vectors 16MAC1HA and 16MAC1Gm into CHO Cells In order to introduce the mouse artificial chromosome vectors 16MAC1HA and 16MAC1Gm into mouse ES cells via CHO cells or to stably insert a target gene (or target genes), such as CYP3A cluster or human antibody gene(s), via loxP as a DNA sequence insertion site of the mouse artificial chromosome vectors 16MAC1HA and 16MAC1Gm within CHO cells, the 16MAC1HA and 16MAC1Gm are introduced into CHO cells.

[B.1] Microcell Fusion and Isolation of Drug Resistant Clone

Microcell fusion is performed using DT40 (16MAC1HA) and DT40 (16MAC1Gm) as donor cells and CHO (HPRT⁻), i.e. the CHO hprt-deficient cell (Accession Number: JCRB0218; the Health Science Research Resources Bank), in the same manner as described above. The G418 resistant colonies obtained by microcell fusion are isolated, amplified, and subjected to the subsequent analysis (clone names: CHO (HPRT⁻; 16MAC1HA and 16MAC1Gm)).

[B.2] Selection of Drug Resistant Clone

[B.2.1] PCR Analysis

PCR is performed using the following primers in order to select a recombinant using genomic DNA extracted from the G418 resistant cell line as a template, and whether or not the mouse artificial chromosomes 16MAC1HA and 16MAC1Gm have been introduced into CHO cells is confirmed. The primer sequences are shown below.

Confirmation of 16MAC1HA:
- m16 F5 (described above)
- EGFP-F(L) (described above)
- kjneo (described above)
- PuroI (described above)

Confirmation of 16MAC1Gm:
- m16 F6 (described above)
- EGFP-F(L) (described above)
- kjneo (described above)
- m16 R7 (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under recommended conditions. Temperature and cycle conditions are as follows: thermal denaturation at 98° C. for 1 minute is followed by 35 cycles of 98° C. for 15 seconds and 68° C. for 7.5 minutes. PCR-positive clones are subjected to the subsequent analysis.

[B.2.2] Mono-Color FISH Analysis

The CHO (HPRT⁻; 16MAC1HA and 16MAC1Gm) clones obtained above are subjected to FISH analysis using mouse cot-1 DNA as a probe in accordance with the report of Shinohara et al. (Human Molecular Genetics, 10: 1163-1175, 2001). As a result, it is confirmed that the mouse artificial chromosome vectors 16MAC1HA and 16MAC1Gm have been introduced into CHO cells.

[Example 6] Evaluation of Stability of Mouse Artificial Chromosome Vectors in Mouse Individuals Stability of 10MAC1, 10MAC1HA, and 10MAC1Gm in mouse ES cells is examined, and transgenic mice comprising the mouse artificial chromosome vectors introduced thereinto are prepared to examine stability in individual tissues.

[A] Introduction of Mouse Artificial Chromosome Vectors 10MAC1, 16MAC1HA, and 16MAC1Gm from CHO Cells Containing Mouse Artificial Chromosome Vectors into Mouse ES Cells In order to examine stability of mouse artificial chromosome vectors 10MAC1, 16MAC1HA, and 16MAC1Gm in mouse ES cells and in mouse individuals, the mouse artificial chromosomes 10MAC1, 16MAC1HA, and 16MAC1Gm are introduced into mouse ES cells to prepare chimeric mice and transgenic mice comprising the relevant mouse artificial chromosome vectors 10MAC1, 16MAC1HA, and 16MAC1Gm.

[A.1] Microcell Fusion and Isolation of Drug Resistant Clone

Recipient cells, i.e. CHO (HPRT⁻; 10MAC1), CHO (HPRT⁻; 16MAC1HA), and CHO (HPRT⁻; 16MAC1Gm), were cultured in culture dishes. When culture reached confluency, the medium was exchanged with F12 medium supplemented with 20% FBS and 0.1 µg/ml colcemid, culture was performed for additional 48 hours, the medium was exchanged with a fresh F12 medium supplemented with 20% FBS and 0.1 µg/ml colcemid, and incubation was performed overnight to form microcells. The culture medium was removed, the centrifuge flask was filled with a cytochalasin B (10 µg/ml, Sigma) solution kept warm at 37° C. in advance, and centrifugation was then performed at 34° C. and 8,000 rpm for 1 hour. Microcells are suspended in serum-free DMEM and purified using 8-µm, 5-µm, and 3-µm filters. After purification, the microcells are centrifuged at 2,000 rpm for 10 minutes and then suspended in 5 ml of serum-free DMEM. The microcells are suspended in 5 ml of serum-free DMEM and purified using 8-µm, 5-m, and 3-µm filters. Thereafter, the microcells are centrifuged at 2,000 rpm for 10 minutes.

As donor cells, B6-ES, which is a C57B6 line-based mouse ES cell, B6 (HPRT⁻), which is a HPRT-deficient cell line obtained by treating the B6-ES cell with 6TG, TT2F, which is a C57B6×CBA lineage-based F1 mouse ES cell, and KO56 (HPRT⁻), which is a HPRT-deficient cell line obtained by treating the TT2F cell with 6TG, were used. Cell culture was performed in DMEM (Dulbecco's Modified Eagle's Medium-high glucose: SIGMA) supplemented with 10% FCS, LIF (Muerin Leukemia Inhibitory Factor), 1×10⁻⁵ M 2-ME (2-mercaptoethanol: SIGMA), L-glutamine (3.5 g/ml: GIBCO), a sodium pyruvate solution (3.5 g/ml: GIBCO), and MEM non-essential amino acid (0.125 mM: GIBCO) in the presence of 5% CO₂ at 37° C. After washing the cell surface of mouse ES cells twice with PBS (−), the cells were dispersed with trypsin treatment and recovered with a culture medium in which 10% FBS was added to DMEM. Centrifugation was performed at 1,500 rpm, the supernatant was removed, re-suspended in 5 ml of serum-free culture medium, and gently added to the serum-free culture medium containing microcell pellets after centrifugation. It was further centrifuged at 1,200 rpm. The supernatant was removed, and the cell fusion was performed exactly for 1 minute and 30 seconds with 0.5 ml of a PEG1000 (Wako) solution (prepared by completely dissolving 5 g of PEG1000 in serum-free DMEM and adding 1 ml of dimethyl sulfoxide thereto, followed by sterilization via filtration). A serum-free culture medium (DMEM, 13 ml) was gently added and centrifuged at 1,200 rpm. The supernatant was removed, common culture medium for mouse ES cells was added, and mitomycin-treated G418-resistant mouse embryonic fibroblasts were seeded as feeder cells in two 10-cm cell culture dishes, followed by incubation overnight. G418 was added at a concentration of 250 µg/ml and subjected to selection culture for 3 to 4 weeks (clone names: B6-ES (10MAC1, 16MAC1HA, and 16MAC1Gm); B6 (HPRT⁻; 10MAC1, 16MAC1HA, and 16MAC1Gm); TT2F (10MAC1, 16MAC1HA, and 16MAC1Gm); and KO56 (HPRT⁻; 10MAC1, 16MAC1HA, and 16MAC1Gm)). As a result, 13 clones of TT2F (10MAC1) drug resistant colonies were isolated, amplified, and subjected to the subsequent analysis.

[A.2] Selection of Drug Resistant Clone

[A.2.1] PCR Analysis

PCR is performed using the following primers in order to select a recombinant using genomic DNA extracted from the G418 resistant cell line as a template, and whether or not the mouse artificial chromosome vectors have been introduced into mouse ES cells is confirmed. The primer sequences are shown below.

Confirmation of 10MAC1:
 m10 F6 (described above)
 PuroI (described above)
 m10 F1 (described above)
 EGFP-F(L) (described above)
 kj neo (described above)
 m10 R2 (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under recommended conditions. Temperature and cycle conditions were as follows: thermal denaturation at 98° C. for 1 minute was followed by 35 cycles of 98° C. for 15 seconds and 68° C. for 8 minutes and 2.5 minutes. The resulting 9 PCR-positive clones are subjected to the subsequent analysis.

Confirmation of 16MAC1HA:
 m16 F5 (described above)
 EGFP-F(L) (described above)
 kjneo (described above)
 PuroI (described above)

Confirmation of 16MAC1Gm:
 m16 F6 (described above)
 EGFP-F(L) (described above)
 kjneo (described above)
 m16 R7 (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under recommended conditions. Temperature and cycle conditions were as follows: thermal denaturation at 98° C. for 1 minute is followed by 35 cycles of 98° C. for 15 seconds and 68° C. for 7.5 minutes. PCR-positive clones are subjected to the subsequent analysis.

[A.2.2] Mono-Color FISH Analysis

Figure 15:
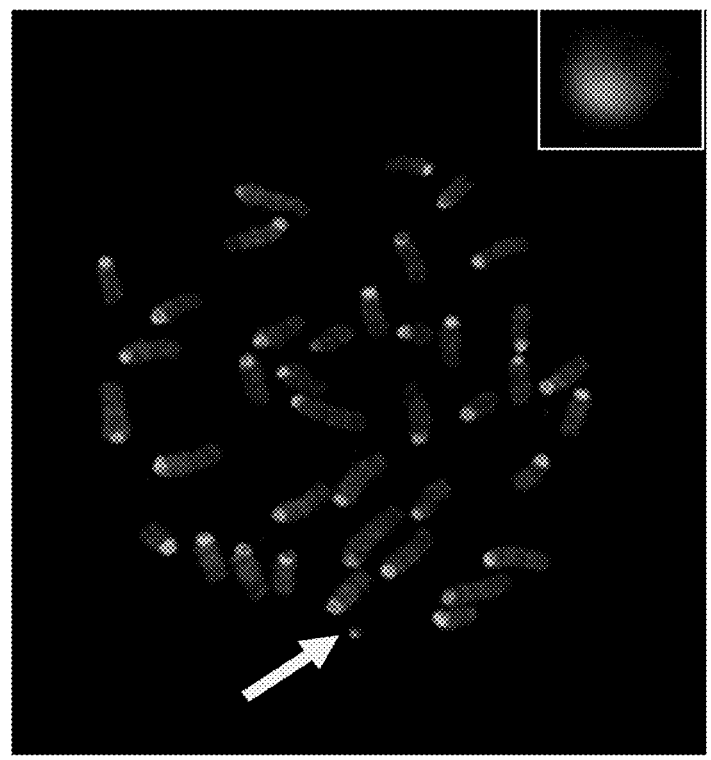
FIG. 15 shows an image obtained by FISH analysis of a mouse ES cell (TT2F) retaining 10MAC1. An arrow indicates 10MAC1.

B6-ES (MAC1), B6 (HPRT⁻; 10MAC1, 16MAC1HA, and 16MAC1Gm), TT2F (10MAC1, 16MAC1HA, and 16MAC1Gm), and KO56 (HPRT⁻; 10MAC1, 16MAC1HA, and 16MAC1Gm) clones obtained above were subjected to FISH analysis using mouse minor satellite DNA as a probe in accordance with the report of Shinohara et al. (Human Molecular Genetics, 10: 1163-1175, 2001) to confirm that the mouse artificial chromosome vectors were retained. The number of endogenous mouse chromosomes as the normal karyotype was confirmed to be 40 for B6-ES and 39 for KO56. As a result, it was concluded that the mouse artificial chromosome vectors 10MAC1, 16MAC1HA, and 16MAC1Gm had been introduced into mouse ES cells. PCR-positive 9 clones of TT2F-ES (10MAC1) were subjected to FISH analysis and 2 clones were confirmed to retain MAC1 at a high rate and to have normal karyotype (FIG. 15).

[B] Stability of Mouse Artificial Chromosome Vectors 10MAC1, 16MAC1HA, and 16MAC1Gm

[B.1] Stability of Mouse Artificial Chromosome Vectors 10MAC1, 16MAC1HA, and 16MAC1Gm in CHO Cells The CHO clones obtained above (e.g., CHO (HPRT⁻; 10MAC1) obtained in Example 3) are subjected to long-term and non-selection culture at 0 to 25 PDL and then to FISH analysis to determine the rate of 10MAC1-retaining cells.

[B.2] Stability of Mouse Artificial Chromosome Vectors 10MAC1, 16MAC1HA, and 16MAC1Gm in Mouse ES Cells The mouse ES clones obtained above (e.g., KO56 (10MAC1) and TT2F (10MAC1) obtained in Example 6 [A]) are subjected to long-term and non-selection culture at 0 to 100 PDL and then to FISH analysis to determine the rate of 10MAC-retaining cells.

[B.3] Preparation of Chimeric Mice Retaining Mouse Artificial Chromosome Vectors 10MAC1, 16MAC1HA, and 16MAC1Gm Using the ES cell clones obtained in Example 6 [A] above, chimeric mice were prepared according to the method described by Tomizuka et al. (Nature Genet., 16: 133, 1997). As a host cell, an eight-cell stage embryo obtained by sexual crossbreeding of MCH (ICR) (white, purchased from CLEA Japan, Inc.) is used. Whether or not newborn mice resulting from transplantation of an injected embryo into a foster mother are chimeric is determined on the basis of the coat color. An embryo into which the 10MAC1-retaining ES clone TT2F (10MAC1) (e.g., KO56 10MAC1 obtained in Example 6 [A]) had been injected was transplanted into a foster mother. A chimeric rate of the resulting chimeric mice was determined based on the coat color (a dark brown area was observed). Thus, whether or not ES cell lines (KO56 and TT2F) comprising the mouse artificial chromosome vector 10MAC1 retained a chimera forming ability; that is, an ability of differentiation into normal tissue of a mouse individual, was confirmed.

Figure 16:
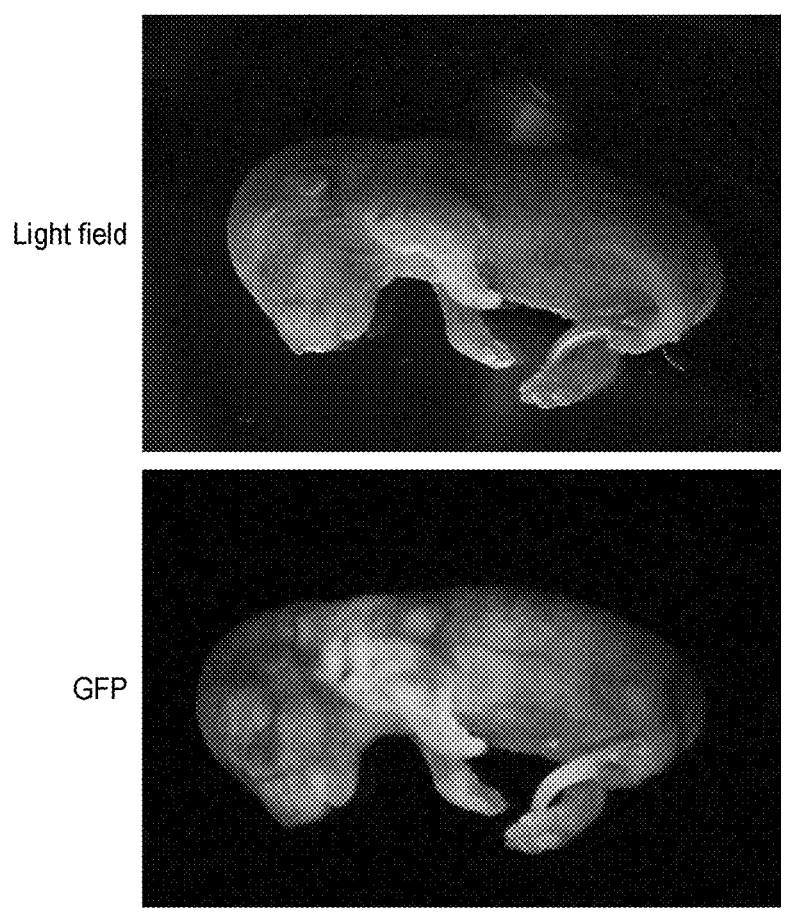
FIG. 16 shows a light field image of a mouse with progeny-transmitted 10MAC1 (upper panel) and a GFP fluorescence (lower panel). Since 10MAC1 comprises a GFP expression cassette introduced thereinto, a 10MAC1-retaining cell is GFP fluorescent-positive.

[B.4] Transmission of 10MAC1, 16MAC1HA, and 16MAC1Gm from Chimeric Mice Retaining Mouse Artificial Chromosome Vectors 10MAC1, 16MAC1HA, and 16MAC1Gm to Progeny The female chimeric mice (chimeric rate: about 100%) prepared in [B. 3] above were subjected to crossbreeding with male mice MCH (ICR) (white, purchased from CLEA Japan, Inc.). New-born mice born from chimeric mice were examined as to retention of various mouse artificial chromosome vectors with the aid of GFP fluorescence. The mouse lineages to which that each mouse artificial chromosome has been progeny-transmitted are referred to as TCs (10MAC1, 16MAC1HA, and 16MAC1Gm). Individuals in which GFP fluorescent protein expression has been observed throughout the body were selected for progeny-transmitted individuals obtained from TT2F (MAC1)-derived chimeric mice (FIG. 16).

[B.5] Stability of 10MAC1, 16MAC1HA, and 16MAC1Gm in Somatic Cells of TC (10MAC1, 16MAC1HA, and 16MAC1Gm) Mouse Lineages

[B.5.1] Observation Under Stereo Fluorescence Microscope

The male and female TC (10MAC1, 16MAC1HA, and 16MAC1Gm) mice obtained above were subjected to stereo fluorescence microscopic observation in the brain, thymus, heart, lung, liver, kidney, spleen, small intestine, muscle, and testis (or ovary). As a result, all tissues are observed to be GFP positive.

[B.5.2] FACS Analysis of Hematopoietic Cells

Using an antibody (Becton, Dickinson and Company) specific for B cells (CD19), T cells (CD4 and CD8), and megakaryocyte (CD41), GFP positive rates of bone marrow and spleen cells are examined.

[B.5.3] Fluorescence In Situ Hybridization (FISH) Analysis

Using the tail fibroblast prepared from the same individual as the above, FISH analysis is performed using mouse minor satellite DNA as a probe in accordance with the report of Shinohara et al. (Human Molecular Genetics, 10: 1163-1175, 2001). As a result, the presence of MAC is visually confirmed, and MAC is confirmed to be maintained independently of the host chromosome.

[Example 7] Preparation of Human-Antibody-Producing Mice and Rats Using Novel Mouse Artificial Chromosome Vector (IGHK-NAC)

Functions of the mouse artificial chromosome vectors 10MAC1, 16MAC1HA, and 16MAC1Gm were evaluated, the vectors to be used were selected based on the evaluation results (the selected mouse artificial chromosome is referred to as "NAC"), and the human antibody genes (IGH and IGK) were introduced thereinto to prepare human-antibody-producing mice and rats (FIG. 17). 10MAC1 was selected and subjected to the subsequent experiment as NAC.

[A] Transfer of Modified Human Chromosome 2 into CHO Cell Retaining NAC

Modified human chromosome 2 is transferred from CHO cells retaining modified human chromosome 2 into CHO cells retaining NAC.

[A.1] Transfer of Modified Human Chromosome 2 into Hprt-Deficient CHO Cell Retaining NAC Via Microcell Fusion CHO cells retaining the modified human chromosome 2 (CHO hChr2LF) as donor cells were cultured in cell culture dishes. When the culture reached confluency, the medium was exchanged with F12 medium supplemented with 20% FBS and 0.1 µg/ml colcemid, culture was performed for an additional 48 hours, the medium was exchanged with a fresh F12 medium supplemented with 20% FBS and 0.1 µg/ml colcemid, and incubation was performed overnight to form microcells. The culture medium was removed, the centrifuge flask was filled with a cytochalasin B (10 µg/ml, Sigma) solution kept warm at 37° C. in advance, and centrifugation was then performed at 34° C. and 8,000 rpm for 1 hour. Microcells were suspended in serum-free DMEM and purified using 8-µm, 5-µm, and 3-µm filters. After purification, the microcells were suspended in 2 ml of 0.05 mg/ml PHA-P (Sigma) solution in DMEM, and then to the microcells is added Hprt-deficient CHO cell line, as a recipient cell, which had been cultured to reach cofluency in 6-cm cell culture dishes, following removal of the culture medium. Incubation was performed for 15 minutes, and the microcells were then allowed to adhere to CHO cells. Thereafter, cell fusion was exactly performed for 1 minute with 1 ml of a PEG1000 (Wako) solution (prepared by completely dissolving 5 g PEG1000 in serum-free DMEM, adding 1 ml dimethyl sulfoxide, and then sterilizing via filtration). In order to remove PEG, the cells were washed with 5 ml serum-free DMEM 4 times, followed by addition of CHO culture solution. After 24 hours, the cells were seeded on ten 10-cm cell culture dishes, added with 8 g/ml blasticidin S, and subjected to 10-days selection culture. The resulting drug resistant cells were subjected to the subsequent analysis.

[A.2] Selection of Drug Resistant Clone Via PCR Analysis

PCR is performed using the genome extracted from the blasticidin S resistant cell line as a template to confirm the retention of the modified human chromosome 2. The primer sequences are shown below.

```
Primers for confirmation of loxP sequence
on modified human chromosome 2:
cos138 sp L:
                                      (SEQ ID NO: 46)
5'-CTGAGAAGAGTCATTGTTTATGGTAGACT-3' cos138 sp R:
                                      (SEQ ID NO: 47)
5'-ATCCCCATGTGTATCACTGGCAAACTGT-3' x6.1cosRa L:
                                      (SEQ ID NO: 48)
5'-GGGGAATAAACACCCTTTCCAAATCCTC-3' x6.1cosRa R:
                                      (SEQ ID NO: 49)
5'-ACCAAGTAACCGATCAAACCAACCCTTG-3'
```

PCR is performed using Accuprime Taq DNA polymerase (Thermo Fisher Scientific) for cos138 sp L and cos138 sp R primers and buffers and dNTPs (dATP, dCTP, DGTP, and dTTP) included in the kit, under recommended conditions. Temperature and cycle conditions are as follows: thermal denaturation at 94° C. for 2 minutes was followed by 35 cycles of 94° C. for 15 seconds, 60° C. for 15 seconds, and 68° C. for 5 minutes.

PCR is performed using KOD FX (TOYOBO) for x6.1cosRa L and x6.1cosRa R primers and buffers and dNTPs (dATP, dCTP, DGTP, and dTTP) included in the kit, under recommended conditions. Temperature and cycle conditions are as follows: thermal denaturation at 98° C. for 1 minute was followed by 30 cycles of 98° C. for 15 seconds and 68° C. for 12 minutes.

```
Primers for confirmation of FRT sequence
on modified human chromosome 2:
kD9 tcLa L:
                                      (SEQ ID NO: 50)
5'-TGAGAACACAGGGGTCTCCATTCTGACT-3' kD9 tcLa R:
                                      (SEQ ID NO: 51)
5'-ACAATCAACAGCATCCCCATCTCTGAAG-3' kD9 tcRa L:
                                      (SEQ ID NO: 52)
5'-GACGTGCTACTTCCATTTGTCACGTCCT-3' kD9 tcRa R:
                                      (SEQ ID NO: 53)
5'-TGGTCACTGAAGCTTTCCATCTGCTCTT-3'
```

KOD FX (TOYOBO) was used for these primers, and buffers and dNTPs (dATP, dCTP, DGTP, and dTTP) included in the kit are used under recommended conditions. Temperature and cycle conditions were as follows: thermal denaturation at 98° C. for 1 minute is followed by 35 cycles of 98° C. for 15 seconds and 68° C. for 5 minutes.

In addition, whether or not the region of interest on human chromosome 2 has been retained is confirmed using primers. The primer sequences are shown below.

```
D2S177 F:
                                      (SEQ ID NO: 54)
5'-AGCTCAGAGACACCTCTCCA-3'

D2S177 R:
                                      (SEQ ID NO: 55)
5'-CTGTATTAGGATACTTGGCTATTGA-3'

FABP1-F:
                                      (SEQ ID NO: 56)
5'-TATCAAGGGGTGTCGGAAATCGTG-3'

FABP1-R:
                                      (SEQ ID NO: 57)
5'-ACTGGGCCTGGGAGAACCTGAGACT-3'

EIF2AK3-F:
                                      (SEQ ID NO: 58)
5'-AGGTGCTGCTGGGTGGTCAAGT-3'

EIF2AK3-R:
                                      (SEQ ID NO: 59)
5'-GCTCCTGCAAATGTCTCCTGTCA-3'

RPIA-F:
                                      (SEQ ID NO: 60)
5'-CTTACCCAGGCTCCAGGCTCTATT-3'

RPIA-R:
                                      (SEQ ID NO: 61)
5'-CTCTACCTCCCTACCCCATCATCAC-3'

IGKC-F:
                                      (SEQ ID NO: 62)
5'-TGGAAGGTGGATAACGCCCT-3'

IGKC-R:
                                      (SEQ ID NO: 63)
5'-TCATTCTCCTCCAACATTAGCA-3'

IGKV-F:
                                      (SEQ ID NO: 64)
5'-AGTCAGGGCATTAGCAGTGC-3'

IGKV-R:
                                      (SEQ ID NO: 65)
5'-GCTGCTGATGGTGAGAGTGA-3'

Vk3-2 F:
                                      (SEQ ID NO: 66)
5'-CTCTCCTGCAGGGCCAGTCA-3'

Vk3-2 R:
                                      (SEQ ID NO: 67)
5'-TGCTGATGGTGAGAGTGAACTC-3'

D2S159_1 F:
                                      (SEQ ID NO: 68)
5'-CTCTAACTGAATCAAGGGAATGAAC-3'

D251591_R:
                                      (SEQ ID NO: 69)
5'-AGCAGTTTGAGTTTAGGATGAAGG-3'
```

PCR was performed using Ampli Taq Gold (Applied Biosystems) as Taq polymerase and buffers and dNTPs (dATP, dCTP, DGTP, and dTTP) included in the kit under recommended conditions. Temperature and cycle conditions were as follows: thermal denaturation at 95° C. for 10 minutes was followed by 35 cycles of 95° C. for 30 seconds, 60° C. for 30 seconds, and 72° C. for 1 minute.

PCR-positive clones were subjected to the subsequent analysis. As a result, a clone retaining the modified human chromosome 2 and NAC (a novel artificial chromosome vector) was obtained.

[A.3] Two-Color FISH Analysis

Figure 18:
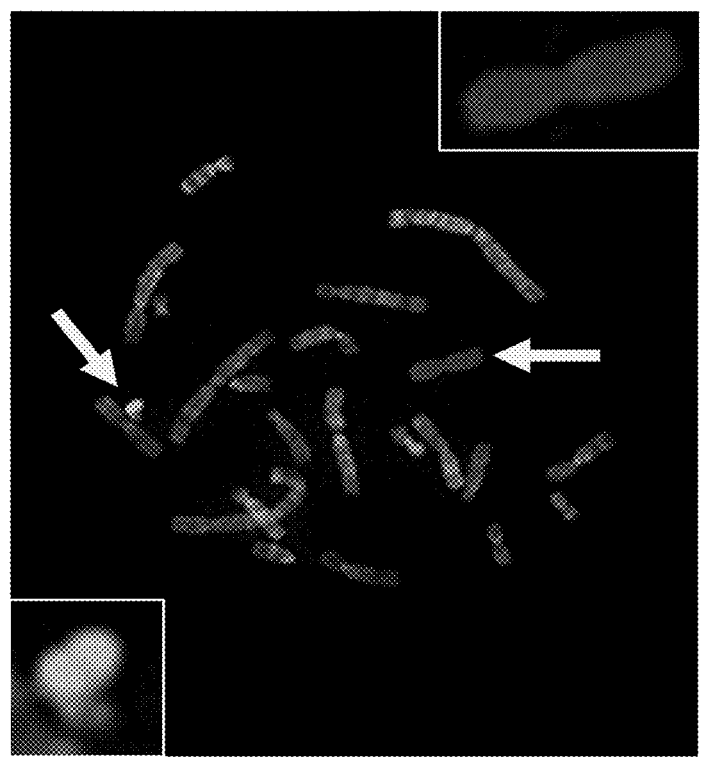
FIG. 18 shows an image obtained by FISH analysis of a CHO cell retaining modified human chromosome 2 and NAC (which is a novel artificial chromosome vector of the present invention). The left arrow indicates NAC and the right arrow indicates modified human chromosome 2.

PCR-positive clones on the basis of the above results were subjected to two-color FISH analysis in accordance with the method of Matsubara et al. (FISH test protocol, Shujunsha Co., Ltd., 1994). FISH analysis was performed using human cot-1 DNA and mouse cot-1 DNA as probes to confirm that the modified human chromosome 2 and NAC were stably maintained independently of the host chromosome (FIG. 18).

[B] Translocation Cloning of Human Chromosome 2 Containing IGK Region into Mouse Artificial Chromosome Vector (NAC)

Figure 19:
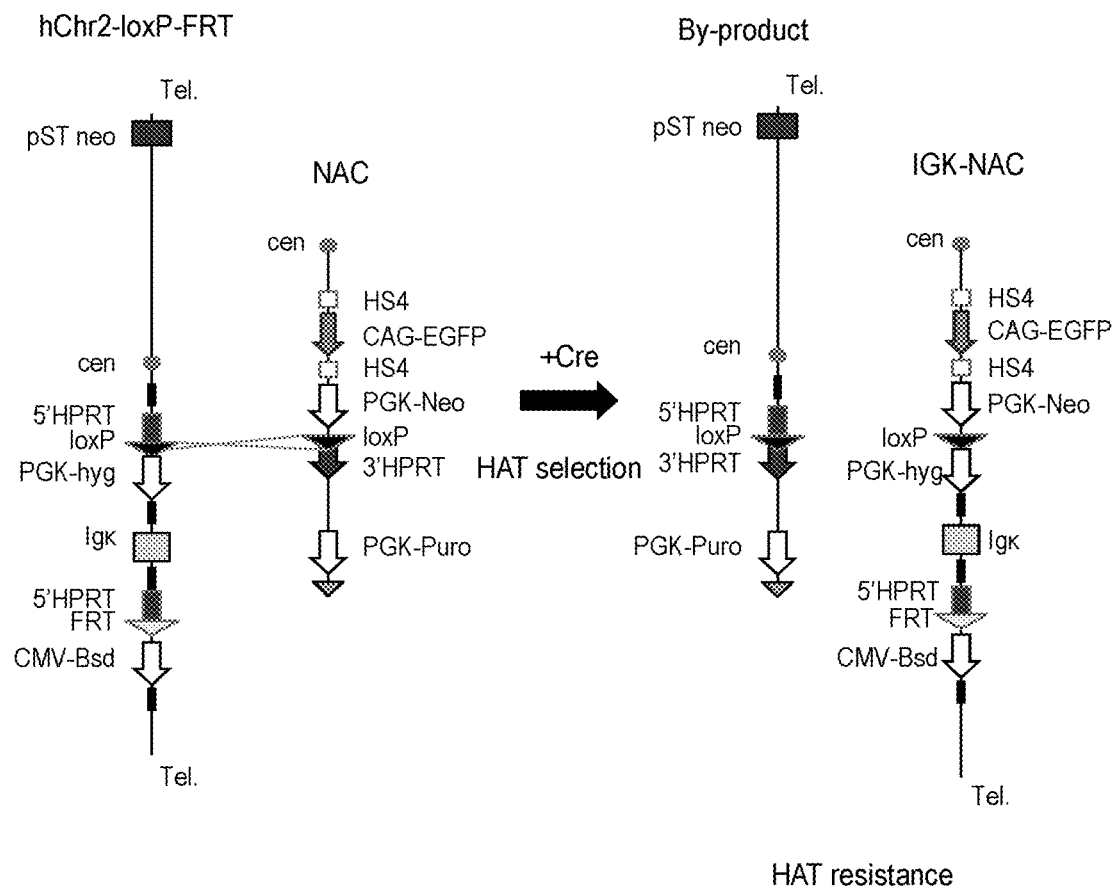
FIG. 19 schematically shows construction of IGK-NAC via reciprocal translocation caused by Cre/loxP system. Concerning HAT resistance, when recombination takes place in the loxP sequence, 5' HPRT is ligated to 3' HPRT, the HPRT gene is reconstructed, HAT resistance is acquired, and selection can be thus made with the aid of HAT. In the figure, Igκ indicates the immunoglobulin light chain κ gene (gene locus), Cen. represents a centromere, Tel. represents a telomere, HS4 represents an insulator, CAG, CMV, and PGK each represent a promoter, EGFP represents a gene encoding a fluorescent protein, Bsd, hyg, Puro, and Neo each represent a drug resistant gene, and HPRT represents a hypoxanthine-guanine phosphoribosyltransferase gene.

In the CHO cells retaining NAC, the IGK region on the human chromosome 2 was cloned into NAC via translocation. For the translocation cloning, the human chromosome 2 and NAC were subjected to reciprocal translocation using the Cre/loxP system, so as to introduce the IGK region into NAC (FIG. 19).

[B.1] Acquisition of HAT Resistant Chromosome Recombinant Via Cre Expression

Because NAC comprises a loxP site introduced thereinto, the NAC would undergo recombination with the loxP site of the modified human chromosome 2 in the presence of Cre recombinase. When recombination occurs, 5' HPRT in the human chromosome 2 region, as a bi-product, that is not introduced into NAC, is ligated to 3' HPRT at 3'-end of NAC as a by-product, thereby resulting in reconstitution of the HPRT gene, and CHO(hprt−/−) acquires HAT resistance.

When the Hprt-deficient CHO cells retaining modified human chromosome 2 and NAC reach confluency in 10-cm cell culture dishes, 18 µg of a Cre expression plasmid (vector name: pBS185) is added using Lipofectamine 2000 (Thermo Fisher Scientific) with reference to the manufacturer's instructions. The culture medium is exchanged with the fresh medium 6 hours after the addition, the cells are seeded in ten 10-cm cell culture dishes 24 hours later, and drug selection is then performed with using 1×HAT (Sigma) and 4 µg/ml blasticidin. The drug resistant clones obtained are subjected to the subsequent analysis.

[B.2] Selection of Drug Resistant Clone Via PCR Analysis

PCR is performed using genomic DNA extracted from HAT resistant cell line as template and the primers shown below to select clones resulting from reciprocal translocation, and whether or not reciprocal translocation has occurred between the human chromosome 2 fragment and NAC is confirmed. The primer sequences are shown below.

```
TRANS L1 (described above)

TRANS R1 (described above)

KJneo:
                                      (SEQ ID NO: 70)
5'-CATCGCCTTCTATCGCCTTCTTGACG-3'

PGKr-2:
                                      (SEQ ID NO: 71)
5'-ATCTGCACGAGACTAGTGAGACGTGCTA-3'
```

PCR is performed using the primers shown above, LA taq (Takara), and buffers and dNTPs (dATP, dCTP, DGTP, and dTTP) included in the kit under recommended conditions. Temperature and cycle conditions are as follows: thermal denaturation at 98° C. for 1 minute was followed by 30 cycles of 94° C. for 10 seconds, 60° C. for 30 seconds, and 72° C. for 3 minutes.

In addition, PCR is performed to confirm whether or not the human chromosome 2 region and the FRT sequence are maintained. The primers are shown below.

Primers for Confirmation of Human Chromosome 2 Region:
D2S177 F (described above)
D2S177 R (described above)

FABP1-F (described above)
FABP1-R (described above)
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)
D2S159_1 F (described above)
D2S159_1 R (described above)

PCR is performed using Ampli Taq Gold (Applied Biosystems) as Taq polymerase and buffers and dNTPs (dATP, dCTP, DGTP, and dTTP) included in the kit under recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

Primers for Confirmation of FRT Sequence on Human Chromosome 2:

kD9 tcLa L (described above)
  kD9 tcLa R (described above)
  kD9 tcRa L (described above)
  kD9 tcRa R (described above)

PCR is performed using the primers shown above, KOD FX (TOYOBO), and buffers and dNTPs (dATP, dCTP, DGTP, and dTTP) included in the kit under recommended conditions. Temperature and cycle conditions are as follows: thermal denaturation at 98° C. for 1 minute was followed by 35 cycles of 98° C. for 15 seconds and 68° C. for 5 minutes. PCR-positive clones are subjected to the subsequent analysis.

[B.3] Two-Color FISH Analysis

PCR-positive clones are subjected to FISH analysis using human cot-1 DNA and mouse cot-1 DNA as probes to confirm that reciprocal translocation has occurred between NAC and the modified human chromosome 2 and to detect that IGK-NAC comprising the IGK region introduced into NAC is retained independently of the by-product. The clone is called "CHO IGK-NAC."

[C] Transfer of IGK-NAC into CHO (Hprt−/−) Cell Line Retaining Modified Human Chromosome 14

Figure 20:
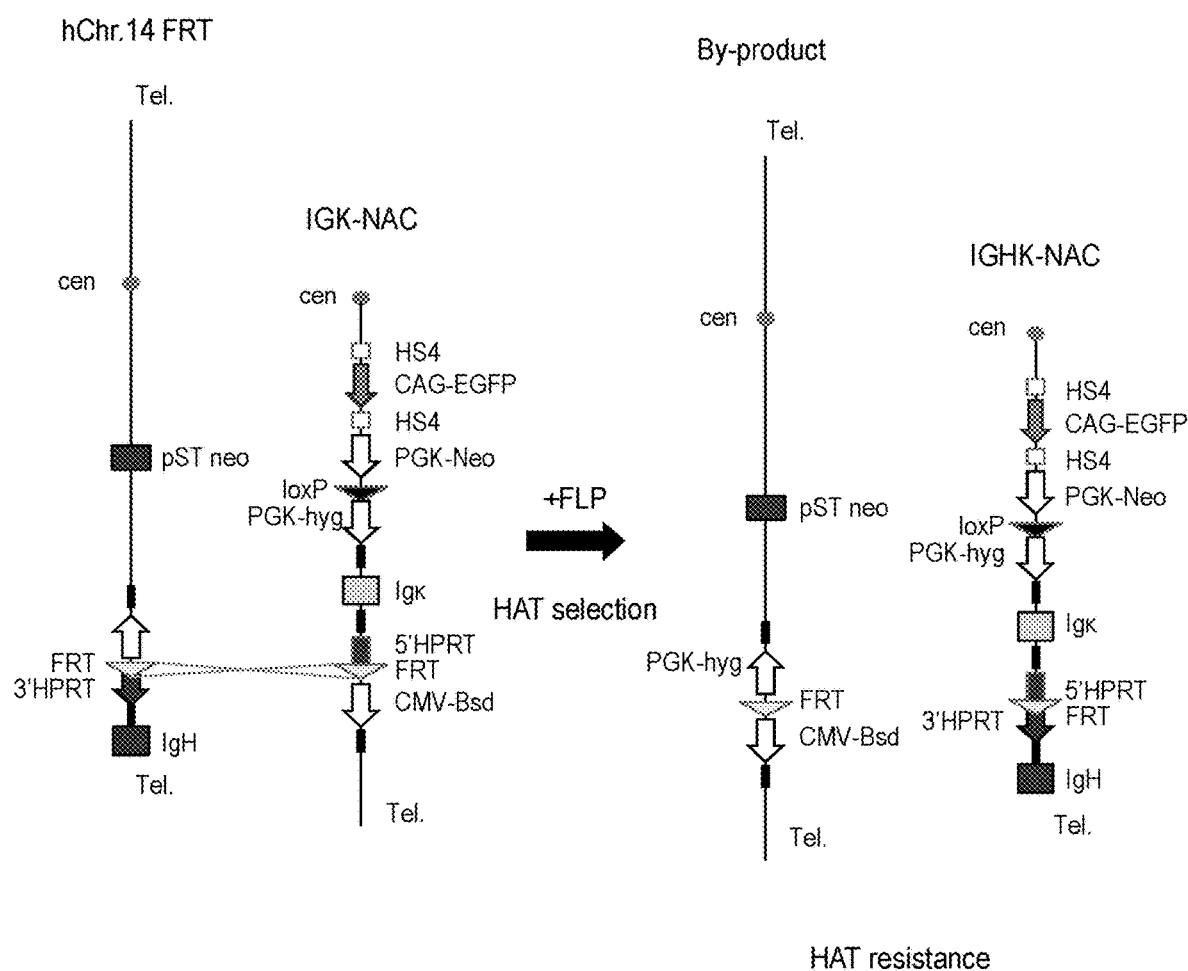
FIG. 20 schematically shows construction of IGHK-NAC via reciprocal translocation caused by the Flp/FRT system. Concerning HAT resistance, when recombination takes place in the FRT sequence, 5' HPRT is ligated to 3' HPRT, the HPRT gene is reconstructed, HAT resistance is acquired, and selection can be thus made with the aid of HAT. In the figure, Igκ represents the immunoglobulin light chain κ gene (gene locus), IgH represents the immunoglobulin heavy chain gene (gene locus), Cen. represents a centromere, Tel. represents a telomere, HS4 represents an insulator, CAG, CMV, and PGK each represent a promoter, EGFP represents a gene encoding a fluorescent protein, Bsd, hyg, and Neo each represent a drug resistant gene, and HPRT represents a hypoxanthine-guanine phosphoribosyltransferase gene.

The prepared IGK-NAC was transferred into the CHO (hprt−/−) cell line retaining the modified human chromosome 14, so as to introduce the IGH region into IGK-NAC via recombination using the FRT/Flp system. Thus, IGHK-NAC was prepared (FIG. 20).

[C.1] Microcell Fusion and Isolation of Drug Resistant Clone

The donor cells (CHO IGK-NAC) are cultured in cell culture dishes. When culture reach confluency, the medium is exchanged with F12 medium supplemented with 20% FBS and 0.1 µg/ml colcemid, culture is performed for additional 48 hours, the medium is exchanged with a fresh F12 medium supplemented with 20% FBS and 0.1 µg/ml colcemid, and incubation is performed overnight to form microcells. The culture medium is removed, the centrifuge flask is filled with a cytochalasin B (10 µg/ml, Sigma) solution kept warm at 37° C. in advance, and centrifugation is then performed at 34° C. and 8,000 rpm for 1 hour. Microcells are suspended in serum-free DMEM and purified using 8-µm, 5-µm, and 3-µm filters. After purification, the microcells are suspended in 2 ml of 0.05 mg/ml PHA-P (Sigma) solution in DMEM, and then to the microcells are added CHO hprt−/−14FRT cells, as recipient cells, which have been cultured to reach confluency in 6-cm cell culture dishes, following removal of culture medium. Incubation is performed for 15 minutes, and the microcells are then allowed to adhere to CHO cells. Thereafter, cell fusion is performed exactly for 1 minute with 1 ml of a PEG1000 (Wako) solution (prepared by completely dissolving 5 g PEG1000 in 6 ml of the serum-free DMEM and adding 1 ml of dimethyl sulfoxide thereto, followed by sterilization via filtration). The cells are washed with 5 ml serum-free DMEM 4 times to remove PEG, and the CHO culture solution is then added. The cells are seeded in ten 10-cm cell culture dishes 24 hours later, 600 µg/ml G418 and 6 µg/ml blasticidin are added, and selection culture is then conducted for 10 days. The resulting drug-resistant clones are subjected to the subsequent analysis.

[C.2] Selection of Drug Resistant Clones Via PCR Analysis

PCR is performed to confirm whether or not IGK-NAC is transferred into the CHO (hprt−/−) cell line retaining the modified human chromosome 14 and whether or not the modified human chromosome 14 is retained. The primers used are shown below.

Primers for Confirmation of IGK-NAC

KJneo (described above)
  PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers for Confirmation of FRT Insertion Site on IGK-NAC:

kD9 tcLa L (described above)
  kD9 tcLa R (described above)
  kD9 tcRa L (described above)
  kD9 tcRa R (described above)

PCR is performed using the primers shown above, KOD FX (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 5 minutes.

Primers for Confirmation of Human Chromosome 2 Region:

D2S177 F (described above)
  D2S177 R (described above)
  EIF2AK3-F (described above)
  EIF2AK3-R (described above)
  RPIA-F (described above)
  RPIA-R (described above)
  IGKC-F (described above)
  IGKC-R (described above)
  IGKV-F (described above)
  IGKV-R (described above)
  Vk3-2 F (described above)
  Vk3-2 R (described above)

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

```
Primers for confirmation of FRT sequence
on modified human chromosome 14:
14TarC_La F:
                                      (SEQ ID NO: 72)
5'-AGCAATTAGGGCCTGTGCATCTCACTTT-3'

14TarC_La R:
                                      (SEQ ID NO: 73)
5'-CCAGCTCATTCCTCCCACTCATGATCTA-3'

14TarC_Ra F:
                                      (SEQ ID NO: 74)
5'-CATCTGGAGTCCTATTGACATCGCCAGT-3'

14TarC_Ra R:
                                      (SEQ ID NO: 75)
5'-CTTATTCCTCCTTCTGCCCACCCTTCAT-3'
```

PCR is performed using the primers shown above, KOD FX (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 6 minutes.

```
Primers for confirmation of human
chromosome 14 region:
MTA1-F3:
                                      (SEQ ID NO: 76)
5'-AGCACTTTACGCATCCCAGCATGT-3'

MTA1-R3:
                                      (SEQ ID NO: 77)
5'-CCAAGAGAGTAGTCGTGCCCCTCA-3'

ELK2P2-F:
                                      (SEQ ID NO: 78)
5'-CCCACTTTACCGTGCTCATT-3'

ELK2P2-R:
                                      (SEQ ID NO: 79)
5'-ATGAAGGTCCGTGACTTTGG-3' g1(g2)-F:
                                      (SEQ ID NO: 80)
5'-ACCCCAAAGGCCAAACTCTCCACTC-3' g1(g2)-R:
                                      (SEQ ID NO: 81)
5'-CACTTGTACTCCTTGCCATTCAGC-3'

VH3-F:
                                      (SEQ ID NO: 82)
5'-AGTGAGATAAGCAGTGGATG-3'

VH3-R:
                                      (SEQ ID NO: 83)
5'-CTTGTGCTACTCCCATCACT-3'

CH3F3:
                                      (SEQ ID NO: 84)
5'-AGGCCAGCATCTGCGAGGAT-3'

CH4R2:
                                      (SEQ ID NO: 85)
5'-GTGGCAGCAAGTAGACATCG-3'
```

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. PCR-positive clones were subjected to the subsequent analysis.

[C.3] Two-Color FISH Analysis

The selected clones are subjected to FISH analysis using human cot-1 DNA and mouse cot-1 DNA as probes to confirm that a copy of IGK-NAC is maintained independently of a copy of the modified human chromosome 14 therein. The clones are then subjected to the subsequent steps.

[D] Construction of IGHK-NAC Using FRT/Flp Recombination System

IGK-NAC and the modified human chromosome 14 are subjected to reciprocal translocation using the FRT/Flp system to clone the IGH region derived from human chromosome 14 into IGK-NAC via translocation. Thus, IGHK-NAC is constructed.

[D.1] Obtaining HAT Resistant Chromosome Recombinant Via FLP Expression

The FRT site on IGK-NAC and the FRT site on the modified human chromosome 14 are subjected to reciprocal translocation in the presence of FLP recombinase. When recombination occurs, 5' HPRT is ligated to 3' HPRT on IGHK-NAC, thereby resulting in reconstitution of the HPRT gene, and HAT resistance is acquired. When CHO (hprt−/−) cells retaining IGK-NAC and modified human chromosome 14 reach confluency in 10-cm cell culture dishes, 18 μg of an FLP expression plasmid is added using Lipofectamine 2000 (Thermo Fisher Scientific) with reference to the manufacturer's instructions. The culture medium is exchanged with the fresh medium 6 hours after the addition, the cells are seeded in ten 10-cm cell culture dishes 24 hours later, and drug selection is then performed using 1×HAT and 6 μg/ml blasticidin. The resulting HAT resistant clones are subjected to the subsequent analysis.

[D.2] Selection of Drug Resistant Clones Via PCR Analysis

In order to confirm that reciprocal translocation using the FRT/FLP system occurs as expected and that IGHK-NAC is constructed, PCR analysis is performed using DNAs extracted from the drug resistant clones as templates. The primers are shown below.

Primers for Confirmation of Site of Ligation by Reciprocal Translocation:

```
TRANS L1 (described above)

TRANS R1 (described above)

CMVr-1:
                                      (SEQ ID NO: 86)
5'-CCTATTGGCGTTACTATGGGAACATACG-3'
```

PGKr-2 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers for Confirmation of Human Chromosome 2 Region:
D2S177 F (described above)
D2S177 R (described above)
IF2AK3-F (described above)

EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. PCR-positive clones are subjected to the subsequent analysis.

[D.3] Two-Color FISH Analysis

The selected clones were subjected to FISH analysis using human cot-1 DNA and mouse cot-1 DNA as probes. If the length of the chromosome 14, as a by-product, which is not to be introduced into NAC, is increased as a result of translocation of an excessive chromosome 2 region, then it is suggested that reciprocal translocation occurs. In addition, two-color FISH analysis is further performed using a combination of BAC clones CH17-405H5 (IGK region: CHORI) and CH17-262H11 (IGH region: CHORI) and a combination of BAC clones CH17-216K2 (IGK region: CHORI) and CH17-212P11 (IGH region: CHORI) as probes to thoroughly analyze whether or not IGHK-NAC is actually constructed. Clones confirmed to comprise one copy of a chromosome presumed to be IGHK-NAC and independently existing therein are used in the subsequent procedure.

[E] Transfer of IGHK-NAC into CHO K1 Cell Line

Both of IGHK-NAC and a by-product formed upon reciprocal translocation to construct the IGHK-NAC comprise a Neo resistant gene incorporated therein. When IGHK-NAC and the by-product are transferred into the target cell by microcell fusion, a cell into which IGHK-NAC and/or the by-product has/have been transferred could be obtained by drug selection with G418. Because NAC comprises EGFP incorporated therein, whether or not IGHK-NAC is transferred into cells of interest could be confirmed; however, in order to prepare a donor cell capable of efficient chromosome transfer and retaining IGHK-NAC alone, the IGHK-NAC is transferred into the CHO K1 cell line.

[E.1] Microcell Fusion and Isolation of Drug Resistant Clone

A cell line retaining IGHK-NAC alone is prepared by chromosome transfer.

The donor cell (CHO IGHK-NAC) is cultured to reach confluency in cell culture dishes, the medium is exchanged with F12 medium supplemented with 20% FBS and 0.1 µg/ml colcemid, culture is performed for additional 48 hours, the medium is exchanged with a fresh F12 medium supplemented with 20% FBS and 0.1 µg/ml colcemid, and incubation is performed overnight to form microcells. The culture medium is removed, the centrifuge flask is filled with a cytochalasin B (10 µg/ml, Sigma) solution kept warm at 37° C. in advance, and centrifugation is then performed at 34° C. and 8,000 rpm for 1 hour. Microcells are suspended in serum-free DMEM and purified using 8-µm, 5-µm, and 3-µm filters. After purification, the microcells are suspended in 2 ml of 0.05 mg/ml PHA-P (Sigma) solution in DMEM, and then added to CHO K1 cells, as recipient cells, which have been cultured to reach confluency in 6-cm cell culture dishes, following removal of culture medium. Incubation is performed for 15 minutes, and the microcells are then allowed to adhere to CHO cells. Thereafter, cell fusion is performed exactly for 1 minute with 1 ml of a PEG1000 (Wako) solution (prepared by completely dissolving 5 g PEG1000 in 6 ml serum-free DMEM and then adding 1 ml dimethyl sulfoxide, followed by sterilization via filtration). The cells are washed with 5 ml serum-free DMEM 4 times to remove PEG, and the CHO culture solution is then added. The cells are seeded in ten 10-cm cell culture dishes 24 hours later, 800 µg/ml G418 is added, and selection culture is then conducted for 10 days. The resulting drug resistant cells in which expression of GFP fluorescent protein is observed on IGHK-NAC are subjected to the subsequent analysis.

[E.2] Selection of Drug Resistant Clone Via PCR Analysis

In order to confirm that IGHK-NAC has been transferred into the CHO K1 cell line, DNAs of the drug resistant clones are extracted and used as templates to perform PCR analysis. The primers are shown below.

Primers for Confirmation of a Site of Ligation by Reciprocal Translocation:
TRANS L1 (described above)
TRANS R1 (described above)
CMVr-1 (described above)
PGKr-2 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers for Confirmation of Human Chromosome 2 Region:
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

Primers for confirmation of human chromosome 14 region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. Clones presumed to retain IGHK-NAC alone as a result of PCR are subjected to the subsequent analysis.

[E.3] Two-Color FISH Analysis

The selected clone is subjected to FISH analysis using human cot-1 DNA and mouse cot-1 DNA as probes to confirm that the clone retains IGHK-NAC alone as expected. In addition, two-color FISH analysis is further performed using a combination of BAC clones CH17-405H5 (IGK region: CHORI) and CH17-262H11 (IGH region: CHORI) and a combination of BAC clones CH17-216K2 (IGK region: CHORI) and CH17-212P11 (IGH region: CHORI) as probes in order to thoroughly analyze whether or not IGHK-NAC is actually constructed.

[F] Transfer of IGHK-NAC into Mouse ES Cell

In order to produce human antibody-producing mice, it is necessary to transfer IGHK-NAC into mouse ES cells, inject the resulting cells into an 8-cell-stage fertilized egg, prepare chimeric mice, and allow IGHK-NAC to be transmitted to progeny. Mouse ES cells retaining IGHK-NAC are prepared.

[F.1] Microcell Fusion and Isolation of Drug Resistant Clone

CHO K1 IGHK-NAC cells, as donor cells, are cultured to reach confluency in cell culture dishes, the medium is exchanged with a F12 medium supplemented with 20% FBS and 0.1 μg/ml colcemid, culture is performed for additional 48 hours, the medium is exchanged with a fresh F12 medium supplemented with 20% FBS and 0.1 g/ml colcemid, and incubation is performed overnight to form microcells. The culture medium is removed, the centrifuge flask is filled with a cytochalasin B (10 μg/ml, Sigma) solution kept warm at 37° C. in advance, and centrifugation is then performed at 34° C. and 8,000 rpm for 1 hour. Microcells are suspended in serum-free DMEM and purified using 8-μm, 5-μm, and 3-μm filters. After purification, the microcells are centrifuged at 2,000 rpm for 10 minutes and then suspended in 5 ml of serum-free DMEM. The resulting suspension is subjected to centrifugation at 2,000 rpm for an additional 10 minutes. As recipient cells, the mouse ES cell lines HKD31 6TG-9 (in which the mouse Igh and Igk genes have been disrupted; disclosed in WO 98/37757) and XO ES9 (in which the antibody gene has not been disrupted) are used. Culture is conducted in DMEM (Dulbecco's Modified Eagle's Medium-high glucose: SIGMA) supplemented with 10% FCS, LIF (Murine Leukemia Inhibitory Factor), $1 \times 10^{-5}$ M 2-ME (2-mercaptoethanol: SIGMA), L-glutamine (3.5 g/ml: GIBCO), a sodium pyruvate solution (3.5 g/ml: GIBCO), and MEM non-essential amino acid (0.125 mM: GIBCO) in the presence of 5% $CO_2$ at 37° C. The surface of the mouse ES cells that have reached confluency in 10-cm cell culture dishes is washed twice with PBS(−). Thereafter, the cells are dispersed by trypsin treatment, recovered in a DMEM supplemented with 10% FBS, and centrifuged at 1,500 rpm. The supernatant is removed therefrom, the cells are resuspended in 5 ml of the serum-free culture solution, and the cell suspension is gently added to a serum-free medium containing the microcell pellet after centrifugation, followed by centrifugation at 1,200 rpm. The supernatant is removed, and cell fusion is performed exactly for 1 minute and 30 seconds with 0.5 ml of a PEG1000 (Wako) solution (prepared by completely dissolving 5 g PEG1000 in serum-free DMEM and then adding 1 ml dimethyl sulfoxide, followed by sterilization via filtration). The serum-free culture solution (DMEM) (13 ml) is gently added thereto, and centrifugation is then conducted at 1,200 rpm. The supernatant is removed, a general culture solution for mouse ES cell is added, and mitomycin-treated G418-resistant mouse embryonic fibroblasts are seeded as feeder cells in two 10-cm cell culture dishes, followed by incubation overnight. G418 is added at a concentration of 250 μg/ml and subjected to selection culture for 3 to 4 weeks. Drug-resistant and EGFP-positive clones are subjected to the subsequent analysis.

[F.2] Selection of Drug Resistant Clones Via PCR Analysis

In order to confirm that IGHK-NAC has been transferred into the mouse ES cell line, DNAs of the drug resistant clones are extracted and used as templates to perform PCR analysis. The primers are shown below.

Primers for Confirmation of a Site of Ligation by Reciprocal Translocation:
TRANS L1 (described above)
TRANS R1 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers for Confirmation of Human Chromosome 2 Region:
EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

Primers for Confirmation of Human Chromosome 14 Region:

MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. Clones presumed to retain IGHK-NAC alone as a result of PCR are subjected to the subsequent analysis.

[F.3] Two-Color FISH Analysis

FISH analysis is performed using human cot-1 DNA and mouse cot-1 DNA as probes to confirm that the clones independently retained IGHK-NAC and maintained the normal host karyotype. Clones exhibiting the results as expected are subjected to preparation of chimeric mice.

[G] Transfer of IGHK-NAC into Rat ES Cell

In order to produce human antibody-producing rats, it is necessary to transfer IGHK-NAC into rat ES cells, inject the resulting cells into 8-cell-stage fertilized eggs, prepare chimeric rats, and allow IGHK-NAC to be transmitted to progeny.

[G.1] Microcell Fusion and Isolation of Drug Resistant Clone

As donor cells, CHO K1 IGHK-NAC is used. IGHK-NAC is introduced into rat ES cells by the technique as with microcell fusion into mouse ES cells as described in F.1 above. Following cell fusion, the cells are incubated overnight, G418 is added to 150 µg/ml, and selection culture is conducted for 3 to 4 weeks. Drug-resistant and EGFP-positive clones are selected and subjected to the subsequent analysis.

[G.2] Selection of Drug Resistant Clones Via PCR Analysis

In order to confirm that IGHK-NAC had been transferred into the rat ES cell line, DNAs of the drug resistant clones are extracted and used as templates to perform PCR analysis. The primers are shown below.

Primers for Confirmation of Site of Ligation by Reciprocal Translocation:

TRANS L1 (described above)
TRANS R1 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers for Confirmation of Human Chromosome 2 Region:

EIF2AK3-F (described above)
EIF2AK3-R (described above)
RPIA-F (described above)
RPIA-R (described above)
IGKC-F (described above)
IGKC-R (described above)
IGKV-F (described above)
IGKV-R (described above)
Vk3-2 F (described above)
Vk3-2 R (described above)

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

Primers for Confirmation of Human Chromosome 14 Region:

MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. Clones presumed to retain IGHK-NAC as a result of PCR are subjected to the subsequent analysis.

[G.3] Two-Color FISH Analysis

FISH analysis is performed using human cot-1 DNA and mouse cot-1 DNA as probes to confirm that the clones independently retained IGHK-NAC and maintained the normal rat ES karyotype (42 chromosomes) as expected. Such clones are subjected to preparation of chimeric rats.

[H] Preparation of Mice Retaining IGHK-NAC

Mice retaining IGHK-NAC are prepared and analyzed. Chimeric mice obtained during the process are also analyzed.

[H.1] Preparation of Chimeric Mice

Using the mouse ES cells retaining IGHK-NAC, chimeric mice are prepared in accordance with the techniques described in Gene Targeting, Experimental Medicine, 1995. As host cells, the morula obtained by sexual crossbreeding of MCH (ICR) (white, purchased from CLEA Japan, Inc.) and the 8-cell-stage embryo are used. Whether or not the newborn mice obtained though transplantation of the injected embryo into a foster mother are chimeric mice could be determined based on the coat color.

[H.2] Analysis of Retention of IGHK-NAC on Chimeric Mice

The tails are obtained from 3-week-old or older chimeric mice in accordance with the method described in Motoya Katsuki, Developmental Engineering Experimentation Manual, Kodansha Scientific, 1987, and genomic DNAs are extracted using the Puregene DNA Isolation Kit (Qiagen). PCR analysis is performed using the primers and the PCR conditions as described in G.2 above to confirm the retention of IGHK-NAC.

After blood samples are obtained from the chimeric mice, in addition, blood cells are fixed to prepare specimens, and FISH analysis is performed using Human Cot-1 and Mouse minor satellite DNAs as probes. Thus, the cells retaining IGHK-NAC are identified at the chromosome level.

[H.3] Evaluation of Human IGM Expression in Chimeric Mice Derived from ES Cells Retaining IGHK-NAC In HKD31 mouse ES cells, the mouse Igh and Igk genes had been disrupted. A mouse in which the antibody μ chain gene necessary for generation of B lymphocytes had been knocked out is lack of mature B lymphocytes taking a role in the humoral immunity, and such mouse is thus incapable of antibody production. Accordingly, the HKD31 mouse ES cells could not serve as mature B cells in chimeric mice. Concerning HKD31 mouse cells retaining IGHK-NAC used for chimeric mice preparation, such problem could be resolved if human IGM is expressed from IGHK-NAC. Thus, GFP-positive B cells could be detected, and the functional expression of the IGM gene on the IGHK-NAC could be proved indirectly. Blood samples are obtained from the chimeric mice, and the samples are stained with an antibody to mouse CD45R (B220) to detect mouse B cells using a flow cytometer. By analyzing whether or not the cells are co-positive for CD45R and GFP, functional expression of the IGHK-NAC-derived IGM is confirmed. Blood cells are stained with an antibody to human IGM and mouse CD45R (B220) to confirm human IGM-, CD45R-, and GFP-positive cells. Peripheral blood is obtained, transferred into a tube containing heparin PBS, and subjected to inversion mixing, followed by ice cooling. After the blood sample is centrifuged at 2,000 rpm and 4° C. for 3 minutes, the supernatant is removed, various antibodies are added, the reaction is allowed to proceed at 4° C. for 30 minutes, and the resultant is then washed with PBS supplemented with 5% fetal bovine serum (5% FBS/PBS). After the final centrifugation, 1.2% dextran/physiological saline is added to the pellet and, after tapping, the resultant is allowed to stand at room temperature for 45 minutes, so that red blood cells naturally precipitated. Then, the supernatant is transferred to a new tube, centrifugation is performed at 2,000 rpm and 4° C. for 3 minutes, the supernatant is removed, a hemolytic agent (0.17 M $NH_4Cl$) is added to the pellet at room temperature, and the resultant is then allowed to stand for 5 minutes. The cells are centrifuged at 2,000 rpm and 4° C. for 3 minutes, washed with 5% FBS/PBS, and suspended in 500 μl of 5% FBS/PBS. The suspension is designated as an analyte and analyzed by flow cytometry.

[H.4] Detection of Human Antibody in Chimeric Mouse Serum

In order to confirm the expression of the human antibody gene light chain, the human antibody gene heavy chain, and various isotypes in chimeric mice, the human antibody concentration in the blood serum is determined by the enzyme linked immunosorbent assay (ELISA). ELISA is performed in accordance with the method described in the following documents: Experimental Manual for Monoclonal Antibody, Toyama and Ando, Kodansha, 1987; Introduction of Experiment for Monoclonal Antibody, Ando and Chiba, Kodansha, 1991; Ultrasensitive Enzyme Immunoassays, Ishikawa, Gakkai Shuppan Center, 1993; Ed Harlow and David Lane, Antibodies: A Laboratory Manual, Cold Spring Harbor Laboratory, 1988; and A. Doyle and J. B. Griffiths, Cell & Tissue Culture: Laboratory Procedures, John Wiley & Sons Ltd., 1996. With reference to the methods described in these documents, the reaction time and temperature are improved so that they would be performed, for example, at 4° C. overnight, depending on assay systems. A certain type of antibody is detected using a kit. Expression of human antibodies (hγ, hμ, hκ, hγ1, hγ2, hγ3, hγ4, hα, hε, and hδ) and concentration thereof in serum are determined. Basic procedures are described below.

An antibody to a human immunoglobulin to be measured is diluted and an ELISA plate is coated therewith at 4° C. overnight. In assay of serum samples, PBS supplemented with 5% fetal bovine serum is used for blocking and dilution of samples and label antibodies. After the coated plate is washed, blocking is conducted for at least 1 hour. After the plate is washed, the sample is added, and incubation is performed for at least 30 minutes. After washing the plate, a diluted enzyme-labeled anti-human immunoglobulin antibody and a diluted mouse immunoglobulin antibody are added, incubation is performed for at least 1 hour, the plate is washed, and a substrate solution is added to develop color. An assay is basically performed in accordance with the same procedures. That is, assay is performed using a biotin-labeled antibody, washing the plate, adding an avidin-enzyme complex, conducting incubation, washing the plate, and then adding a substrate solution. The absorbance is measured using a microplate reader. When the serum concentration is to be assayed, the standard with known concentration is serially diluted to conduct ELISA simultaneously with sample assays, and analysis is conducted using a calibration curve to determine the concentration.

[H.5] Expression Analysis and Sequencing of Human Antibody cDNA is synthesized from RNA derived from a chimeric rat spleen, and cloning and nucleotide sequencing of a human antibody gene variable region are performed in accordance with the method disclosed in WO 98/37757. Thus, human antibody expression is analyzed and evaluated.

[H.6] Evaluation of Response for Antigen-Specific Human Antibody Production

A chimeric mouse is evaluated as to an increase in the antigen-specific human antibody titer. In accordance with the method disclosed in the patent literature (WO 98/37757), the chimeric mouse is immunized with human serum albumin to analyze an increase in the antibody titer.

[I] Transmission of IGHK-NAC from IGHK-NAC-Retaining Chimeric Mice to Progeny

[I.1] Transmission of IGHK-NAC to Progeny

The female chimeric mice produced in [H] above (chimeric rate: approximately 100%) are subjected to crossbreeding with male ICR mice, and the newborn mice are subjected to observation of GFP fluorescence indicating a dominant inheritance of ES cell-derived IGHK-NAC. When the GFP fluorescence is observed, the transmission of IGHK-NAC to progeny and the stable retention thereof in the mice could be confirmed. A mouse lineage that had inherited IGHK-NAC is called "mTC (IGHK-NAC)."

[I.2] Confirmation of Retention of IGHK-NAC in IGHK-NAC-Retaining Mice

By analyzing the mTC (IGHK-NAC) in the same manner as in Example 7 [H.2], transmission of IGHK-NAC to progeny is confirmed in detail.

[I.3] Evaluation of Human Antibody-Producing Capacity of IGHK-NAC-Retaining Mice The mTC (IGHK-NAC) is evaluated in the same manner as in Example 7 [H.4], [H.5], and [H.6].

[J] Preparation of IGHK-NAC-Retaining Rat

Rats retaining IGHK-NAC are prepared and analyzed. Chimeric mice obtained during the process are also analyzed.

[J.1] Preparation of Chimeric Rat

Chimeric rats are produced using ES cell clones of the IGHK-NAC-retaining rats obtained in Example 7 [G] in accordance with the method of Hirabayashi et al. (Mol. Reprod. Dev., 2010 February; 77 (2): 94.doi:10. 1002/mrd.21123). As hosts, blastocyst-stage embryos obtained by sexual crossbreeding of Crlj:WI rats (white, purchased from Charles River Laboratories Japan, Inc.) are used. Whether or not the newborn rats obtained though transplantation of the injected embryo into a foster mother are chimeric could be determined based on the coat color. GFP fluorescence indicating a dominant inheritance of ES cell-derived IGHK-NAC is also observed immediately after birth to confirm contribution of ES cells.

[J.2] Confirmation of Retention of IGHK-NAC in Chimeric Rats Derived from IGHK-NAC-Retaining ES Cells Analysis is performed in the same manner as in [H.2] above to confirm the retention of IGHK-NAC more precisely. Blood cells are subjected to FISH analysis using Human Cot-1 and Mouse Cot-1 DNAs as probes.

[J.3] Evaluation of Human Antibody-Producing Capacity of Chimeric Rats

Chimeric rats are evaluated in the same manner as in Example 7 [A.4], [A.5], and [A.6]

[K] Transmission of IGHK-NAC from IGHK-NAC-Retaining Chimeric Rats to Progeny

[K.1] Transmission of IGHK-NAC from IGHK-NAC-Retaining Chimeric Rats to Progeny

The chimeric rat produced in [J] above (chimeric rate: approximately 100%) is subjected to crossbreeding with a Crlj:WI rat, and the newborn rat is subjected to observation of GFP fluorescence indicating a dominant inheritance of IGHK-NAC derived from ES cells. Because GFP fluorescence is observed, the transmission of IGHK-NAC and the stable retention thereof therein are confirmed in the rat individuals. A rat lineage that had inherited IGHK-NAC is called "rTC (IGHK-NAC)."

[K.2] Confirmation of Retention of IGHK-NAC in IGHK-NAC-Retaining Rats rTC (IGHK-NAC) is analyzed in the same manner as in [J.2] above, so that the transmission of IGHK-MAC to the progeny is confirmed in detail.

[K.3] Evaluation of Human Antibody-Producing Capacity of IGHK-NAC-Retaining Rats rTC (IGHK-NAC) is evaluated in the same manner as in Example 7 [H.4], [H.5], and [H.6].

[Example 8] Preparation of Human Antibody-Producing Mice and Rats Using Novel Mouse Artificial Chromosome Vectors (IGHL-NAC)

The human antibody genes (IGH and IGL) were introduced into NAC to construct IGHL-NAC, and human antibody-producing mice and rats retaining IGHL-NAC were prepared (FIG. 21).

[A] Transfer of Modified Human Chromosome 22 into CHO Cells Retaining NAC

Modified human chromosome 22 is transferred from a CHO cell retaining modified human chromosome 22 into a CHO cell retaining NAC.

[A.1] Transfer of Modified Human Chromosome 22 into Hprt-Deficient CHO Cell Retaining NAC Via Microcell Fusion CHO cells retaining the modified human chromosome 22 (CHO hChr22LF) as donor cells are cultured in cell culture dishes. When the culture reaches confluency, the medium is exchanged with F12 medium supplemented with 20% FBS and 0.1 µg/ml colcemid, culture is performed for an additional 48 hours, the medium is exchanged with a fresh F12 medium supplemented with 20% FBS and 0.1 µg/ml colcemid, and incubation is performed overnight to form microcells. The culture medium is removed, the centrifuge flask is filled with a cytochalasin B (10 µg/ml, Sigma) solution kept warm at 37° C. in advance, and centrifugation is then performed at 34° C. and 8,000 rpm for 1 hour. Microcells are suspended in serum-free DMEM and purified using 8-µm, 5-µm, and 3-µm filters. After purification, the microcells are suspended in 2 ml of 0.05 mg/ml PHA-P (Sigma) solution in DMEM, and then added to NAC-retaining Hprt-deficient CHO cells, as recipient cells, which had been cultured to reach confluency in 6-cm cell culture dishes, following removal of culture medium. Incubation is performed for 15 minutes, and the microcells are then allowed to adhere to CHO cells. Thereafter, cell fusion is performed exactly for 1 minute with 1 ml of a PEG1000 (Wako) solution (prepared by completely dissolving 5 g of PEG1000 in 6 ml of the serum-free DMEM and adding 1 ml of dimethyl sulfoxide thereto, followed by sterilization via filtration). Washing is performed 4 times with 5 ml of serum-free DMEM to remove PEG, and the CHO culture solution is then added. The cells are seeded in ten 10-cm cell culture dishes 24 hours later, 8 µg/ml blasticidin S is added, and selection culture is then conducted for 10 days. The resulting drug resistant cells are subjected to the subsequent analysis.

[A.2] Selection of Drug Resistant Clones Via PCR Analysis

PCR is performed using the genomic DNA extracted from the blasticidin S resistant clone as a template to examine the retention of the modified human chromosome 2. The primer sequences are shown below.

```
Primers for confirmation of loxP sequence
on modified human chromosome 22:
22CeT La L:
                                    (SEQ ID NO: 87)
5'-CCTGCCTTCTTGTTTCAGCTCTCAACTG-3'

22CeT La R:
                                    (SEQ ID NO: 88)
5'-GACGTGCTACTTCCATTTGTCACGTCCT-3'

22CeT Ra L:
                                    (SEQ ID NO: 89)
5'-ATCCCCATGTGTATCACTGGCAAACTGT-3'

22CeT Ra R:
                                    (SEQ ID NO: 90)
5'-ACACTTTAGTCCCTGTCCCCTCAACGAG-3'
```

PCR is performed using TP600 thermal cycler (Takara), KOD FX enzyme (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 5 minutes.

```
Primers for confirmation of FRT sequence
on modified human chromosome 22:
22TeT La L:
                                    (SEQ ID NO: 91)
5'-TGCAGGTATCTGTTGGTGTCCCTGTTTT-3'

22TeT La R:
                                    (SEQ ID NO: 92)
5'-GACGTGCTACTTCCATTTGTCACGTCCT-3'
```

22TeT Ra L:
(SEQ ID NO: 93)
5'-AGCAGAGCTCGTTTAGTGAACCGTCAGA-3'

22TeT Ra R:
(SEQ ID NO: 94)
5'-CTGTCCTATCCTTGCAGCTGTCTTCCAG-3'

PCR is performed using TP600 thermal cycler (Takara), KOD FX enzyme (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 5 minutes. Thus, recombination is confirmed.

In addition, whether or not the region of interest on human chromosome 2 is retained is confirmed using primers. The primer sequences are shown below.

553P-F:
(SEQ ID NO: 95)
5'-AGATCTCTTGAGCCCAGCAGTTTGA-3'

553P-R:
(SEQ ID NO: 96)
5'-TGAAGTTAGCCGGGGATACAGACG-3'

PPMIF L:
(SEQ ID NO: 97)
5'-AACGGCAGCCAAACCAAAGA-3'

PPMIF R:
(SEQ ID NO: 98)
5'-ACCAGGACTGGCTGGGCATA-3'

IGLVI-70 L:
(SEQ ID NO: 99)
5'-AGTCTGCGCTGACCCAGGAA-3'

IGLVI-70 R:
(SEQ ID NO: 100)
5'-TTGAGCCAGAGAAGCGGTCA-3'

GNAZ L:
(SEQ ID NO: 101)
5'-TCCACTTGGGGGTCTGCATT-3'

GNAZ R:
(SEQ ID NO: 102)
5'-TGGTGCTGAGCAGCTGTGTG-3'

LIF L:
(SEQ ID NO: 103)
5'-TGGGACTTAGGTGGGCCAGA-3'

LIF R:
(SEQ ID NO: 104)
5'-GCCTCCCCAAGAGCCTGAAT-3' hVpreB1-F:
(SEQ ID NO: 105)
5'-TGTCCTGGGCTCCTGTCCTGCTCAT-3' hVpreB1-Rm:
(SEQ ID NO: 106)
5'-GGCGGCGACTCCACCCTCTT-3' hVpreB3-F:
(SEQ ID NO: 107)
5'-CACTGCCTGCCCGCTGCTGGTA-3' hVpreB3-R:
(SEQ ID NO: 108)
5'-GGGCGGGAAGTGGGGAGAG-3' hL5-F:
(SEQ ID NO: 109)
5'-AGCCCCAAGAACCCAGCCGATGTGA-3' hL5-R:
(SEQ ID NO: 110)
5'-GGCAGAGGGAGTGTGGGGTGTTGTG-3'

344-F:
(SEQ ID NO: 111)
5'-ATCATCTGCTCGCTCTCTCC-3'

344-R:
(SEQ ID NO: 112)
5'-CACATCTGTAGTGGCTGTGG-3'

350P-F:
(SEQ ID NO: 113)
5'-ACCAGCGCGTCATCATCAAG-3'

350P-R:
(SEQ ID NO: 114)
5'-ATCGCCAGCCTCACCATTTC-3'

IgL-F:
(SEQ ID NO: 115)
5'-GGAGACCACCAAACCCTCCAAA-3'

IgL-Rm:
(SEQ ID NO: 116)
5'-GAGAGTTGGAGAAGGGGTGACT-3'

SERPIND1 L:
(SEQ ID NO: 117)
5'-ACCTAGAGGGTCTCACCTCC-3'

SERPIND1 R:
(SEQ ID NO: 118)
5'-CCCTGGACATCAAGAATGG-3'

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute.

PCR-positive clones are subjected to the subsequent analysis.

[A.3] Two-Color FISH Analysis

PCR-positive clones are subjected to FISH analysis using human cot-1 DNA and mouse cot-1 DNA as probes to select positive cells retaining NAC independently of the modified human chromosome 22.

Figure 22:
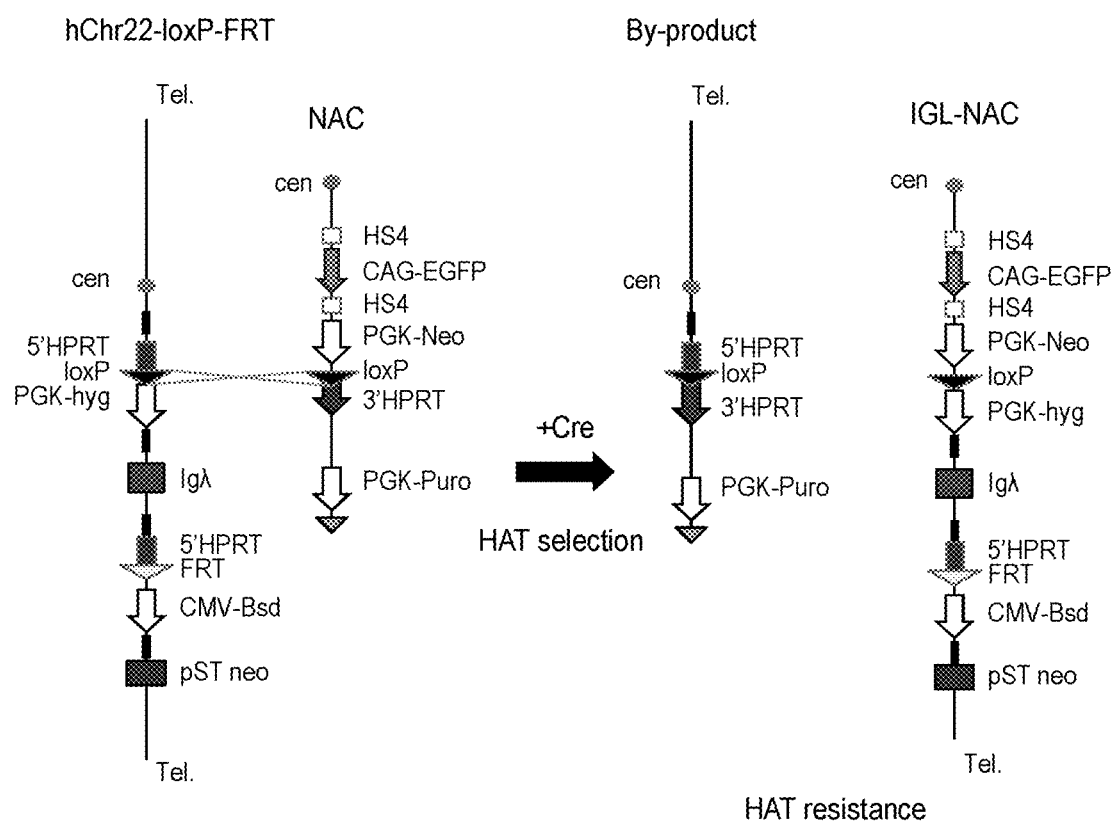
FIG. 22 schematically shows construction of IGL-NAC via reciprocal translocation caused by the Cre/loxP system. Concerning HAT resistance, when recombination takes place in the loxP sequence, 5' HPRT is ligated to 3' HPRT, the HPRT gene is reconstructed, HAT resistance is acquired, and selection can be thus made with the aid of HAT. In the figure, Igκ represents the immunoglobulin light chain λ gene (or gene locus), Cen. represents a centromere, Tel. represents a telomere, HS4 represents an insulator, CAG, CMV, and PGK each represent a promoter, EGFP represents a gene encoding a fluorescent protein, Bsd, hyg, Puro, and Neo each represent a drug resistant gene, and HPRT represents a hypoxanthine-guanine phosphoribosyltransferase gene.

[B] Introduction of Human Chromosome 22 IGL Region into Mouse Artificial Chromosome Vector (NAC) Via Translocation Cloning In the CHO cells retaining NAC, the IGL region of the human chromosome 22 was introduced into NAC via translocation cloning. In translocation cloning, the human chromosome 2 and NAC were subjected to reciprocal translocation using the Cre/loxP system, so as to introduce the IGL region into NAC (FIG. 22).

[B.1] Acquisition of HAT Resistant Chromosome Recombinant Via Cre Expression

NAC comprises a loxP site introduced thereinto, which would undergo recombination with the loxP site of the modified human chromosome 2 in the presence of Cre recombinase. When recombination took place, a by-product; i.e., 5' HPRT in the human chromosome 2 region that would not be introduced into NAC, would be ligated to a by-product; i.e., 3' HPRT at the NAC terminus, the HPRT gene would be reconstructed, and CHO(hprt-/-) would acquire HAT resistance.

When the Hprt-deficient CHO cells retaining modified human chromosome 2 and NAC reaches confluency in a 10-cm cell culture dish, 18 μg of a Cre expression plasmid (vector name: pBS185) is added using Lipofectamine 2000 (Thermo Fisher Scientific) with reference to the manufacturer's instructions. The culture solution is exchanged with a fresh culture solution 6 hours after the addition, the cells are seeded in ten 10-cm cell culture dishes 24 hours later, and drug selection is then performed using 1×HAT (Sigma) and 4 μg/ml blasticidin. The drug resistant clones obtained are subjected to the subsequent analysis.

[B.2] Selection of Drug Resistant Clones Via PCR Analysis

PCR is performed using genomic DNAs extracted from HAT resistant cells as templates and the primers shown below to select clones resulting from reciprocal translocation, and whether or not reciprocal translocation had occurred between the human chromosome 2 fragment and NAC is examined. The primer sequences are shown below.
TRANS L1 (described above)
TRANS R1 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers used to confirm whether or not the FRT insertion site is maintained are shown below:
22TeT La L (described above)
22TeT La R (described above)
22TeT Ra L (described above)
22TeT Ra R (described above)

PCR is performed using TP600 thermal cycler (Takara), KOD FX enzyme (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 5 minutes.

The human chromosome 22 region is subjected to PCR analysis. The sequences are shown below:
553P-F (described above)
553P-R (described above)
PPM1F L (described above)
PPM1F R (described above)
IGLVI-70 L (described above)
IGLVI-70 R (described above)
GNAZ L (described above)
GNAZ R (described above)
LIF L (described above)
LIF R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)
SERPIND1 L (described above)
SERPIND1 R (described above)

PCR is performed using the primers shown above, AmpliTaq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute.

[B.3] Two-Color FISH Analysis

FISH analysis is performed using human cot-1 DNA and mouse cot-1 DNA as probes to confirm that reciprocal translocation had occurred between NAC and the modified human chromosome 22 and IGL-NAC comprising the IGL region introduced into NAC is retained independently of the by-product. The selected positive clones (designated as "CHO IGL-NAC") are subjected to the subsequent experiment.

[C] Transfer of IGL-NAC into CHO (Hprt−/−) Cell Line Retaining Modified Human Chromosome 14

The prepared IGL-NAC is transferred into the CHO (hprt−/−) cell line retaining the modified human chromosome 14 to introduce the IGH region into IGL-NAC via recombination using the FRT/Flp system. Thus, IGHL-NAC is prepared.

[C.1] Microcell Fusion and Isolation of Drug Resistant Clone

CHO IGL-NAC as donor cells are cultured to reach confluency in a cell culture dish, the medium is exchanged with F12 medium supplemented with 20% FBS and 0.1 μg/ml colcemid, culture is performed for an additional 48 hours, the medium is exchanged with a fresh F12 medium supplemented with 20% FBS and 0.1 μg/ml colcemid, and incubation is performed overnight to form microcells. The culture medium is removed, the centrifuge flask is filled with a cytochalasin B (10 μg/ml, Sigma) solution kept warm at 37° C. in advance, and centrifugation is then performed at 34° C. and 8,000 rpm for 1 hour. Microcells are suspended in serum-free DMEM and purified using 8-μm, 5-μm, and 3-μm filters. After purification, the microcells are suspended in 2 ml of the solution of 0.05 mg/ml PHA-P (Sigma) in DMEM, and then added to Hprt-deficient CHO cell line (disclosed in PCT/JP2017/039441), as a recipient cell, which had been cultured to reach cofluency in 6-cm cell culture dishes, following removal of the culture medium. Incubation is performed for 15 minutes, and the microcells are then allowed to adhere to CHO cells. Thereafter, cell fusion is performed exactly for 1 minute with 1 ml of a PEG1000 (Wako) solution (prepared by completely dissolving 5 g of PEG1000 in 6 ml of the serum-free DMEM and adding 1 ml of dimethyl sulfoxide thereto, followed by sterilization via filtration). Washing is performed 4 times with 5 ml of serum-free DMEM to remove PEG, and the CHO culture solution is then added. The cells are seeded in ten 10-cm cell culture dishes 24 hours later, 600 μg/ml G418 and 6 μg/ml blasticidin are added thereto, and selection culture is then conducted for 10 days. The resulting drug-resistant clones are subjected to the subsequent analysis.

[C.2] Selection of Drug Resistant Clones Via PCR Analysis

PCR is performed to examine whether or not IGL-NAC had been introduced into the CHO (hprt−/−) cell line retaining the modified human chromosome 14 and the modified human chromosome 14 had been maintained. The primers used are shown below.

Primers for Confirmation of IGL-NAC:
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

Primers used to confirm whether or not the FRT insertion site is maintained are shown below:
  22TeT La L (described above)
  22TeT La R (described above)
  22TeT Ra L (described above)
  22TeT Ra R (described above)

PCR is performed using TP600 thermal cycler (Takara), KOD FX enzyme (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles 98° C. for 15 seconds and 68° C. for 5 minutes.

The human chromosome 22 region is subjected to PCR analysis. The primer sequences are shown below:
  553P-F (described above)
  553P-R (described above)
  PPM1F L (described above)
  PPM1F R (described above)
  IGLVI-70 L (described above)
  IGLVI-70 R (described above)
  GNAZ L (described above)
  GNAZ R (described above)
  LIF L (described above)
  LIF R (described above)
  hVpreB1-F (described above)
  hVpreB1-Rm (described above)
  hVpreB3-F (described above)
  hVpreB3-R (described above)
  hL5-F (described above)
  hL5-R (described above)
  344-F (described above)
  344-R (described above)
  350P-F (described above)
  350P-R (described above)
  IgL-F (described above)
  IgL-Rm (described above)
  SERPIND1 L (described above)
  SERPIND1 R (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute.
Primers for Confirmation of Human Chromosome 14 Region:
  MTA1-F3 (described above)
  MTA1-R3 (described above)
  ELK2P2-F (described above)
  ELK2P2-R (described above)
  g1(g2)-F (described above)
  g1(g2)-R (described above)
  VH3-F (described above)
  VH3-R (described above)
  CH3F3 (described above)
  CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute.
Primers for confirmation of FRT insertion site on modified human chromosome 14:
  14TarC_La F (described above)
  14TarC_La R (described above)
  14TarC_Ra F (described above)
  14TarC_Ra R (described above)

PCR is performed using the primers shown above, KOD FX (TOYOBO), and buffers and dNTPs (dATP, dCTP, DGTP, and dTTP) included in the kit under the recommended conditions. Temperature and cycle conditions are as follows: thermal denaturation at 98° C. for 1 minute is followed by 35 cycles of 98° C. for 15 seconds and 68° C. for 6 minutes.

Clones are selected on the basis of the results above and subjected to the subsequent experiment.

[C.3] Two-Color FISH Analysis

The selected clones are subjected to FISH analysis using human cot-1 DNA and mouse cot-1 DNA as probes to identify clones in which a copy of IGL-NAC is maintained independently of a copy of the modified human chromosome 14. The positive cells (designated as "CHO #14 IGL-NAC") are selected and then subjected to the subsequent experiment.

[D] Construction of IGHL-NAC Using FRT/Flp Recombination System

Figure 23:
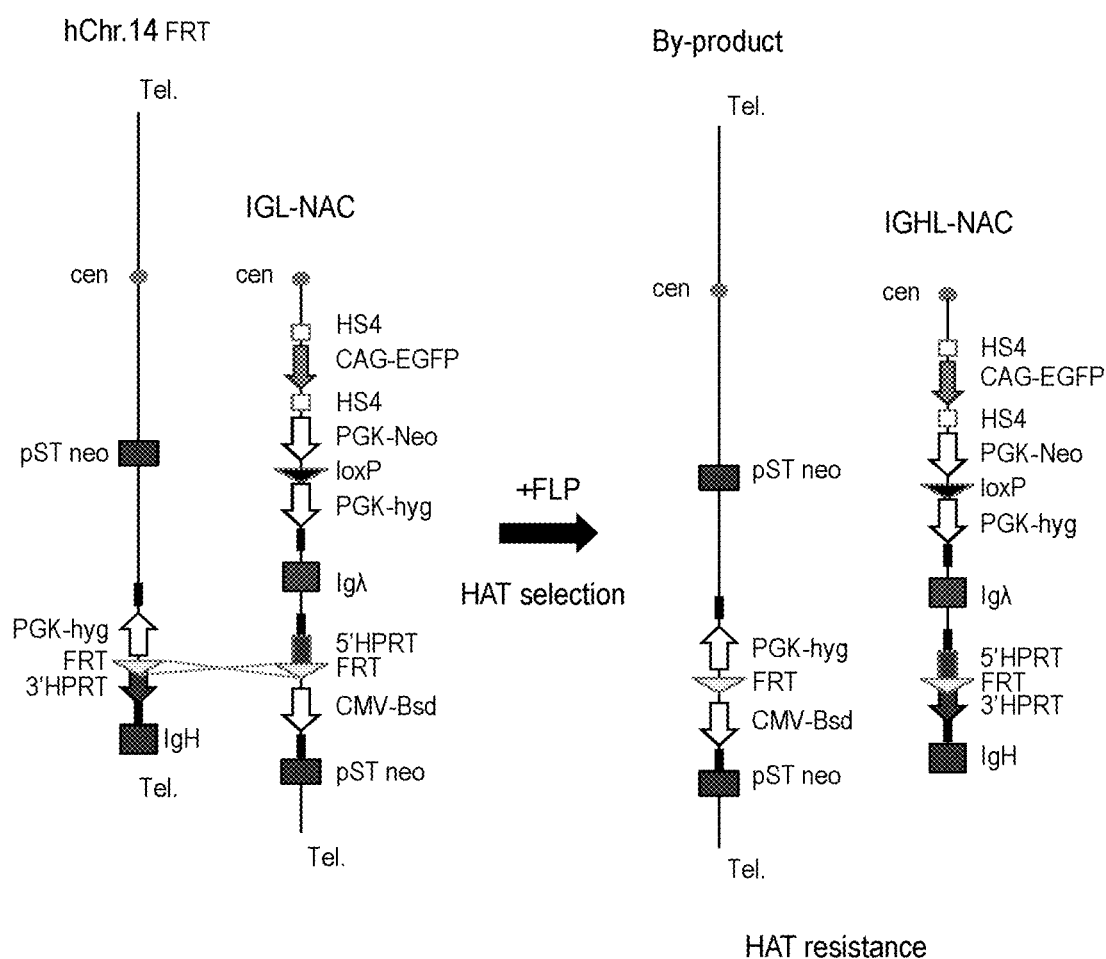
FIG. 23 schematically shows construction of IGHL-NAC via reciprocal translocation caused by the Flp/FRT system. Concerning HAT resistance, when recombination takes place in the FRT sequence, 5' HPRT is ligated to 3' HPRT, the HPRT gene is reconstructed, HAT resistance is acquired, and selection can be thus made with the aid of HAT. In the figure, Cen. represents a centromere, Tel. represents a telomere, HS4 represents an insulator, CAG, CMV, and PGK each represent a promoter, EGFP represents a gene encoding a fluorescent protein, Bsd, hyg, and Neo each represent a drug resistant gene, and HPRT represents a hypoxanthine-guanine phosphoribosyltransferase gene.

IGL-NAC and the modified human chromosome 14 were subjected to reciprocal translocation using the FRT/Flp system to clone the IGH region derived from human chromosome 14 into IGL-NAC via translocation. Thus, IGHL-NAC was constructed (FIG. 23).

[D.1] Obtaining HAT Resistant Chromosome Recombinant Via Cre Expression

The FRT site on IGL-NAC is subjected to reciprocal translocation with the FRT site on the modified human chromosome 14 in the presence of FLPo recombinase. When recombination took place, 5' HPRT is ligated to 3' HPRT on IGHL-NAC, the HPRT gene is reconstructed, and HAT resistance is acquired. When CHO #14IGL-NAC reaches confluency in 10-cm cell culture dishes, 18 μg of an FLP expression plasmid is added using Lipofectamine 2000 (Thermo Fisher Scientific) with reference to the manufacturer's instructions. The culture medium is exchanged with a fresh culture medium 6 hours after the addition, the cells are seeded in ten 10-cm cell culture dishes 24 hours later, and drug selection is then performed using 1×HAT and 8 μg/ml blasticidin.

The resulting HAT resistant clones are subjected to the subsequent analysis.

[D.2] Selection of Drug Resistant Clones Via PCR Analysis

In order to confirm that reciprocal translocation using the FRT/FLP system occurs as expected and IGHK-NAC is constructed, PCR is performed using DNAs extracted from the drug resistant clones as templates. The primers are shown below.
Primers for Confirmation of Site of Ligation by Reciprocal Translocation:
  TRANS L1 (described above)
  TRANS R1 (described above)
  CMVr-1 (described above)

PGKr-2 (described above)
KJneo (described above)
PGKr-2 (described above)
PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

The human chromosome 22 region is subjected to PCR. The primer sequences are shown below:
553P-F (described above)
553P-R (described above)
PPM1F L (described above)
PPM1F R (described above)
IGLVI-70 L (described above)
IGLVI-70 R (described above)
GNAZ L (described above)
GNAZ R (described above)
LIF L (described above)
LIF R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above
IgL-F (described above)
IgL-Rm (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute. Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. Clones are selected based on the PCR results and then subjected to the following experiment.

[D.3] Two-Color FISH Analysis

Two-color FISH analysis is performed using a combination of BAC clones CH17-424L4 (IGL region) and CH17-262H1 (IGH region) and a combination of BAC clones CH17-95F2 (IGL region) and CH17-212P11 (IGH region) as probes in order to thoroughly analyze whether or not IGHL-NAC is actually constructed. Clones in which signals indicating the presence of the IGL region and the IGH region are observed on NAC are designated as positive clones. Thus, construction of IGHL-NAC is confirmed (designated as CHO IGHL-NAC), and the selected clones are subjected to the subsequent experiment.

[E] Transfer of IGHL-NAC into CHO K1 Cell Line

Both of IGHL-NAC and a by-product, which is formed upon reciprocal translocation for constructing IGHL-NAC, comprised a Neo-resistant gene inserted therein. When the IGHL-NAC and the by-product are transferred into the target cells by microcell fusion, a cell into which either or both of IGHL-NAC and the by-product is/are transferred could be obtained by drug selection with G418. Because the NAC comprises EGFP inserted therein, whether or not IGHL-NAC is transferred into a target cell could be confirmed; however, in order to prepare a donor cell capable of efficient chromosome transfer and retaining IGHL-NAC alone, the IGHL-NAC is transferred into the CHO K1 cell line.

[E.1] Microcell Fusion and Isolation of Drug Resistant Clone: Transfer of IGHL-NAC into CHO K1 Cell Line CHO IGHL-NAC cells as donor cells are cultured in cell culture dishes. When the culture reaches confluency, the medium is exchanged with F12 medium supplemented with 20% FBS and 0.1 µg/ml colcemid, culture is performed for an additional 48 hours, the medium is exchanged with a fresh F12 medium supplemented with 20% FBS and 0.1 µg/ml colcemid, and incubation is performed overnight to form microcells. The culture medium is removed, the centrifuge flask is filled with a cytochalasin B (10 µg/ml, Sigma) solution kept warm at 37° C. in advance, and centrifugation is then performed at 34° C. and 8,000 rpm for 1 hour. Microcells are suspended in serum-free DMEM and purified using 8-µm, 5-µm, and 3-µm filters. After purification, the microcells are suspended in 2 ml of 0.05 mg/ml PHA-P (Sigma) solution in DMEM, and then cultured in 6-cm cell culture dishes to reach confluency, followed by removal of the culture medium, and the resultant is then added to the recipient CHO K1 cells. Incubation is performed for 15 minutes, and the microcells are then allowed to adhere to CHO cells. Thereafter, cell fusion is performed exactly for 1 minute with 1 ml of a PEG1000 (Wako) solution (prepared by completely dissolving 5 g of PEG1000 in 6 ml of the serum-free DMEM and adding 1 ml of dimethyl sulfoxide thereto, followed by sterilization via filtration). Washing is performed 4 times with 5 ml of serum-free DMEM to remove PEG, and the CHO culture solution is then added. The cells are seeded in ten 10-cm cell culture dishes 24 hours later, 800 g/ml G418 is added thereto, and selection culture is then conducted for 10 days. The resulting drug-resistant clones are subjected to the subsequent analysis.

[E.2] Selection of Drug Resistant Clones Via PCR Analysis

In order to confirm that IGHL-NAC is transferred into the CHO K1 cell line, PCR analysis is performed using DNAs extracted from the drug resistant clones as templates. The primers are shown below.
Primers for Confirmation of Site of Ligation by Reciprocal Translocation:
TRANS L1 (described above)
TRANS R1 (described above)
CMVr-1 (described above)

PGKr-2 (described above)
KJneo (described above)
PGKr-2 (described above)
PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

The human chromosome 22 region is subjected to PCR. The primer sequences are shown below:
553P-F (described above)
553P-R (described above)
PPM1F L (described above)
PPM1F R (described above)
IGLVI-70 L (described above)
IGLVI-70 R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute. Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. PCR-positive cell lines are subjected to the subsequent analysis.

[E.3] Two-Color FISH Analysis
FISH analysis is performed using human cot-1 DNA and mouse cot-1 DNA as probes to confirm that one copy of IGHL-NAC is independently retained.

In addition, two-color FISH analysis is further performed using a combination of BAC clones CH17-424L4 (IGL region) and CH17-262H11 (IGH region) and a combination of BAC clones CH17-95F2 (IGL region) and CH17-212P11 (IGH region) as probes in order to thoroughly analyze the IGHL-NAC structure. Clones in which signals indicating the presence of the IGL region and the IGH region are observed on NAC are designated as positive clones (designated as CHO K IGHL-NAC) and subjected to the subsequent experiment.

[F] Transfer of IGHL-NAC into Mouse ES Cells
In order to produce human antibody-producing mice, it is necessary to transfer IGHL-NAC into mouse ES cells, inject the resulting cells into an 8-cell-stage fertilized egg, prepare chimeric mice, and allow IGHL-NAC to be transmitted to progeny.

[F.1] Microcell Fusion and Isolation of Drug Resistant Clone
As donor cells, CHO K1 IGHL-NAC is used. Microcell fusion is performed by the technique as used in Example 7 [F.1] to obtain EGFP-positive and drug-resistant cells, and the obtained cells are subjected to the subsequent analysis.

[F.2] Selection of Drug Resistant Clones Via PCR Analysis
In order to confirm that IGHL-NAC had been transferred into mouse ES cells, PCR analysis is performed using DNAs extracted from the drug resistant clones as templates. The primers are shown below.
Primers for Confirmation of Site of Ligation by Reciprocal Translocation:
TRANS L1 (described above)
TRANS R1 (described above)
KJneo (described above)
PGKr-2 (described above)

PCR is performed using the primers shown above, LA taq (Takara), and buffers and dNTPs (dATP, dCTP, DGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

The human chromosome 22 region is subjected to PCR. The primer sequences are shown below:
553P-F (described above)
553P-R (described above)
PPM1F L (described above)
PPM1F R (described above)
IGLVI-70 L (described above)
IGLVI-70 R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute. Primers for Confirmation of Human Chromosome 14 Region:
MTA1-F3 (described above)
MTA1-R3 (described above)

ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. PCR-positive cell lines are subjected to the subsequent analysis.

[F.3] Two-Color FISH Analysis

FISH analysis is performed using human cot-1 DNA and mouse cot-1 DNA as probes to confirm that the clones retains IGHL-NAC alone and maintains the normal mouse ES karyotype.

Two-color FISH analysis is performed using a combination of BAC clones CH17-95F2 (IGL region) and CH17-262H11 (IGH region) and a combination of BAC clones CH17-424L4 (IGL region) and CH17-212P11 (IGH region) as probes in order to thoroughly analyze whether or not IGHL-NAC is actually constructed. Clones in which signals indicating the presence of the IGL region and the IGH region are observed in the expected positions on NAC are designated as positive clones (designated as HKD31 IGHL-NAC) and subjected to injection.

[G] Transfer of IGHL-NAC into Rat ES Cells

In order to produce human antibody-producing rats, it is necessary to transfer IGHL-NAC into rat ES cells, inject the resulting cells into 8-cell-stage fertilized eggs, prepare chimeric rats, and allow IGHL-NAC to be transmitted to progeny.

[G.1] Microcell Fusion and Isolation of Drug Resistant Clone

IGHL-NAC is introduced into rat ES cells by the technique as with microcell fusion into mouse ES cells as described in Example 7 [F.1]. As donor cells, CHO K1 IGHL-NAC is used. Following the fusion, incubation is conducted overnight, G418 is added at a concentration of 150 g/ml, and selection culture is then conducted for 3 to 4 weeks. Clones found to be GFP-positive and drug resistant are subjected to the subsequent analysis.

[G.2] Selection of Drug Resistant Clones Via PCR Analysis

In order to confirm that IGHL-NAC is transferred into rat ES cells, PCR analysis is performed using DNAs extracted from the drug resistant clones as templates. The primers are shown below.

Primers for Confirmation of Site of Ligation by Reciprocal Translocation:
TRANS L1 (described above)
TRANS R1 (described above)
KJneo (described above)
PGKr-2 (described above)

PCR is performed using the primers shown above, LA taq (Takara), and buffers and dNTPs (dATP, dCTP, dGTP, and dTTP) included in the kit under the recommended conditions. Temperature and cycle conditions are as follows: thermal denaturation at 98° C. for 1 minute is followed by 30 cycles of 94° C. for 10 seconds, 60° C. for 30 seconds, and 72° C. for 3 minutes.

The human chromosome 22 region is subjected to PCR. The primer sequences are shown below:
553P-F (described above)
553P-R (described above)
PPM1F L (described above)
PPM1F R (described above)
IGLVI-70 L (described above)
IGLVI-70 R (described above)
hVpreB1-F (described above)
hVpreB1-Rm (described above)
hVpreB3-F (described above)
hVpreB3-R (described above)
hL5-F (described above)
hL5-R (described above)
344-F (described above)
344-R (described above)
350P-F (described above)
350P-R (described above)
IgL-F (described above)
IgL-Rm (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 63° C., 62° C., 60° C., 56° C., 55° C., or 50° C. for 30 seconds, and 72° C. for 1 minute.

Primers for Confirmation of Human Chromosome 14 Region:
MTA1-F3 (described above)
MTA1-R3 (described above)
ELK2P2-F (described above)
ELK2P2-R (described above)
g1(g2)-F (described above)
g1(g2)-R (described above)
VH3-F (described above)
VH3-R (described above)
CH3F3 (described above)
CH4R2 (described above)

PCR is performed using the primers shown above, Ampli Taq Gold (Applied Biosystems) as Taq polymerase, and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds or 56° C. for 30 seconds, and 72° C. for 1 minute. PCR-positive cell lines are subjected to the subsequent analysis.

[G.3] Two-Color FISH Analysis

FISH analysis is performed using human cot-1 DNA and mouse cot-1 DNA as probes to confirm that the clones retain one copy of IGHL-NAC independently and maintain the normal rat ES karyotype (42 chromosomes) as expected. Two-color FISH analysis is further performed using a combination of BAC clones CH17-95F2 (IGL region) and CH17-262H11 (IGH region) and a combination of BAC clones CH17-424L4 (IGL region) and CH17-212P11 and (IGH region) as probes in order to thoroughly analyze the IGHL-NAC structure. Clones in which signals indicating the presence of the IGL region and the IGH region are observed in the expected positions on NAC are designated as positive clones (designated as rESIGHL-NAC) and subjected to injection.

[H] Preparation of Mice and Rats Retaining IGHL-NAC and Preparation of Offspring Mice and Rats Mouse and rat ES cells retaining IGHL-NAC are subjected to the procedures as with Example 7 [H], [I], [J], and [K] to prepare offspring mice and rats retaining IGHL-NAC. Offspring mice and rats and chimeric mice obtained during the process of preparation are also subjected to analysis in the same manner as in Example 7 [H.4], [H.5], and [H.6] to confirm retention of IGHL-NAC and antibody expression (including hλ). The resulting IGHL-NAC-retaining mice and rats are designated as mTC (IGHL-NAC) and rTC (IGHL-NAC), respectively.

[Example 9] Preparation of Intact Human Antibody-Producing Mouse

A mouse retaining IGHK-NAC and IGHL-NAC is subjected to crossbreeding with a mouse with disrupted mouse Igh and Igk genes and with an Igl mutation (a mutation that lowers the Igl expression level) to prepare a human antibody-producing mouse.

[A] Preparation of Mouse Having Igh and Igk Gene Deletion (or Defect) and Expressing Igl at Low Level In order to produce a human antibody-producing mouse, a mouse lacking the mouse antibody gene or expressing the same at low level is produced.

[A.1] Preparation of Mouse Having Deletion (or Defect) of Igh and Igk Genes and Expressing Igl at Low Level A mouse linage generated from HKD31 mouse (in which mouse Igh and Igk genes have been disrupted) ES cells is subjected to crossbreeding with CD-1 having a mutation that lowers the mouse Igl expression level (ICR, purchased from Charles River) to produce a mouse having deletion (or defect) of Igh and Igk genes and expressing Igl at low level.

A mouse Iglc mutation derived from CD-1 is analyzed by PCR-RFLP.

PCR is carried out using the primers shown below:

```
mIglc1VnC L:
                                (SEQ ID NO: 119)
5'-CCTCAGGTTGGGCAGGAAGA-3'

J3C1:
                                (SEQ ID NO: 120)
5'-GACCTAGGAACAGTCAGCACGGG-3'
```

PCR is performed using Ampli Taq Gold (Applied Biosystems) as Taq polymerase and buffers and dNTPs (dATP, dCTP, DGTP, and dTTP) included in the kit under the recommended conditions. Temperature and cycle conditions are as follows: thermal denaturation at 95° C. for 10 minutes is followed by 35 cycles of 95° C. for 30 seconds, 60° C. for 30 seconds, and 72° C. for 1 minute.

PCR products are treated with KpnI-HF (NEB) and electrophoresed. Thereafter, PCR products in which no cleavage is observed are evaluated to carry mutant alleles. As a result, a mouse comprising Ig, mutation in both alleles is obtained (referred to as the "LD lineage").

[A.2] Evaluation of Mouse Antibody Gene Expression

Flow cytometry (FCM) and ELISA are carried out to confirm that mouse antibody expression is lost or substantially lost.

When the Igh gene is disrupted and Igμ expression is lost, as described in Example 7 [H.3], B cells are not produced. By determining the presence or absence of B cells, accordingly, Igh gene deletion (or defect) can be evaluated. FCM analysis is carried out as previously reported (Proc. Natl. Acad. Sci., U.S.A., Jan. 18 2000; 97(2): 722-7), and a mouse exhibiting B cell deletion is evaluated to lack the mouse Igh. Crossbreeding between a mouse in which the mouse Igh and Igκ might have been disrupted (referred to as the "HKD lineage") and a mouse with an Igλ mutation is advanced, so as to obtain a mouse with disrupted Igh and Igκ genes and comprising Igλ mutation in both alleles (called "HKLD lineage").

The resulting mice are also subjected to ELISA to analyze Igk and Igl expression, in addition to mouse Igh expression, in the same manner as previously reported (Proc. Natl. Acad. Sci., U.S.A., 2000 Jan. 18; 97(2): 722-7). Thus, lost expression and low-level expression are confirmed.

[A.3] Preparation of Human Antibody-Producing Mouse

An IGHK-NAC- or IGHL-NAC-carrying mouse is subjected to crossbreeding with a mouse with mouse IghKO, IgkKO, and Igl mutations to prepare an intact human antibody-producing mouse.

[B] Evaluation of Intact Human Antibody-Producing Mouse

[B.1] FACS Analysis

Flow cytometry analysis is carried out in order to confirm the presence of B cells carrying IGHK-NAC or IGHL-NAC. Blood cells are stained using an antibody to human IGM and mouse CD45R (B220) to identify human IGM-, CD45R-, and GFP-positive cells. Blood is drawn from the eye socket using a heparin-coated capillary, the blood is then transferred to a heparin-PBS-containing tube, and the tube is subjected to inversion mixing, followed by ice cooling. After centrifugation is performed at 2,000 rpm and 4° C. for 3 minutes, the supernatant is removed, various antibodies are added to proceed the reaction at 4° C. for 30 minutes, and the resultant is washed with PBS supplemented with 5% fetal bovine serum (5% FBS/PBS). After the final centrifugation, 1.2% dextran in physiological saline is added to the pellet, and, after tapping, the resultant is allowed to stand at room temperature for 45 minutes to naturally precipitate red blood cells. The supernatant is transferred into a new tube, centrifugation is carried out at 2,000 rpm and 4° C. for 3 minutes, the supernatant is removed, a hemolytic agent (0.17 M NH₄Cl) is added to the pellet at room temperature, and the resultant is then allowed to stand for 5 minutes. After centrifugation is performed at 2,000 rpm and 4° C. for 3 minutes, the resultant is washed with 5% FBS/PBS, and the resultant is then suspended in 500 μl of 5% FBS/PBS. The resulting suspension is analyzed by flow cytometry.

[B.2] Analysis of Human Antibody Expression

ELISA assay is performed to confirm expression of the human antibody light chain gene, the human antibody heavy chain gene, and various isotypes. In the same manner as Example 7 [H.4], whether or not the mouse antibody expression occurs is confirmed, and expression of mouse antibodies (mγ, mμ, mκ, and mλ) and human antibodies (hγ, hμ, hκ, hλ, hγ1, hγ2, hγ3, hγ4, hα, hε, and hδ) and concentrations of the antibodies in blood serum are measured.

[B.3] Expression Analysis and Sequencing of Human Antibody

The cDNA is synthesized from RNA obtained from the spleen of a human antibody-producing mouse, and the cloning and nucleotide sequencing of the human antibody gene variable regions are performed. Analysis and evaluation can be performed in the same manner as in Example 7 [H.5].

[B.4] Evaluation of Response to Antigen-Specific Human Antibody Production

A human antibody-producing mouse is evaluated as to whether or not the response to production of antigen-specific human antibodies could be observed. In accordance with the method described in Example 7 [H.6], the mouse is immunized with human serum albumin to analyze an increase in antibody titer.
[B.5] Obtaining Human Antibody-Producing Hybridoma from Human Antibody-Producing mouse
A human antibody-producing hybridoma can be obtained in the same manner as disclosed in the patent literature (WO 98/37757).

[Example 10] Preparation of Intact Human Antibody-Producing Rat

A rat carrying IGHK-NAC and IGHL-NAC is subjected to crossbreeding with a KO rat with disrupted rat Igh, Igk, and Igl to produce a human antibody-producing rat.
[A] Preparation and Evaluation of Human Antibody-Producing Rat
[A.1] Preparation of Human Antibody-Producing Rat
A rat carrying IGHK-NAC or IGHL-NAC is subjected to crossbreeding with a rat with disrupted rat Igh, Igκ, and Igλ to produce a human antibody-producing rat.
[A.2] FACS Analysis
B cells carrying IGHK-NAC or IGHL-NAC are analyzed in the same manner as in Example 14 [B.1] using an anti-rat CD45R (B220) antibody and a hemolytic agent (0.15 M $NH_4Cl$).
[A.3] Analysis of Human Ig Expression
ELISA assay is performed in the same manner as Example 7 [H.4] to confirm expression of the human antibody light chain gene, the human antibody heavy chain gene, and various isotypes. Thus, human antibody production is evaluated. Also, expression of rat antibodies (rγ, rμ, rκ, and rλ) is evaluated using anti-rat immunoglobulin antibodies.
[A.4] Analysis of Human Antibody Expression and Gene Sequencing
In the same manner as in Example 7 [H.5], sequencing, analysis, and evaluation of the antibody genes are performed.
[A.5] Evaluation of Response for Production of Antigen-Specific Human Antibodies
Evaluation is performed in the same manner as in Example 7 [H.6].
[A.6] Obtaining Human Antibody-Producing Hybridoma from Human Antibody-Producing Rat
A human antibody-producing hybridoma is obtained in the same manner as Example 9 [B.5].

[Example 11] Construction of Mouse Artificial Chromosome Vectors 10MAC2 and 10MAC3

As DNA insertion sequences, a PGKneo-5' HPRT-loxP type loxP sequence and a GFP-PGKneo-5' HPRT-loxP type loxP sequence are inserted into the mouse artificial chromosome 10MAC to construct the mouse artificial chromosome vectors 10MAC2 and 10MAC3. The resulting vectors 10MAC2 and 10MAC3 are introduced into hprt-deficient CHO cell line to introduce the genes with the aid of cyclic DNA, and operability is confirmed.
[A] Construction of Mouse Artificial Chromosome Vectors 10MAC2 and 10MAC3 by introducing PGKneo-5' HPRT-loxP type and GFP-PGKneo-5' HPRT-loxP type loxP sequences into mouse artificial chromosome 10MAC
10MAC that comprises a gene insertion site loxP alone introduced into the mouse artificial chromosome 10MAC, and another 10MAC comprises a gene insertion site loxP and a GFP expression unit capable of monitoring the presence of the loxP, are constructed.
[A.1] Preparation of PGKneo-5' HPRT-loxP Type and GFP-PGKneo-5' HPRT-loxP Type of loxP-Targeting Vectors
As a basic plasmid used for inserting the loxP sequence into DT40 (10MAC), V907 (Lexicon genetics) was used. The DNA sequence of mouse chromosome 10 as a loxP insertion site was obtained from the GenBank database (NC_000076.6). PCR was performed using genomic DNAs extracted from drug resistant clones as templates to amplify 2 target sequences for homologous recombination. The primer sequences are shown below.

NotI_m10 LA F:
(SEQ ID NO: 121)
5'-TCGAGCGGCCGCTCTAAGTCAGGGAAAGATCCCCTTCTTG-3'

SalI_m10 LA R:
(SEQ ID NO: 122)
5'-TCGAGTCGACGACCATGAAGATGGTCCAACTAAAGCAA-3'

ClaI_m10 RA F:
(SEQ ID NO: 123)
5'-TCGAATCGATCACTGCTCTTTCTTTAGTTACATGCAGCCC-3'

ClaI_m10 RA R:
(SEQ ID NO: 124)
5'-TCGAATCGATATTCTTGCCAAGCTACTCTTCCGAGCTA-3'

Figure 24:
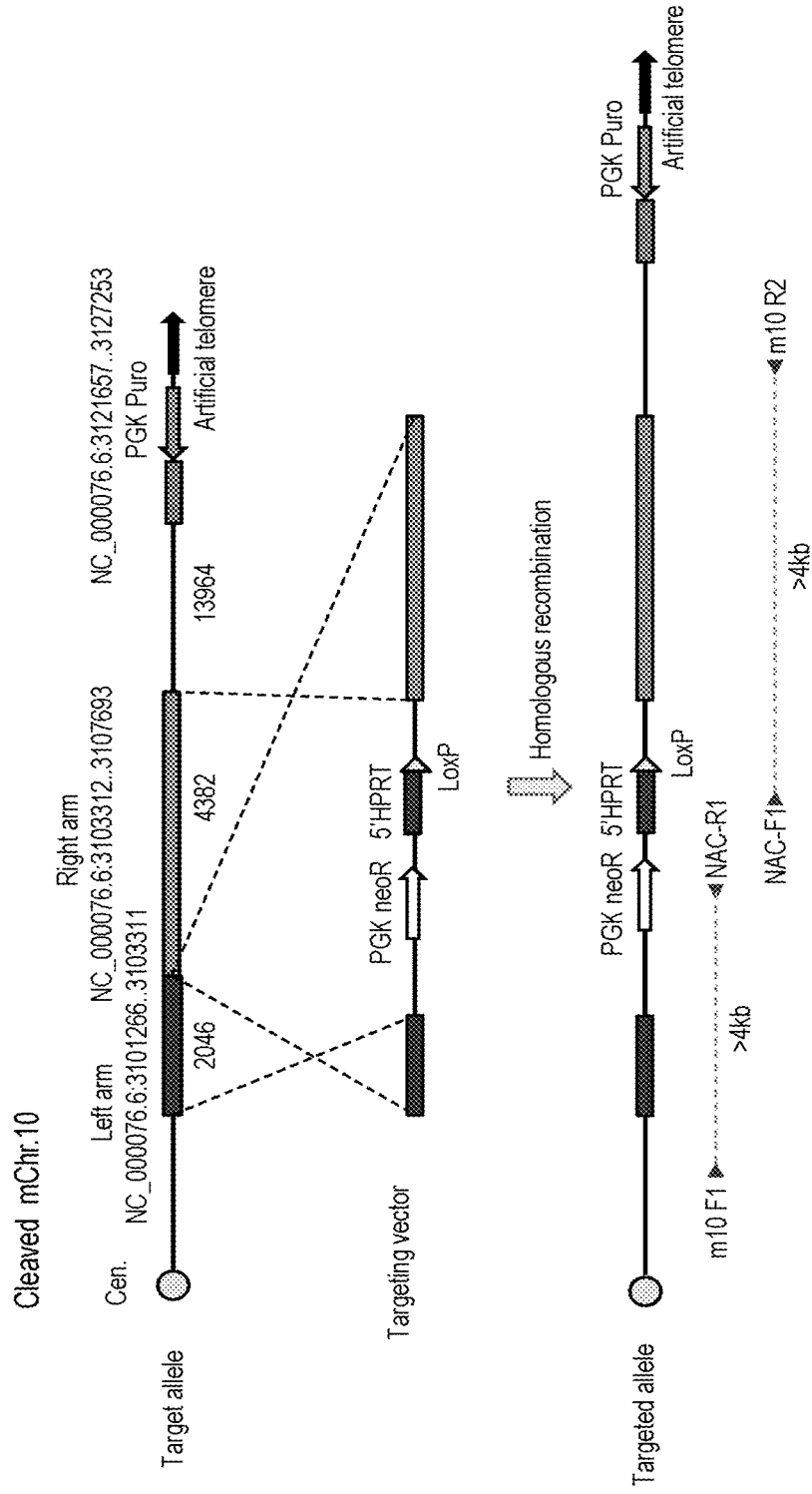
FIG. 24 schematically shows construction of 10MAC2 comprising the neomycin resistant gene and the loxP sequence for insertion of cyclic DNA in mouse chromosome 10 (10MAC).
Figure 25:
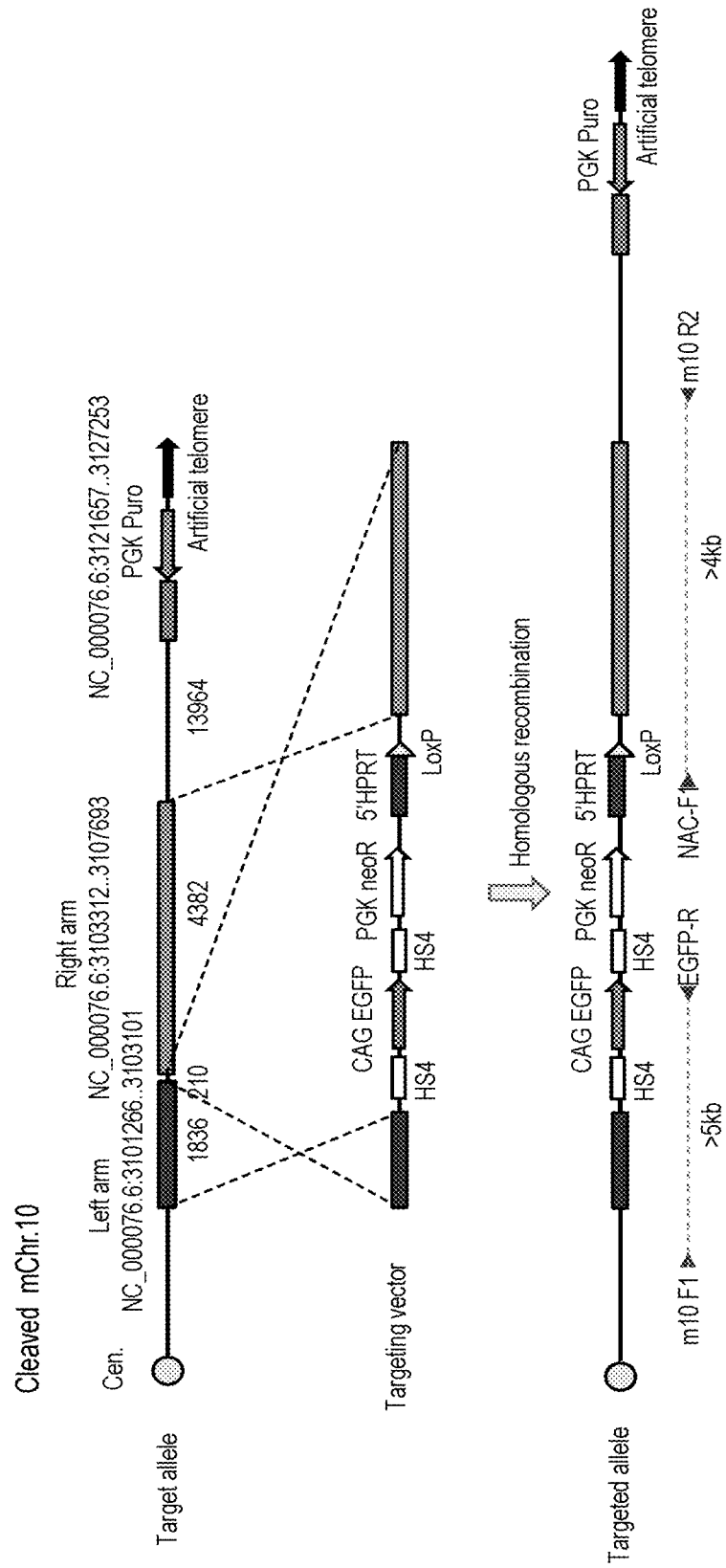
FIG. 25 schematically shows construction of 10MAC3 comprising the GFP fluorescent expression unit and the neomycin resistant gene and the loxP sequence for insertion of cyclic DNA in mouse chromosome 10 (10MAC).

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds, 68° C. for 3 minutes, and 68° C. for 5 minutes. Preparation of PGKneo-5' HPRT-loxP targeting vector
PGKneo was cloned into the EcoRI site of V907. 5' HPRT-loxP was inserted into the AscI site and the ClaI site. The PCR products of ClaI m10 RA F and of ClaI m10 RA R were digested with ClaI (NEB), separated by agarose gel, purified, and cloned into the ClaI site of V907 (vector name: V907-PGKneo-5' HPRT-loxP-m10RA). The PCR products of NotI_m10 LA F and of SalI_m10 LA R were digested with NotI (NEB) and SalI (NEB), separated by agarose gel, purified, and cloned into the NotI/SalI site of V907-PGKneo-5' HPRT-loxP-m10RA (vector name: p10MAC2).
Preparation of GFP-PGKneo-5' HPRT-loxP targeting vector
CAG-EGFP was cloned into the Not/SalI sites of V907-PGKneo-5' HPRT-loxP-m10RA. The PCR products of NotI_m10 LA F and of SalI_m10 LA R were digested with NotI (NEB) and PspOMI (NEB), separated by agarose gel, purified, and cloned into the NotI site of V907-EGFP-PGKneo-5' HPRT-loxP-m10RA (vector name: p10MAC3).
The targeting vector, the target sequence, and the chromosome allele resulting from homologous recombination are shown in FIGS. 24 and 25.
[A.2] Transfection and Isolation of G418 Resistant Clone
Chicken DT40 cells were cultured in RPMI 1640 medium (Gibco) supplemented with 10% fetal bovine serum (referred to as "FBS" hereinbelow, Gibco), 1% chicken serum (Gibco), and 10-4 M 2-mercaptoethanol (Sigma). Approximately $10^7$DT40 (10MAC) T5-26 cells were washed once with supplement-free RPMI 1640 medium, suspended in 0.5 ml of supplement-free RPMI 1640 medium, supplemented with 25 μg of the targeting vector p10MAC2 or p10MAC3 linearized with the restriction enzyme NotI (TAKARA), transferred to a cuvette (Bio-Rad Laboratories, Inc.) for electroporation, and allowed to stand at room temperature for 10 minutes. The cuvette was mounted on Gene Pulser (Bio-Rad Laboratories, Inc.), and voltage was applied under the conditions of 550 V and 25 µF. The resultant was allowed to stand at room temperature for 10 minutes and then cultured for 24 hours. The medium was exchanged with a medium containing G418 (1.5 mg/ml), dispensed into two 96-well culture plates, and then subjected to selection culture for about 2 weeks. A total of 24 resistant colonies of T5-26 and 20 resistant colonies of T6-37 obtained as a result of transfection conducted 2 times were isolated, amplified, and subjected to the subsequent analysis (clone names: DT40 (10MAC2) and DT40 (10MAC3)).

[A.3] Selection of Homologous Recombinant
[A.3.1] PCR Analysis

PCR was performed using the following primers in order to select a recombinant using genomic DNA extracted from the G418 resistant cell line as a template, and whether or not recombination has occurred in a site-directed manner on mouse chromosome 10 was examined. The primer sequences are shown below.

DT40 (10MAC2):
  m10 F1 (described above)
  NAC R1: 5'-CTCTTCAGCAATATCACGGGTAGC-CAAC-3' (SEQ ID NO: 125)
  NAC F1: 5'-TGCTTGCATTGTATGTCTGGCTAT-TCTG-3' (SEQ ID NO: 126)
  m10 R2 (described above)
  m10 F6 (described above)
  Puro I (described above)

DT40 (10MAC3):
m10 F1 (described above)
  EGFP-R: 5'-TGCTCAGGTAGTGGTTGTCG-3' (SEQ ID NO: 127)
  NAC F1 (described above)
  m10 R2 (described above)
  m10 F6 (described above)
  Puro I (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 5 minutes or 6 minutes.

The results indicate that target recombination had occurred in 14 and 11 clones derived from DT40 (10MAC2) and DT40 (10MAC3), respectively.

[A.3.2] Two-Color FISH Analysis

Figure 26:
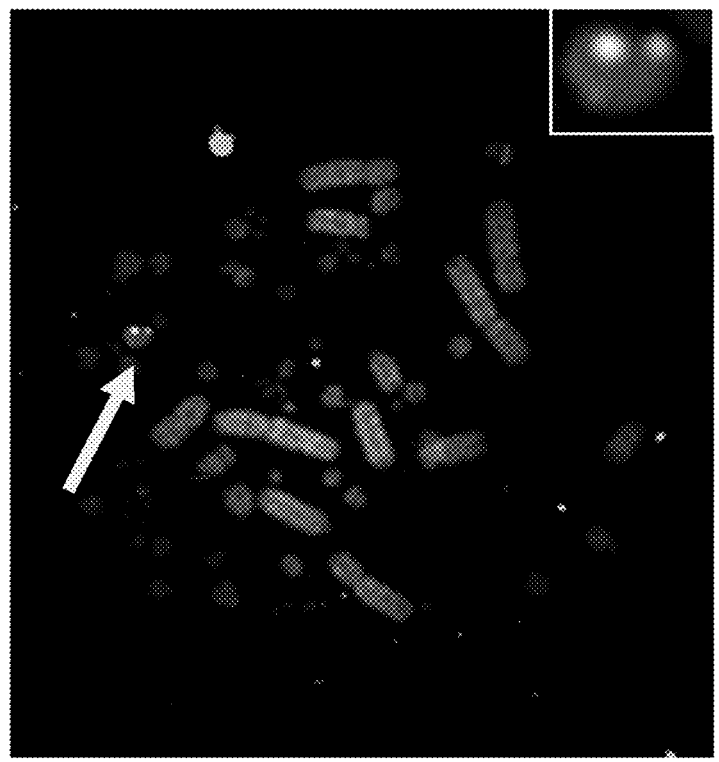
FIG. 26 shows an image obtained by FISH analysis of a DT40 cell retaining 10MAC2. An arrow indicates 10MAC2 constructed.
Figure 27:
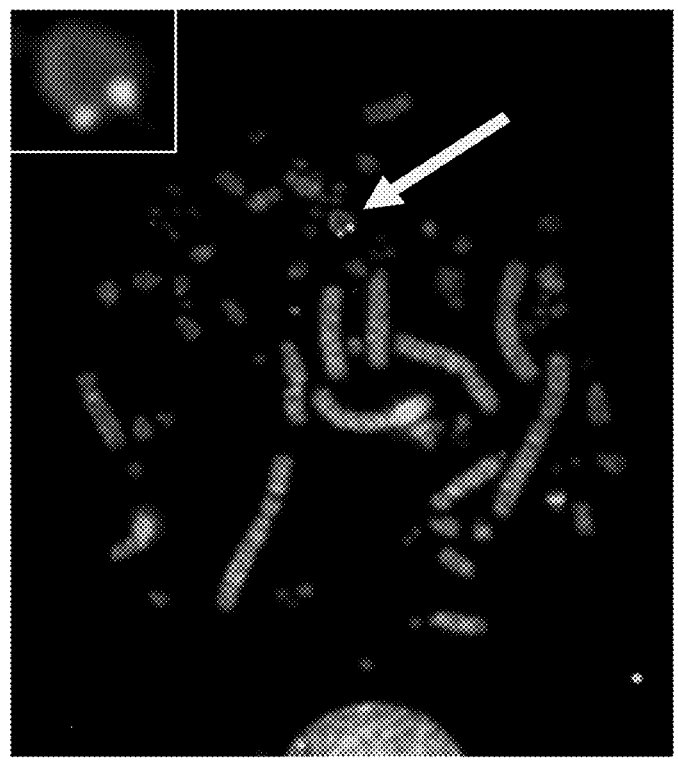
FIG. 27 shows an image obtained by FISH analysis of a DT40 cell retaining 10MAC3. An arrow indicates 10MAC3 constructed.

DT40s (10MAC2 and 10MAC3) obtained above were subjected to two-color FISH analysis in accordance with the method of Matsubara et al. (FISH test protocol, Shujunsha Co., Ltd., 1994). FISH analysis was performed using mouse cot-1 DNA and the 5' HPRT-loxP (X6.1) cassette as probes. As a result, a FITC signal derived from the probe was detected near the centromere of the mouse chromosome 10 fragment targeted to the loxP sequence. It was thus visually confirmed that site-directed recombination occurred (FIGS. 26 and 27). On the basis of the results above, it was concluded that DT40 cell clones comprising the mouse artificial chromosome vectors 10MAC2 and 10MAC3 were obtained. In the subsequent steps, a single clone of DT40 (10MAC2) #8 and a single clone of DT40 (10MAC3) #12 were used.

[B] Introduction of 10MAC2 and 10MAC3 from DT40 Cells Containing the Mouse Artificial Chromosome Vectors 10MAC2 and 10MAC3 into CHO Cells In order to introduce cyclic DNA retaining a target gene (or target genes) via a loxP sequence as a DNA sequence insertion site of the mouse artificial chromosome vector 10MAC2 or 10MAC3 within CHO cells or to introduce the mouse artificial chromosome vector 10MAC2 or 10MAC3 comprising a target gene (or target genes) introduced thereinto within CHO cells, 10MAC2 and 10MAC3 were introduced into CHO cells.

[B.1] Microcell Fusion and Isolation of Drug Resistant Clone

Microcell fusion was performed using DT40 (10MAC2) and DT40 (10MAC3) as donor cells and CHO (HPRT⁻), i.e., the CHO hprt-deficient cell (Accession Number: JCRB0218; the Health Science Research Resources Bank), in the same manner as described above. The G418 resistant colonies obtained by microcell fusion were isolated, amplified, and subjected to the subsequent analysis (clone names: CHO (HPRT⁻; 10MAC2) and CHO (HPRT⁻; 10MAC3)).

[B.2] Selection of Drug Resistant Clone
[B.2.1] PCR Analysis

PCR was performed using the following primers in order to select a recombinant using genomic DNA extracted from the G418 resistant cell line as a template, and whether or not the mouse artificial chromosome vectors 10MAC2 and 10MAC3 had been introduced into CHO cells was examined. The primer sequences are shown below.

CHO(HPRT⁻; 10MAC2):
  m10 F1 (described above)
  NAC R1 (described above)
  NAC F1 (described above)
  m10 R2 (described above)
  m10 F6 (described above)
  Puro I (described above)

CHO (HPRT⁻; 10MAC3):
  m10 F1 (described above)
  EGFP-R (described above)
  NAC F1 (described above)
  m10 R2 (described above)
  m10 F6 (described above)
  Puro I (described above)

PCR was performed using GeneAmp 9600 (PerkinElmer, Inc.) as a thermal cycler, KOD FX (TOYOBO) as Taq polymerase, and buffers and dNTPs (dATP, dCTP, dGTP, and dTTP) included in the kit under the recommended conditions. Temperature and cycle conditions were as follows: thermal denaturation at 98° C. for 1 minute was followed by 35 cycles of 98° C. for 15 seconds and 68° C. for 5 minutes or 6 minutes. As a result, 12 and 10 PCR-positive clones were obtained and subjected to the subsequent analysis.

[B.2.2] Mono-Color FISH Analysis

Figure 28:
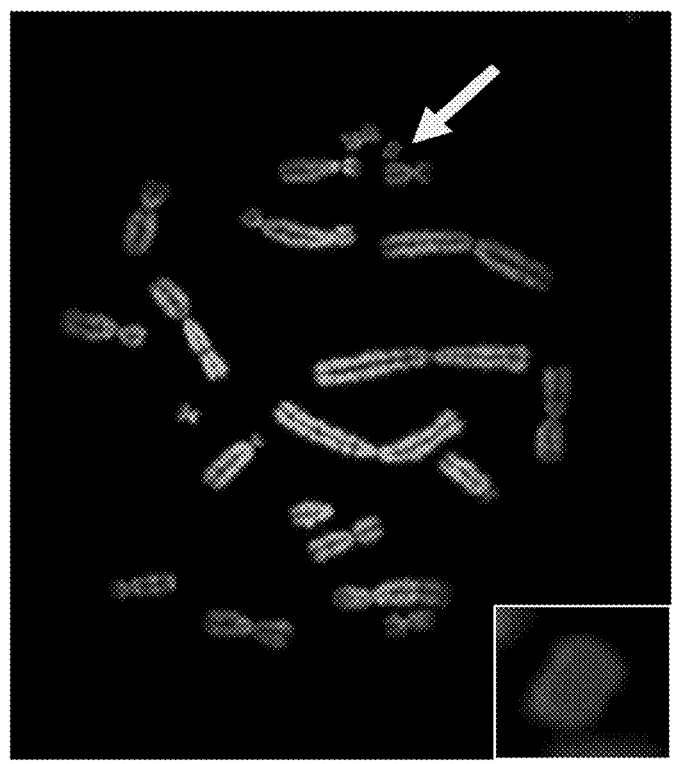
FIG. 28 shows an image obtained by FISH analysis of a CHO cell retaining 10MAC2. An arrow indicates 10MAC2.
Figure 29:
FIG. 29 shows an image obtained by FISH analysis of a CHO cell retaining 10MAC3. An arrow indicates 10MAC3.

The CHO (HPRT⁻; 10MAC2) and CHO (HPRT⁻; 10MAC3) clones (6 clones each) obtained above were subjected to FISH analysis using mouse cot-1 DNA as a probe in accordance with the report of Shinohara et al. (Human Molecular Genetics, 10: 1163-1175, 2001). As a result, it was confirmed that the mouse artificial chromosome vectors 10MAC2 and 10MAC3 were introduced into CHO cells. On the basis of the results of analysis, one clone was found to retain MAC2 independently and stably in CHO, and 2 clones were found to retain MAC3 independently and stably in CHO (FIGS. 28 and 29).

[C] Confirmation of Insertion of Cyclic DNA into MAC2 and MAC3

Whether or not cyclic DNA would be inserted into MAC2 and MAC3 via recombination was examined.

[C.1] Insertion of Cyclic DNA into MAC2 and MAC3 Using the Cre/loxP System

CHO (HPRT⁻; 10MAC2) and CHO (HPRT⁻; 10MAC3) cells were cultured to reach confluency in 6-cm dishes. A Cre expression plasmid (vector name: pBS185) and a LoxP-3' HPRT-EGFP plasmid (vector name: X3.1-I-EGFP-I) were introduced together into CHO (HPRT⁻; 10MAC2) using Lipofectamine 2000 in accordance with the manufacturer's instructions. pBS185 and a LoxP-3' HPRT-tdtomato plasmid (vector name: X3.1-I-tdtomato-1) were introduced together into CHO (HPRT⁻; 10MAC3). The cells were subjected to subculture in ten 10-cm cell culture dishes 24 hours later, and drug selection was then initiated using HAT 24 hours thereafter. The drug resistant clones obtained were subjected to the subsequent analysis.

[C.2] Analysis of Drug Resistant Clone

Upon occurrence of site-directed recombination as expected and insertion of cyclic DNA retaining LoxP-3' HPRT, the HPRT gene was reconstructed in 10MAC2 and 10MAC3, and HAT resistance was acquired. DNA was extracted from the drug resistant clone and PCR was performed to detect a joint of such recombination. The primers used are shown below.

TRANS L1 (described above)
TRANS R1 (described above)

PCR was performed using the primers shown above, LA taq (Takara), and buffers and dNTPs (dATP, dCTP, DGTP, and dTTP) included in the kit under the recommended conditions. Temperature and cycle conditions were as follows: thermal denaturation at 98° C. for 1 minute was followed by 30 cycles of 94° C. for 10 seconds, 60° C. for 30 seconds, and 72° C. for 3 minutes. On the basis of the results, cyclic DNA insertion efficiency via site-directed recombination was evaluated.

INDUSTRIAL APPLICABILITY

The mouse artificial chromosome vectors of the present invention can be subjected to various use and purposes, such as preparation of exogenous gene-expressing cells or useful non-human animals, and production of proteins including human antibodies.

Accession Numbers

The cell lines (1) and (2) indicated below are animal cell lines produced by introducing each mouse artificial chromosome derived from mouse chromosome 10 and mouse chromosome 16 into the DT40 chicken B cell line, respectively, via electroporation. These 2 animal cell lines were deposited internationally at the Patent Microorganisms Depositary, the National Institute of Technology and Evaluation (NPMD) (122, 2-5-8 Kazusakamatari, Kisarazu-shi, Chiba, 292-0818, Japan) under the terms of the Budapest Treaty on Feb. 28, 2018.
  (1) Accession Number of DT40 (10MAC) T5-26: NITE BP-02656
  (2) Accession Number of DT40 (16MAC) T1-14: NITE BP-02657

Sequence Listing Free Text

SEQ ID NOs: 1 to 127: primers

All publications, patents, and patent applications cited herein are incorporated herein by reference in their entirety.

The invention claimed is:

1. A mouse artificial chromosome vector, comprising:
a natural centromere derived from a mouse chromosome 10;
a mouse-chromosome-derived long-arm fragment formed by deleting gene Gm8155 and the entire long-arm region of mouse chromosome 10 distal to gene Gm8155 so as to substantially remove endogenous genes in the mouse chromosome;
a telomere sequence so as to form the mouse artificial chromosome vector contained in the deposited cell line DT40 (10MAC) T5-26 (NITE BP-02656),
wherein the vector is stably retained in cells and tissues of a mouse or rat at a retention rate of about 90% or more, and wherein the mouse artificial chromosome vector is capable of transmission to a progeny of the mouse or rat.

2. The vector of claim 1, further comprising at least one DNA sequence insertion site.

3. The vector of claim 2, wherein the DNA sequence insertion site selected from the group consisting of a loxP sequence, an FRT sequence, a φC31attB sequence, a φC31attP sequence, a R4attB sequence, a R4attP sequences, a TP901-1attB sequence, a TP901-1attP sequence, a Bxb1attB sequence, and a Bxb1attP sequence.

4. The vector of claim 1, further comprising:
a reporter gene, a selection marker gene, or a combination thereof.

5. The vector of claim 1, further comprising:
an exogenous DNA sequence.

6. The vector of claim 5, wherein the exogenous DNA sequence is a human DNA sequence.

7. The vector of claim 5, wherein the exogenous DNA sequence is a DNA sequence of a human-chromosome-derived long arm or short arm.

8. The vector of claim 5, wherein the exogenous DNA sequence is a human immunoglobulin heavy chain gene, a human immunoglobulin light chain gene, or a combination thereof.

9. The vector of claim 5, wherein the exogenous DNA sequence is a gene or DNA sequence encoding a polypeptide selected from the group consisting of a cytokine, hormone, growth factor, nutritional factor, hematopoietic factor, coagulation factor, hemolysis factor, G protein-coupled receptor, and enzyme, or a gene or DNA sequence used for treatment of a disease selected from the group consisting of a tumor, muscular dystrophy, hemophilia, neurodegenerative disease, autoimmune disease, allergic disease, and genetic disease or a gene or DNA sequence encoding a T-cell receptor or a human leukocyte antigen.

10. An isolated mouse or rat cell comprising the mouse artificial chromosome vector of claim 1.

11. The cell of claim 10, wherein the cell is selected from the group consisting of somatic cell, stem cell, and precursor cell.

12. A method for producing a protein, the method comprising: culturing the isolated cell of claim 10 comprising the mouse artificial chromosome vector comprising an exogenous DNA sequence to produce a protein encoded by the exogenous DNA; and collecting the protein produced that is encoded by the DNA.

* * * * *

SEQUENCE LISTING

```
<160> NUMBER OF SEQ ID NOS: 127

<210> SEQ ID NO 1
<211> LENGTH: 14
<212> TYPE: DNA
<213> ORGANISM: Artificial
<220> FEATURE:
<223> OTHER INFORMATION: primer

<400> SEQUENCE: 1
aattcggcgc gccg                                                     14

<210> SEQ ID NO 2
<211> LENGTH: 40
<212> TYPE: DNA
<213> ORGANISM: Artificial
<220> FEATURE:
<223> OTHER INFORMATION: primer

<400> SEQUENCE: 2
tcgaggcgcg ccagccttct agggaacagg agatgttcaa                         40

<210> SEQ ID NO 3
<211> LENGTH: 38
<212> TYPE: DNA
<213> ORGANISM: Artificial
<220> FEATURE:
<223> OTHER INFORMATION: primer

<400> SEQUENCE: 3
```

```
tcgaggatcc gccttgagtg gggttctagt catctttc                      38
```

<210> SEQ ID NO 4
<211> LENGTH: 28
<212> TYPE: DNA
<213> ORGANISM: Artificial
<220> FEATURE:
<223> OTHER INFORMATION: primer

<400> SEQUENCE: 4

```
aactacccag ttctgcattt ggtgtgag                                 28
```

<210> SEQ ID NO 5
<211> LENGTH: 28
<212> TYPE: DNA
<213> ORGANISM: Artificial
<220> FEATURE:
<223> OTHER INFORMATION: primer

<400> SEQUENCE: 5

```
atcagtcatc agtacccccca acctctct                                28
```

<210> SEQ ID NO 6
<211> LENGTH: 24
<212> TYPE: DNA
<213> ORGANISM: Artificial
<220> FEATURE:
<223> OTHER INFORMATION: primer

<400> SEQUENCE: 6

```
gagctgcaag aactcttcct cacg                                     24
```

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7

```
tggatgggtt tcaatgccac t                                        21
```

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8

```
ggcattctcc cctgttgtgg                                          20
```

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

```
accccctcgaa cccctattgc                                         20
```

<210> SEQ ID NO 10
<211> LENGTH: 20
<212> TYPE: DNA

<213> ORGANISM: Artificial
<220> FEATURE:
<223> OTHER INFORMATION: primer

<400> SEQUENCE: 10
cacgccatcg gtgatggata        20

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
tgggatgacc cccacttctt t        21

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ttttggcctc ttgccccata        20

<210> SEQ ID NO 13
<211> LENGTH: 38
<212> TYPE: DNA
<213> ORGANISM: Artificial
<220> FEATURE:
<223> OTHER INFORMATION: primer

<400> SEQUENCE: 13
tcgaggtacc tctaagtcag ggaaagatcc ccttcttg        38

<210> SEQ ID NO 14
<211> LENGTH: 38
<212> TYPE: DNA
<213> ORGANISM: Artificial
<220> FEATURE:
<223> OTHER INFORMATION: primer

<400> SEQUENCE: 14
tcgactcgag gaccatgaag atggtccaac taaagcaa        38

<210> SEQ ID NO 15
<211> LENGTH: 40
<212> TYPE: DNA
<213> ORGANISM: Artificial
<220> FEATURE:
<223> OTHER INFORMATION: primer

<400> SEQUENCE: 15
tcgagtcgac cactgctctt tctttagtta catgcagccc        40

<210> SEQ ID NO 16
<211> LENGTH: 40
<212> TYPE: DNA
<213> ORGANISM: Artificial
<220> FEATURE:
<223> OTHER INFORMATION: primer

<400> SEQUENCE: 16
tcgagcggcc gcattcttgc caagctactc ttccgagcta        40

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
tgagaaatac cgaatggcag agaaacac                                    28

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
cctgaagttc atctgcacca                                             20

<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19
catcgccttc tatcgccttc ttgacg                                      26

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
gagaggaggg aagcttgatg agaaaatg                                    28

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
tggaggccat aaacaagaag ac                                          22

<210> SEQ ID NO 22
<211> LENGTH: 21
<212> TYPE: DNA
<213> ORGANISM: Artificial
<220> FEATURE:
<223> OTHER INFORMATION: primer

<400> SEQUENCE: 22
ccccttgacc cagaaattcc a                                           21

<210> SEQ ID NO 23
<211> LENGTH: 38
<212> TYPE: DNA
<213> ORGANISM: Artificial
<220> FEATURE:

<223> OTHER INFORMATION: primer

<400> SEQUENCE: 23
tcgaggatcc gggagtaatt ttcaatcctt gaggcaga                              38

<210> SEQ ID NO 24
<211> LENGTH: 38
<212> TYPE: DNA
<213> ORGANISM: Artificial
<220> FEATURE:
<223> OTHER INFORMATION: primer

<400> SEQUENCE: 24
tcgaagatct catcagtgta caccacaatc ccatctgt                              38

<210> SEQ ID NO 25
<211> LENGTH: 28
<212> TYPE: DNA
<213> ORGANISM: Artificial
<220> FEATURE:
<223> OTHER INFORMATION: primer

<400> SEQUENCE: 25
cctcttcttg acggttacca cattttgc                                         28

<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
tgaattggtc cctcctgctc a                                                21

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
caggccatga gacccagaca                                                  20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tcctcggaga atggctcctg                                                  20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
ggcaggttga tgggaactgg                                                  20

```
<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
aaccagggtc cccatcctgt                                                     20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
tgggctggtt tcaatgctga                                                     20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
gtgtggccat ggctggagta                                                     20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
tgttcctctg ctgccactcg                                                     20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
acccagccac tcccaccata                                                     20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
aagggcatgg ctatcccaca                                                     20

<210> SEQ ID NO 36
<211> LENGTH: 38
<212> TYPE: DNA
<213> ORGANISM: Artificial
<220> FEATURE:
<223> OTHER INFORMATION: primer
```

-continued

```
<400> SEQUENCE: 36
tcgaggtacc gggagtaatt ttcaatcctt gaggcaga                              38

<210> SEQ ID NO 37
<211> LENGTH: 38
<212> TYPE: DNA
<213> ORGANISM: Artificial
<220> FEATURE:
<223> OTHER INFORMATION: primer

<400> SEQUENCE: 37
tcgactcgag tggcactgac cccttaatta cgtacaga                              38

<210> SEQ ID NO 38
<211> LENGTH: 37
<212> TYPE: DNA
<213> ORGANISM: Artificial
<220> FEATURE:
<223> OTHER INFORMATION: primer

<400> SEQUENCE: 38
tcgagtcgac aaagatttgc atccttggcc atgactc                               37

<210> SEQ ID NO 39
<211> LENGTH: 40
<212> TYPE: DNA
<213> ORGANISM: Artificial
<220> FEATURE:
<223> OTHER INFORMATION: primer

<400> SEQUENCE: 39
tcgagcggcc gccatcagtg tacaccacaa tcccatctgt                            40

<210> SEQ ID NO 40
<211> LENGTH: 38
<212> TYPE: DNA
<213> ORGANISM: Artificial
<220> FEATURE:
<223> OTHER INFORMATION: primer

<400> SEQUENCE: 40
tcgaggtacc aagaacaagc ttcagaacac agccagac                              38

<210> SEQ ID NO 41
<211> LENGTH: 39
<212> TYPE: DNA
<213> ORGANISM: Artificial
<220> FEATURE:
<223> OTHER INFORMATION: primer

<400> SEQUENCE: 41
tcgactcgag aacttgtcac acagatccta ctggaggtg                             39

<210> SEQ ID NO 42
<211> LENGTH: 39
<212> TYPE: DNA
<213> ORGANISM: Artificial
<220> FEATURE:
<223> OTHER INFORMATION: primer

<400> SEQUENCE: 42
tcgagtcgac ccacagactg aagcaattga cctcaaaag                             39

<210> SEQ ID NO 43
<211> LENGTH: 40
```

```
<212> TYPE: DNA
<213> ORGANISM: Artificial
<220> FEATURE:
<223> OTHER INFORMATION: primer

<400> SEQUENCE: 43
tcgagcggcc gcaaagcagt tatccgctat ttgggacctt                    40

<210> SEQ ID NO 44
<211> LENGTH: 28
<212> TYPE: DNA
<213> ORGANISM: Artificial
<220> FEATURE:
<223> OTHER INFORMATION: primer

<400> SEQUENCE: 44
catgcacatt tgcttacaca cagaggtt                                 28

<210> SEQ ID NO 45
<211> LENGTH: 28
<212> TYPE: DNA
<213> ORGANISM: Artificial
<220> FEATURE:
<223> OTHER INFORMATION: primer

<400> SEQUENCE: 45
atctgggcac tggggtacaa ctgttaat                                 28

<210> SEQ ID NO 46
<211> LENGTH: 29
<212> TYPE: DNA
<213> ORGANISM: Artificial
<220> FEATURE:
<223> OTHER INFORMATION: primer

<400> SEQUENCE: 46
ctgagaagag tcattgttta tggtagact                                29

<210> SEQ ID NO 47
<211> LENGTH: 28
<212> TYPE: DNA
<213> ORGANISM: Artificial
<220> FEATURE:
<223> OTHER INFORMATION: primer

<400> SEQUENCE: 47
atccccatgt gtatcactgg caaactgt                                 28

<210> SEQ ID NO 48
<211> LENGTH: 28
<212> TYPE: DNA
<213> ORGANISM: Artificial
<220> FEATURE:
<223> OTHER INFORMATION: primer

<400> SEQUENCE: 48
ggggaataaa cacccttttcc aaatcctc                                28

<210> SEQ ID NO 49
<211> LENGTH: 28
<212> TYPE: DNA
<213> ORGANISM: Artificial
<220> FEATURE:
<223> OTHER INFORMATION: primer

<400> SEQUENCE: 49
```

```
accaagtaac cgatcaaacc aacccttg                                              28

<210> SEQ ID NO 50
<211> LENGTH: 28
<212> TYPE: DNA
<213> ORGANISM: Artificial
<220> FEATURE:
<223> OTHER INFORMATION: primer

<400> SEQUENCE: 50
tgagaacaca ggggtctcca ttctgact                                              28

<210> SEQ ID NO 51
<211> LENGTH: 28
<212> TYPE: DNA
<213> ORGANISM: Artificial
<220> FEATURE:
<223> OTHER INFORMATION: primer

<400> SEQUENCE: 51
acaatcaaca gcatccccat ctctgaag                                              28

<210> SEQ ID NO 52
<211> LENGTH: 28
<212> TYPE: DNA
<213> ORGANISM: Artificial
<220> FEATURE:
<223> OTHER INFORMATION: primer

<400> SEQUENCE: 52
gacgtgctac ttccatttgt cacgtcct                                              28

<210> SEQ ID NO 53
<211> LENGTH: 28
<212> TYPE: DNA
<213> ORGANISM: Artificial
<220> FEATURE:
<223> OTHER INFORMATION: primer

<400> SEQUENCE: 53
tggtcactga agctttccat ctgctctt                                              28

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
agctcagaga cacctctcca                                                       20

<210> SEQ ID NO 55
<211> LENGTH: 25
<212> TYPE: DNA
<213> ORGANISM: Artificial
<220> FEATURE:
<223> OTHER INFORMATION: primer

<400> SEQUENCE: 55
ctgtattagg atacttggct attga                                                 25

<210> SEQ ID NO 56
<211> LENGTH: 25
<212> TYPE: DNA
<213> ORGANISM: Artificial
```

<220> FEATURE:
<223> OTHER INFORMATION: primer

<400> SEQUENCE: 56
tatcaagggg gtgtcggaaa tcgtg                                    25

<210> SEQ ID NO 57
<211> LENGTH: 25
<212> TYPE: DNA
<213> ORGANISM: Artificial
<220> FEATURE:
<223> OTHER INFORMATION: primer

<400> SEQUENCE: 57
actgggcctg ggagaacctg agact                                    25

<210> SEQ ID NO 58
<211> LENGTH: 22
<212> TYPE: DNA
<213> ORGANISM: Artificial
<220> FEATURE:
<223> OTHER INFORMATION: primer

<400> SEQUENCE: 58
aggtgctgct gggtggtcaa gt                                       22

<210> SEQ ID NO 59
<211> LENGTH: 23
<212> TYPE: DNA
<213> ORGANISM: Artificial
<220> FEATURE:
<223> OTHER INFORMATION: primer

<400> SEQUENCE: 59
gctcctgcaa atgtctcctg tca                                      23

<210> SEQ ID NO 60
<211> LENGTH: 24
<212> TYPE: DNA
<213> ORGANISM: Artificial
<220> FEATURE:
<223> OTHER INFORMATION: primer

<400> SEQUENCE: 60
cttacccagg ctccaggctc tatt                                     24

<210> SEQ ID NO 61
<211> LENGTH: 25
<212> TYPE: DNA
<213> ORGANISM: Artificial
<220> FEATURE:
<223> OTHER INFORMATION: primer

<400> SEQUENCE: 61
ctctacctcc ctaccccatc atcac                                    25

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
tggaaggtgg ataacgccct                                          20

```
<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
tcattctcct ccaacattag ca                                               22

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
agtcagggca ttagcagtgc                                                  20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
gctgctgatg gtgagagtga                                                  20

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
ctctcctgca gggccagtca                                                  20

<210> SEQ ID NO 67
<211> LENGTH: 22
<212> TYPE: DNA
<213> ORGANISM: Artificial
<220> FEATURE:
<223> OTHER INFORMATION: primer

<400> SEQUENCE: 67
tgctgatggt gagagtgaac tc                                               22

<210> SEQ ID NO 68
<211> LENGTH: 25
<212> TYPE: DNA
<213> ORGANISM: Artificial
<220> FEATURE:
<223> OTHER INFORMATION: primer

<400> SEQUENCE: 68
ctctaactga atcaagggaa tgaac                                            25

<210> SEQ ID NO 69
<211> LENGTH: 24
<212> TYPE: DNA
<213> ORGANISM: Artificial
<220> FEATURE:
<223> OTHER INFORMATION: primer
```

```
<400> SEQUENCE: 69
agcagtttga gtttaggatg aagg                                  24

<210> SEQ ID NO 70
<211> LENGTH: 26
<212> TYPE: DNA
<213> ORGANISM: Artificial
<220> FEATURE:
<223> OTHER INFORMATION: primer

<400> SEQUENCE: 70
catcgccttc tatcgccttc ttgacg                                26

<210> SEQ ID NO 71
<211> LENGTH: 28
<212> TYPE: DNA
<213> ORGANISM: Artificial
<220> FEATURE:
<223> OTHER INFORMATION: primer

<400> SEQUENCE: 71
atctgcacga gactagtgag acgtgcta                              28

<210> SEQ ID NO 72
<211> LENGTH: 28
<212> TYPE: DNA
<213> ORGANISM: Artificial
<220> FEATURE:
<223> OTHER INFORMATION: primer

<400> SEQUENCE: 72
agcaattagg gcctgtgcat ctcacttt                              28

<210> SEQ ID NO 73
<211> LENGTH: 28
<212> TYPE: DNA
<213> ORGANISM: Artificial
<220> FEATURE:
<223> OTHER INFORMATION: primer

<400> SEQUENCE: 73
ccagctcatt cctcccactc atgatcta                              28

<210> SEQ ID NO 74
<211> LENGTH: 28
<212> TYPE: DNA
<213> ORGANISM: Artificial
<220> FEATURE:
<223> OTHER INFORMATION: primer

<400> SEQUENCE: 74
catctggagt cctattgaca tcgccagt                              28

<210> SEQ ID NO 75
<211> LENGTH: 28
<212> TYPE: DNA
<213> ORGANISM: Artificial
<220> FEATURE:
<223> OTHER INFORMATION: primer

<400> SEQUENCE: 75
cttattcctc cttctgccca cccttcat                              28

<210> SEQ ID NO 76
```

```
<211> LENGTH: 24
<212> TYPE: DNA
<213> ORGANISM: Artificial
<220> FEATURE:
<223> OTHER INFORMATION: primer

<400> SEQUENCE: 76
agcactttac gcatcccagc atgt                                          24

<210> SEQ ID NO 77
<211> LENGTH: 24
<212> TYPE: DNA
<213> ORGANISM: Artificial
<220> FEATURE:
<223> OTHER INFORMATION: primer

<400> SEQUENCE: 77
ccaagagagt agtcgtgccc ctca                                          24

<210> SEQ ID NO 78
<211> LENGTH: 20
<212> TYPE: DNA
<213> ORGANISM: Artificial
<220> FEATURE:
<223> OTHER INFORMATION: primer

<400> SEQUENCE: 78
cccactttac cgtgctcatt                                               20

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
atgaaggtcc gtgactttgg                                               20

<210> SEQ ID NO 80
<211> LENGTH: 25
<212> TYPE: DNA
<213> ORGANISM: Artificial
<220> FEATURE:
<223> OTHER INFORMATION: primer

<400> SEQUENCE: 80
accccaaagg ccaaactctc cactc                                         25

<210> SEQ ID NO 81
<211> LENGTH: 24
<212> TYPE: DNA
<213> ORGANISM: Artificial
<220> FEATURE:
<223> OTHER INFORMATION: primer

<400> SEQUENCE: 81
cacttgtact ccttgccatt cagc                                          24

<210> SEQ ID NO 82
<211> LENGTH: 20
<212> TYPE: DNA
<213> ORGANISM: Artificial
<220> FEATURE:
<223> OTHER INFORMATION: primer

<400> SEQUENCE: 82
```
agtgagataa gcagtggatg                                             20

<210> SEQ ID NO 83
<211> LENGTH: 20
<212> TYPE: DNA
<213> ORGANISM: Artificial
<220> FEATURE:
<223> OTHER INFORMATION: primer

<400> SEQUENCE: 83
cttgtgctac tcccatcact                                             20

<210> SEQ ID NO 84
<211> LENGTH: 20
<212> TYPE: DNA
<213> ORGANISM: Artificial
<220> FEATURE:
<223> OTHER INFORMATION: primer

<400> SEQUENCE: 84
aggccagcat ctgcgaggat                                             20

<210> SEQ ID NO 85
<211> LENGTH: 20
<212> TYPE: DNA
<213> ORGANISM: Artificial
<220> FEATURE:
<223> OTHER INFORMATION: primer

<400> SEQUENCE: 85
gtggcagcaa gtagacatcg                                             20

<210> SEQ ID NO 86
<211> LENGTH: 28
<212> TYPE: DNA
<213> ORGANISM: Artificial
<220> FEATURE:
<223> OTHER INFORMATION: primer

<400> SEQUENCE: 86
cctattggcg ttactatggg aacatacg                                    28

<210> SEQ ID NO 87
<211> LENGTH: 28
<212> TYPE: DNA
<213> ORGANISM: Artificial
<220> FEATURE:
<223> OTHER INFORMATION: primer

<400> SEQUENCE: 87
cctgccttct tgtttcagct ctcaactg                                    28

<210> SEQ ID NO 88
<211> LENGTH: 28
<212> TYPE: DNA
<213> ORGANISM: Artificial
<220> FEATURE:
<223> OTHER INFORMATION: primer

<400> SEQUENCE: 88
gacgtgctac ttccatttgt cacgtcct                                    28

<210> SEQ ID NO 89
<211> LENGTH: 28
<212> TYPE: DNA

```
<213> ORGANISM: Artificial
<220> FEATURE:
<223> OTHER INFORMATION: primer

<400> SEQUENCE: 89
atccccatgt gtatcactgg caaactgt                                              28

<210> SEQ ID NO 90
<211> LENGTH: 28
<212> TYPE: DNA
<213> ORGANISM: Artificial
<220> FEATURE:
<223> OTHER INFORMATION: primer

<400> SEQUENCE: 90
acactttagt ccctgtcccc tcaacgag                                              28

<210> SEQ ID NO 91
<211> LENGTH: 28
<212> TYPE: DNA
<213> ORGANISM: Artificial
<220> FEATURE:
<223> OTHER INFORMATION: primer

<400> SEQUENCE: 91
tgcaggtatc tgttggtgtc cctgtttt                                              28

<210> SEQ ID NO 92
<211> LENGTH: 28
<212> TYPE: DNA
<213> ORGANISM: Artificial
<220> FEATURE:
<223> OTHER INFORMATION: primer

<400> SEQUENCE: 92
gacgtgctac ttccatttgt cacgtcct                                              28

<210> SEQ ID NO 93
<211> LENGTH: 28
<212> TYPE: DNA
<213> ORGANISM: Artificial
<220> FEATURE:
<223> OTHER INFORMATION: primer

<400> SEQUENCE: 93
agcagagctc gtttagtgaa ccgtcaga                                              28

<210> SEQ ID NO 94
<211> LENGTH: 28
<212> TYPE: DNA
<213> ORGANISM: Artificial
<220> FEATURE:
<223> OTHER INFORMATION: primer

<400> SEQUENCE: 94
ctgtcctatc cttgcagctg tcttccag                                              28

<210> SEQ ID NO 95
<211> LENGTH: 25
<212> TYPE: DNA
<213> ORGANISM: Artificial
<220> FEATURE:
<223> OTHER INFORMATION: primer

<400> SEQUENCE: 95
agatctcttg agcccagcag tttga                                                 25
```

```
<210> SEQ ID NO 96
<211> LENGTH: 24
<212> TYPE: DNA
<213> ORGANISM: Artificial
<220> FEATURE:
<223> OTHER INFORMATION: primer

<400> SEQUENCE: 96
tgaagttagc cggggataca gacg                                          24

<210> SEQ ID NO 97
<211> LENGTH: 20
<212> TYPE: DNA
<213> ORGANISM: Artificial
<220> FEATURE:
<223> OTHER INFORMATION: primer

<400> SEQUENCE: 97
aacggcagcc aaaccaaaga                                               20

<210> SEQ ID NO 98
<211> LENGTH: 20
<212> TYPE: DNA
<213> ORGANISM: Artificial
<220> FEATURE:
<223> OTHER INFORMATION: primer

<400> SEQUENCE: 98
accaggactg gctgggcata                                               20

<210> SEQ ID NO 99
<211> LENGTH: 20
<212> TYPE: DNA
<213> ORGANISM: Artificial
<220> FEATURE:
<223> OTHER INFORMATION: primer

<400> SEQUENCE: 99
agtctgcgct gacccaggaa                                               20

<210> SEQ ID NO 100
<211> LENGTH: 20
<212> TYPE: DNA
<213> ORGANISM: Artificial
<220> FEATURE:
<223> OTHER INFORMATION: primer

<400> SEQUENCE: 100
ttgagccaga gaagcggtca                                               20

<210> SEQ ID NO 101
<211> LENGTH: 20
<212> TYPE: DNA
<213> ORGANISM: Artificial
<220> FEATURE:
<223> OTHER INFORMATION: primer

<400> SEQUENCE: 101
tccacttggg ggtctgcatt                                               20

<210> SEQ ID NO 102
<211> LENGTH: 20
<212> TYPE: DNA
<213> ORGANISM: Artificial
<220> FEATURE:
```

-continued

<223> OTHER INFORMATION: primer

<400> SEQUENCE: 102
tggtgctgag cagctgtgtg                                        20

<210> SEQ ID NO 103
<211> LENGTH: 20
<212> TYPE: DNA
<213> ORGANISM: Artificial
<220> FEATURE:
<223> OTHER INFORMATION: primer

<400> SEQUENCE: 103
tgggacttag gtgggccaga                                        20

<210> SEQ ID NO 104
<211> LENGTH: 20
<212> TYPE: DNA
<213> ORGANISM: Artificial
<220> FEATURE:
<223> OTHER INFORMATION: primer

<400> SEQUENCE: 104
gcctccccaa gagcctgaat                                        20

<210> SEQ ID NO 105
<211> LENGTH: 25
<212> TYPE: DNA
<213> ORGANISM: Artificial
<220> FEATURE:
<223> OTHER INFORMATION: primer

<400> SEQUENCE: 105
tgtcctgggc tcctgtcctg ctcat                                  25

<210> SEQ ID NO 106
<211> LENGTH: 20
<212> TYPE: DNA
<213> ORGANISM: Artificial
<220> FEATURE:
<223> OTHER INFORMATION: primer

<400> SEQUENCE: 106
ggcggcgact ccaccctctt                                        20

<210> SEQ ID NO 107
<211> LENGTH: 22
<212> TYPE: DNA
<213> ORGANISM: Artificial
<220> FEATURE:
<223> OTHER INFORMATION: primer

<400> SEQUENCE: 107
cactgcctgc ccgctgctgg ta                                     22

<210> SEQ ID NO 108
<211> LENGTH: 21
<212> TYPE: DNA
<213> ORGANISM: Artificial
<220> FEATURE:
<223> OTHER INFORMATION: primer

<400> SEQUENCE: 108
gggcggggaa gtgggggaga g                                      21

```
<210> SEQ ID NO 109
<211> LENGTH: 25
<212> TYPE: DNA
<213> ORGANISM: Artificial
<220> FEATURE:
<223> OTHER INFORMATION: primer

<400> SEQUENCE: 109
agccccaaga acccagccga tgtga                                              25

<210> SEQ ID NO 110
<211> LENGTH: 25
<212> TYPE: DNA
<213> ORGANISM: Artificial
<220> FEATURE:
<223> OTHER INFORMATION: primer

<400> SEQUENCE: 110
ggcagaggga gtgtggggtg ttgtg                                              25

<210> SEQ ID NO 111
<211> LENGTH: 20
<212> TYPE: DNA
<213> ORGANISM: Artificial
<220> FEATURE:
<223> OTHER INFORMATION: primer

<400> SEQUENCE: 111
atcatctgct cgctctctcc                                                    20

<210> SEQ ID NO 112
<211> LENGTH: 20
<212> TYPE: DNA
<213> ORGANISM: Artificial
<220> FEATURE:
<223> OTHER INFORMATION: primer

<400> SEQUENCE: 112
cacatctgta gtggctgtgg                                                    20

<210> SEQ ID NO 113
<211> LENGTH: 20
<212> TYPE: DNA
<213> ORGANISM: Artificial
<220> FEATURE:
<223> OTHER INFORMATION: primer

<400> SEQUENCE: 113
accagcgcgt catcatcaag                                                    20

<210> SEQ ID NO 114
<211> LENGTH: 20
<212> TYPE: DNA
<213> ORGANISM: Artificial
<220> FEATURE:
<223> OTHER INFORMATION: primer

<400> SEQUENCE: 114
atcgccagcc tcaccatttc                                                    20

<210> SEQ ID NO 115
<211> LENGTH: 22
<212> TYPE: DNA
<213> ORGANISM: Artificial
<220> FEATURE:
<223> OTHER INFORMATION: primer
```

<400> SEQUENCE: 115
ggagaccacc aaaccctcca aa                                          22

<210> SEQ ID NO 116
<211> LENGTH: 22
<212> TYPE: DNA
<213> ORGANISM: Artificial
<220> FEATURE:
<223> OTHER INFORMATION: primer

<400> SEQUENCE: 116
gagagttgga gaagggtga ct                                           22

<210> SEQ ID NO 117
<211> LENGTH: 20
<212> TYPE: DNA
<213> ORGANISM: Artificial
<220> FEATURE:
<223> OTHER INFORMATION: primer

<400> SEQUENCE: 117
acctagaggg tctcacctcc                                             20

<210> SEQ ID NO 118
<211> LENGTH: 19
<212> TYPE: DNA
<213> ORGANISM: Artificial
<220> FEATURE:
<223> OTHER INFORMATION: primer

<400> SEQUENCE: 118
ccctggacat caagaatgg                                              19

<210> SEQ ID NO 119
<211> LENGTH: 20
<212> TYPE: DNA
<213> ORGANISM: Artificial
<220> FEATURE:
<223> OTHER INFORMATION: primer

<400> SEQUENCE: 119
cctcaggttg ggcaggaaga                                             20

<210> SEQ ID NO 120
<211> LENGTH: 23
<212> TYPE: DNA
<213> ORGANISM: Artificial
<220> FEATURE:
<223> OTHER INFORMATION: primer

<400> SEQUENCE: 120
gacctaggaa cagtcagcac ggg                                         23

<210> SEQ ID NO 121
<211> LENGTH: 40
<212> TYPE: DNA
<213> ORGANISM: Artificial
<220> FEATURE:
<223> OTHER INFORMATION: primer

<400> SEQUENCE: 121
tcgagcggcc gctctaagtc agggaaagat ccccttcttg                       40

<210> SEQ ID NO 122
<211> LENGTH: 38

```
<212> TYPE: DNA
<213> ORGANISM: Artificial
<220> FEATURE:
<223> OTHER INFORMATION: primer

<400> SEQUENCE: 122
tcgagtcgac gaccatgaag atggtccaac taaagcaa                              38

<210> SEQ ID NO 123
<211> LENGTH: 40
<212> TYPE: DNA
<213> ORGANISM: Artificial
<220> FEATURE:
<223> OTHER INFORMATION: primer

<400> SEQUENCE: 123
tcgaatcgat cactgctctt tctttagtta catgcagccc                            40

<210> SEQ ID NO 124
<211> LENGTH: 38
<212> TYPE: DNA
<213> ORGANISM: Artificial
<220> FEATURE:
<223> OTHER INFORMATION: primer

<400> SEQUENCE: 124
tcgaatcgat attcttgcca agctactctt ccgagcta                              38

<210> SEQ ID NO 125
<211> LENGTH: 28
<212> TYPE: DNA
<213> ORGANISM: Artificial
<220> FEATURE:
<223> OTHER INFORMATION: primer

<400> SEQUENCE: 125
ctcttcagca atatcacggg tagccaac                                         28

<210> SEQ ID NO 126
<211> LENGTH: 28
<212> TYPE: DNA
<213> ORGANISM: Artificial
<220> FEATURE:
<223> OTHER INFORMATION: primer

<400> SEQUENCE: 126
tgcttgcatt gtatgtctgg ctattctg                                         28

<210> SEQ ID NO 127
<211> LENGTH: 20
<212> TYPE: DNA
<213> ORGANISM: Artificial
<220> FEATURE:
<223> OTHER INFORMATION: primer

<400> SEQUENCE: 127
tgctcaggta gtggttgtcg                                                  20
```